US012697244B2

(12) United States Patent
Johannes et al.

(10) Patent No.: US 12,697,244 B2
(45) Date of Patent: Aug. 4, 2026

(54) FLUID COLLECTION DEVICES AND METHODS OF MANUFACTURING SAME

(71) Applicant: PUREWICK CORPORATION

(72) Inventors: Ashley Marie Johannes, Statham, GA (US); Martyn Mitchell, Hertfordshire (GB); Samuel Edmund Whittome, Cambridge (GB); Leanne Yip Heung Win, Wembley (GB)

(73) Assignee: PUREWICK CORPORATION, Covington, GA (US)

( * ) Notice: Subject to any disclaimer, the term of this patent is extended or adjusted under 35 U.S.C. 154(b) by 589 days.

(21) Appl. No.: 18/041,109

(22) PCT Filed: Aug. 9, 2021

(86) PCT No.: PCT/US2021/045188
§ 371 (c)(1),
(2) Date: Feb. 9, 2023

(87) PCT Pub. No.: WO2022/035745
PCT Pub. Date: Feb. 17, 2022

(65) Prior Publication Data
US 2024/0009023 A1    Jan. 11, 2024

Related U.S. Application Data

(60) Provisional application No. 63/064,017, filed on Aug. 11, 2020.

(51) Int. Cl.
*B29D 23/00* (2006.01)
*A61F 5/44* (2006.01)
(Continued)

(52) U.S. Cl.
CPC ............ *A61F 5/455* (2013.01); *A61F 5/4401* (2013.01); *A61F 5/4404* (2013.01); *B29D 23/00* (2013.01);
(Continued)

(58) Field of Classification Search
CPC ................. B26D 3/16; B26D 5/26–28; B26D 2007/013; B26D 7/06; B26D 7/0683;
(Continued)

(56) References Cited

U.S. PATENT DOCUMENTS

| | | |
|---|---|---|
| 670,602 A | 3/1901 | Baker |
| 737,443 A | 8/1903 | Mooers |

(Continued)

FOREIGN PATENT DOCUMENTS

| | | |
|---|---|---|
| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)
(Continued)

*Primary Examiner* — Matthew P Travers
(74) *Attorney, Agent, or Firm* — Ballard Spahr LLP

(57) ABSTRACT

A fluid collection device may include a fluid impermeable barrier and a fluid permeable body in some examples. The fluid permeable body and fluid impermeable barrier may be manufactured and/or assembled by a variety of techniques. In some examples, the fluid permeable body may be extruded and automatically cut to a desired length. In some examples, a tube of a support may be bonded to a strip of material to form the fluid permeable body. In some examples, a conduit may be automatically cut to length. In some examples, a conduit may be placed at a rear of a chamber of the fluid impermeable barrier. In some examples,
(Continued)

the fluid impermeable barrier may include a channel to accept the conduit. In some examples, the fluid impermeable barrier may be formed by multiple injection molded components coupled together.

10 Claims, 21 Drawing Sheets

(51) Int. Cl.

| | |
|---|---|
| A61F 5/455 | (2006.01) |
| B26D 3/16 | (2006.01) |
| B26D 5/28 | (2006.01) |
| B65H 5/06 | (2006.01) |
| B65H 51/10 | (2006.01) |
| B29K 21/00 | (2006.01) |
| B29K 23/00 | (2006.01) |

(52) U.S. Cl.
CPC .................. *B26D 3/16* (2013.01); *B26D 5/28* (2013.01); *B29K 2021/003* (2013.01); *B29K 2023/12* (2013.01); *B29K 2995/0069* (2013.01); *B65H 5/062* (2013.01); *B65H 51/10* (2013.01)

(58) Field of Classification Search
CPC ............ B26D 7/1818; B65H 5/06–062; B65H 51/10; A61F 5/44; A61F 5/4401; A61F 5/4404; A61F 5/451–5/455; B29D 23/00
See application file for complete search history.

(56) References Cited

U.S. PATENT DOCUMENTS

| | | | |
|---|---|---|---|
| 1,015,905 A | | 1/1912 | Northrop |
| 1,032,841 A | | 7/1912 | Koenig |
| 1,178,644 A | | 4/1916 | Johnson |
| 1,387,726 A | | 8/1921 | Karge |
| 1,742,080 A | | 12/1929 | Jones |
| 1,979,899 A | | 11/1934 | Obrien et al. |
| 2,241,010 A | | 5/1941 | Chipley |
| 2,262,772 A | | 11/1941 | Peder |
| 2,326,881 A | | 8/1943 | Packer |
| 2,379,346 A | | 6/1945 | Farrell |
| 2,485,555 A | | 10/1949 | Bester |
| 2,571,357 A | | 10/1951 | Charles |
| 2,613,670 A | | 10/1952 | Edward |
| 2,616,426 A | | 11/1952 | Adele |
| 2,644,234 A | | 7/1953 | Earl |
| 2,648,335 A | | 8/1953 | Chambers |
| 2,789,560 A | | 4/1957 | Weimer |
| 2,859,786 A | | 11/1958 | Tupper |
| 2,944,551 A | | 7/1960 | Carl |
| 2,968,046 A | | 1/1961 | Duke |
| 2,971,512 A | | 2/1961 | Reinhardt |
| 3,032,038 A | | 5/1962 | Swinn |
| 3,077,883 A | | 2/1963 | Hill |
| 3,087,938 A | | 4/1963 | Hans et al. |
| 3,114,916 A | | 12/1963 | Hadley |
| 3,169,528 A | | 2/1965 | Knox et al. |
| 3,171,506 A | | 3/1965 | Therkel |
| 3,175,719 A | | 3/1965 | Herndon |
| 3,194,238 A | | 7/1965 | Breece |
| 3,198,994 A | | 8/1965 | Hildebrandt et al. |
| 3,221,742 A | | 12/1965 | Egon |
| 3,312,221 A | | 4/1967 | Overment |
| 3,312,981 A | | 4/1967 | Mcguire et al. |
| 3,349,768 A | | 10/1967 | Keane |
| 3,362,590 A | | 1/1968 | Gene |
| 3,366,116 A | | 1/1968 | Huck |
| 3,398,848 A | | 8/1968 | Donovan |
| 3,400,717 A | | 9/1968 | Bruce et al. |
| 3,406,688 A | | 10/1968 | Bruce |
| 3,424,163 A | | 1/1969 | Gravdahl |
| 3,425,471 A | | 2/1969 | Yates |
| 3,434,565 A | | 3/1969 | Fischer |
| 3,511,241 A | | 5/1970 | Lee |
| 3,512,185 A | | 5/1970 | Ellis |
| 3,520,300 A | | 7/1970 | Flower |
| 3,528,423 A | | 9/1970 | Lee |
| 3,608,552 A | | 9/1971 | Broerman |
| 3,613,123 A | | 10/1971 | Langstrom |
| 3,648,700 A | | 3/1972 | Warner |
| 3,651,810 A | | 3/1972 | Ormerod |
| 3,661,155 A | | 5/1972 | Lindan |
| 3,683,918 A | | 8/1972 | Pizzella |
| 3,699,815 A | | 10/1972 | Holbrook |
| 3,721,243 A | | 3/1973 | Greth et al. |
| 3,726,277 A | | 4/1973 | Hirschman |
| 3,730,411 A | * | 5/1973 | Brockmuller .......... B65H 35/10 83/175 |
| 3,742,952 A | | 7/1973 | Magers et al. |
| 3,742,953 A | | 7/1973 | Lee |
| 3,757,355 A | | 9/1973 | Allen et al. |
| 3,788,324 A | | 1/1974 | Lim |
| 3,843,016 A | | 10/1974 | Bornhorst et al. |
| 3,863,638 A | | 2/1975 | Rogers et al. |
| 3,863,798 A | | 2/1975 | Kurihara et al. |
| 3,864,759 A | | 2/1975 | Horiuchi |
| 3,865,109 A | | 2/1975 | Elmore et al. |
| 3,881,486 A | | 5/1975 | Fenton |
| 3,881,489 A | | 5/1975 | Hartwell |
| 3,915,189 A | | 10/1975 | Holbrook et al. |
| 3,931,650 A | | 1/1976 | Miller |
| 3,964,786 A | | 6/1976 | Mashuda |
| 3,998,228 A | | 12/1976 | Poidomani |
| 3,999,550 A | | 12/1976 | Martin |
| 4,006,793 A | | 2/1977 | Robinson |
| 4,015,604 A | | 4/1977 | Csillag |
| 4,020,843 A | | 5/1977 | Kanall |
| 4,022,213 A | | 5/1977 | Stein |
| 4,027,776 A | | 6/1977 | Douglas |
| 4,031,897 A | | 6/1977 | Graetz |
| 4,064,962 A | | 12/1977 | Hunt |
| 4,069,817 A | | 1/1978 | Fenole et al. |
| 4,084,589 A | | 4/1978 | Kulvi |
| 4,096,897 A | | 6/1978 | Cammarata |
| 4,116,197 A | | 9/1978 | Bermingham |
| 4,140,739 A | * | 2/1979 | Cotten .................... B29C 57/00 264/294 |
| 4,180,178 A | | 12/1979 | Turner |
| 4,187,953 A | | 2/1980 | Turner |
| 4,194,508 A | | 3/1980 | Anderson |
| 4,197,849 A | | 4/1980 | Bostick |
| 4,200,102 A | | 4/1980 | Duhamel et al. |
| 4,202,058 A | | 5/1980 | Anderson |
| 4,203,503 A | | 5/1980 | Bertotti et al. |
| 4,209,076 A | | 6/1980 | Bertotti et al. |
| 4,223,677 A | | 9/1980 | Anderson |
| 4,233,025 A | | 11/1980 | Larson et al. |
| 4,233,978 A | | 11/1980 | Hickey |
| 4,246,901 A | | 1/1981 | Frosch et al. |
| 4,253,542 A | | 3/1981 | Ruspa et al. |
| 4,257,418 A | | 3/1981 | Hessner |
| 4,270,539 A | | 6/1981 | Frosch et al. |
| 4,280,498 A | | 7/1981 | Jensen |
| 4,281,655 A | | 8/1981 | Terauchi |
| 4,292,916 A | | 10/1981 | Bradley et al. |
| 4,330,239 A | | 5/1982 | Gannaway |
| 4,345,341 A | | 8/1982 | Saito |
| 4,349,029 A | | 9/1982 | Mott |
| 4,352,356 A | | 10/1982 | Tong |
| 4,360,933 A | | 11/1982 | Kimura et al. |
| 4,365,363 A | | 12/1982 | Windauer |
| 4,375,841 A | | 3/1983 | Vielbig |
| 4,387,726 A | | 6/1983 | Denard |
| 4,403,991 A | | 9/1983 | Hill |
| 4,421,511 A | | 12/1983 | Steer et al. |
| 4,425,130 A | | 1/1984 | Desmarais |
| 4,446,986 A | | 5/1984 | Bowen et al. |
| 4,453,938 A | | 6/1984 | Brendling |
| 4,457,314 A | | 7/1984 | Knowles |
| 4,476,879 A | | 10/1984 | Jackson |

(56) References Cited

U.S. PATENT DOCUMENTS

| | | | |
|---|---|---|---|
| 4,526,688 | A | 7/1985 | Schmidt et al. |
| 4,528,703 | A | 7/1985 | Kraus |
| 4,533,354 | A | 8/1985 | Jensen |
| 4,533,357 | A | 8/1985 | Hall |
| D280,438 | S | 9/1985 | Wendt |
| 4,551,141 | A | 11/1985 | Mcneil |
| 4,553,968 | A | 11/1985 | Komis |
| 4,568,341 | A | 2/1986 | Mitchell et al. |
| 4,581,026 | A | 4/1986 | Schneider |
| 4,583,983 | A | 4/1986 | Einhorn et al. |
| 4,589,516 | A | 5/1986 | Inoue et al. |
| 4,601,716 | A | 7/1986 | Smith |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,650,477 | A | 3/1987 | Johnson |
| 4,655,754 | A | 4/1987 | Richmond et al. |
| 4,656,675 | A | 4/1987 | Fajnsztajn |
| 4,681,570 | A | 7/1987 | Dalton |
| 4,681,572 | A | 7/1987 | Tokarz et al. |
| 4,681,577 | A | 7/1987 | Stern et al. |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,723,953 | A | 2/1988 | Pratt et al. |
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,759,753 | A | 7/1988 | Schneider et al. |
| 4,769,215 | A | 9/1988 | Ehrenkranz |
| 4,771,484 | A | 9/1988 | Mozell |
| 4,772,280 | A | 9/1988 | Rooyakkers |
| 4,775,458 | A | 10/1988 | Forester |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,291 | A | 4/1989 | Terauchi et al. |
| 4,820,297 | A | 4/1989 | Kaufman et al. |
| 4,841,728 | A | 6/1989 | Jean et al. |
| 4,846,818 | A | 7/1989 | Keldahl et al. |
| 4,846,819 | A | 7/1989 | Welch |
| 4,846,824 | A | 7/1989 | Lassen et al. |
| 4,846,909 | A | 7/1989 | Klug et al. |
| 4,865,595 | A | 9/1989 | Heyden |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-Ho |
| 4,895,140 | A | 1/1990 | Bellak |
| 4,903,254 | A | 2/1990 | Haas |
| 4,904,248 | A | 2/1990 | Vaillancourt |
| 4,905,692 | A | 3/1990 | More |
| 4,911,262 | A | 3/1990 | Tani et al. |
| 4,930,997 | A | 6/1990 | Bennett |
| 4,936,838 | A | 6/1990 | Cross et al. |
| 4,950,262 | A | 8/1990 | Takagi |
| 4,955,922 | A | 9/1990 | Terauchi |
| 4,957,487 | A | 9/1990 | Gerow |
| 4,965,460 | A | 10/1990 | Tanaka et al. |
| 4,986,823 | A | 1/1991 | Anderson et al. |
| 4,987,849 | A | 1/1991 | Sherman |
| 5,002,541 | A | 3/1991 | Conkling et al. |
| 5,004,463 | A | 4/1991 | Nigay |
| 5,013,308 | A | 5/1991 | Sullivan et al. |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,057,092 | A | 10/1991 | Webster |
| 5,058,088 | A | 10/1991 | Haas et al. |
| 5,071,347 | A | 12/1991 | Mcguire |
| 5,078,707 | A | 1/1992 | Peter |
| 5,084,037 | A | 1/1992 | Barnett |
| 5,100,396 | A | 3/1992 | Zamierowski |
| 5,102,404 | A | 4/1992 | Goldberg et al. |
| 5,112,324 | A | 5/1992 | Wallace |
| 5,134,994 | A | 8/1992 | Say |
| 5,137,033 | A | 8/1992 | Norton |
| 5,147,301 | A | 9/1992 | Ruvio |
| 5,176,667 | A | 1/1993 | Debring |
| 5,195,997 | A | 3/1993 | Carns |
| 5,196,654 | A | 3/1993 | Diflora et al. |
| 5,199,444 | A | 4/1993 | Wheeler |
| 5,203,699 | A | 4/1993 | Mcguire |
| 5,244,458 | A | 9/1993 | Takasu |
| 5,246,454 | A | 9/1993 | Peterson |
| 5,267,988 | A | 12/1993 | Farkas |
| 5,275,307 | A | 1/1994 | Freese |
| 5,282,795 | A | 2/1994 | Finney |
| 5,294,983 | A | 3/1994 | Ersoz et al. |
| 5,295,979 | A | 3/1994 | DeLaurentis et al. |
| 5,295,983 | A | 3/1994 | Kubo |
| 5,300,052 | A | 4/1994 | Kubo |
| 5,304,749 | A | 4/1994 | Crandell |
| 5,312,383 | A | 5/1994 | Kubalak |
| 5,318,550 | A | 6/1994 | Cermak et al. |
| 5,330,457 | A | 7/1994 | Cohen |
| 5,330,459 | A | 7/1994 | Lavon et al. |
| 5,334,174 | A | 8/1994 | Street |
| 5,334,176 | A | 8/1994 | Buenger et al. |
| 5,340,840 | A | 8/1994 | Park et al. |
| 5,382,244 | A | 1/1995 | Telang |
| 5,397,315 | A | 3/1995 | Schmidt et al. |
| 5,409,014 | A | 4/1995 | Napoli et al. |
| 5,409,475 | A | 4/1995 | Steer |
| 5,411,495 | A | 5/1995 | Willingham |
| 5,423,784 | A | 6/1995 | Metz |
| 5,423,788 | A | 6/1995 | Rollins et al. |
| 5,437,836 | A | 8/1995 | Yamada |
| 5,456,246 | A | 10/1995 | Schmieding et al. |
| 5,466,229 | A | 11/1995 | Elson et al. |
| 5,478,334 | A | 12/1995 | Bernstein |
| 5,499,977 | A | 3/1996 | Marx |
| 5,543,042 | A | 8/1996 | Filan et al. |
| D373,928 | S | 9/1996 | Green |
| 5,582,604 | A | 12/1996 | Ahr et al. |
| 5,592,950 | A | 1/1997 | Kopelowicz |
| 5,593,389 | A | 1/1997 | Chang |
| 5,605,161 | A | 2/1997 | Cross |
| 5,614,699 | A | 3/1997 | Yashiro et al. |
| 5,618,277 | A | 4/1997 | Goulter |
| 5,628,735 | A | 5/1997 | Skow |
| 5,632,736 | A | 5/1997 | Block |
| 5,636,643 | A | 6/1997 | Argenta et al. |
| 5,637,104 | A | 6/1997 | Ball et al. |
| 5,662,633 | A | 9/1997 | Doak et al. |
| 5,674,212 | A | 10/1997 | Osborn et al. |
| 5,678,564 | A | 10/1997 | Lawrence et al. |
| 5,678,654 | A | 10/1997 | Uzawa |
| 5,681,297 | A | 10/1997 | Hashimoto et al. |
| 5,687,429 | A | 11/1997 | Rahlff |
| 5,695,485 | A | 12/1997 | Duperret et al. |
| 5,700,254 | A | 12/1997 | Mcdowall et al. |
| 5,701,612 | A | 12/1997 | Daneshvar |
| 5,705,777 | A | 1/1998 | Flanigan et al. |
| 5,735,835 | A | 4/1998 | Holland |
| 5,735,837 | A | 4/1998 | Ishikawa |

(56) References Cited

U.S. PATENT DOCUMENTS

| | | | |
|---|---|---|---|
| 5,752,944 A | 5/1998 | Dann et al. |
| 5,763,333 A | 6/1998 | Suzuki et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,873,869 A | 2/1999 | Hammons et al. |
| 5,876,393 A | 3/1999 | Ahr et al. |
| 5,887,291 A | 3/1999 | Bellizzi |
| 5,891,125 A | 4/1999 | Plumley |
| 5,894,608 A | 4/1999 | Birbara |
| 5,895,349 A | 4/1999 | Tihon |
| D409,303 S | 5/1999 | Oepping |
| 5,911,222 A | 6/1999 | Lawrence et al. |
| 5,956,782 A | 9/1999 | Olguin |
| 5,957,904 A | 9/1999 | Holland |
| 5,968,026 A | 10/1999 | Osborn et al. |
| 5,972,505 A | 10/1999 | Phillips et al. |
| 6,007,526 A | 12/1999 | Passalaqua et al. |
| 6,039,060 A | 3/2000 | Rower |
| 6,050,983 A | 4/2000 | Moore et al. |
| 6,059,762 A | 5/2000 | Boyer et al. |
| 6,061,905 A * | 5/2000 | Logic .................. B23D 31/002 |
| | | 29/890.053 |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,296,627 B1 | 10/2001 | Edwards |
| 6,311,339 B1 | 11/2001 | Kraus |
| 6,316,688 B1 | 11/2001 | Hammons et al. |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,395,956 B1 | 5/2002 | Glasgow et al. |
| 6,398,742 B1 | 6/2002 | Kim |
| 6,406,463 B1 | 6/2002 | Brown |
| 6,409,712 B1 | 6/2002 | Dutari et al. |
| 6,415,888 B2 | 7/2002 | An et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,446,454 B1 | 9/2002 | Lee et al. |
| 6,461,340 B1 | 10/2002 | Lenker et al. |
| 6,467,570 B1 | 10/2002 | Herold |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,526,603 B1 | 3/2003 | Murphy |
| 6,540,729 B1 | 4/2003 | Wada et al. |
| 6,547,771 B2 | 4/2003 | Robertson et al. |
| 6,551,293 B1 | 4/2003 | Mitchell |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,037 B1 | 10/2003 | Bennett |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,848,719 B2 * | 2/2005 | Rowley .................. F16L 9/147 |
| | | 285/55 |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,087,043 B2 | 8/2006 | Dolan |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,166,092 B2 | 1/2007 | Elson et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,658,730 B2 | 2/2010 | Conley |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |

(56) References Cited

U.S. PATENT DOCUMENTS

| | | | |
|---|---|---|---|
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| 7,803,144 B1 | 9/2010 | Vollrath |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,167,860 B1 | 5/2012 | Siegel |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,587 B1 | 3/2013 | Gmuer et al. |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,062 B2 | 10/2013 | Kay |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,737,433 B2 | 8/2017 | Joh |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 9,968,908 B2 | 5/2018 | Ladrech et al. |
| 10,010,393 B1 | 7/2018 | Nguyen et al. |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,500,108 B2 | 12/2019 | Maschino et al. |
| 10,502,198 B2 | 12/2019 | Stumpf et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |

(56)　　　　References Cited

U.S. PATENT DOCUMENTS

| | | |
|---|---|---|
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,623 B2 | 10/2020 | VanMiddendorp et al. |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| 11,002,165 B2 | 5/2021 | Poulin |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,199,116 B2 | 12/2021 | Ostromecki et al. |
| 11,207,206 B2 | 12/2021 | Sharma et al. |
| 11,226,376 B2 | 1/2022 | Yamauchi et al. |
| 11,253,389 B2 | 2/2022 | Sharma et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,911,160 B2 | 2/2024 | Woodard et al. |
| 11,925,575 B2 | 3/2024 | Newton |
| 11,938,053 B2 | 3/2024 | Austermann et al. |
| 11,944,740 B2 | 4/2024 | Hughett et al. |
| 11,994,122 B2 | 5/2024 | Bodain |
| 11,998,475 B2 | 6/2024 | Becker et al. |
| 12,023,457 B2 | 7/2024 | Mann et al. |
| 12,042,422 B2 | 7/2024 | Davis et al. |
| D1,038,385 S | 8/2024 | Ecklund et al. |
| 12,064,372 B2 | 8/2024 | Godinez et al. |
| 12,070,432 B2 | 8/2024 | Tourchak et al. |
| 12,090,083 B2 | 9/2024 | Ecklund et al. |
| 12,121,468 B2 | 10/2024 | Sanchez et al. |
| 12,133,813 B2 | 11/2024 | Ulreich et al. |
| 12,138,195 B2 | 11/2024 | Alder et al. |
| 12,186,229 B2 | 1/2025 | Davis et al. |
| 12,193,962 B2 | 1/2025 | Newton et al. |
| 12,245,966 B2 | 3/2025 | Newton |
| 12,274,638 B2 | 4/2025 | Spector |
| 2001/0037097 A1 | 11/2001 | Cheng et al. |
| 2001/0037098 A1 | 11/2001 | Snyder |
| 2001/0054426 A1 | 12/2001 | Knudson et al. |
| 2002/0019614 A1 | 2/2002 | Woon |
| 2002/0026161 A1 | 2/2002 | Grundke |
| 2002/0026163 A1 | 2/2002 | Grundke |
| 2002/0042945 A1 | 4/2002 | Sands |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2002/0193762 A1 | 12/2002 | Suydam |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0074724 A1 | 4/2003 | Sands |
| 2003/0120178 A1 | 6/2003 | Heki |
| 2003/0129178 A1 | 7/2003 | Wegman et al. |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0147895 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0181201 A1 | 9/2004 | Mizutani et al. |
| 2004/0191919 A1 | 9/2004 | Unger et al. |
| 2004/0194792 A1 | 10/2004 | Zhuang et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0131361 A1 | 6/2005 | Miskie |
| 2005/0137557 A1 | 6/2005 | Swiecicki et al. |
| 2005/0137560 A1 | 6/2005 | Mizutani et al. |
| 2005/0137561 A1 | 6/2005 | Mizutani et al. |
| 2005/0148984 A1 | 7/2005 | Lindsay et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0197645 A1 | 9/2005 | Karpowicz et al. |
| 2005/0215969 A1 | 9/2005 | Mizutani et al. |
| 2005/0273069 A1 | 12/2005 | Mizutani et al. |
| 2005/0273920 A1 | 12/2005 | Marinas |
| 2005/0277903 A1 | 12/2005 | Mizutani et al. |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0113334 A1 | 6/2006 | Mikhail et al. |
| 2006/0155214 A1 | 7/2006 | Wightman |

(56) References Cited

U.S. PATENT DOCUMENTS

| | | |
|---|---|---|
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0025886 A1 | 2/2007 | Yong |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0077099 A1 | 3/2008 | House |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0226541 A1 | 9/2009 | Scholz et al. |
| 2009/0234312 A1 | 9/2009 | Otoole et al. |
| 2009/0251510 A1 | 10/2009 | Noro et al. |
| 2009/0259206 A1 | 10/2009 | Kai et al. |
| 2009/0264840 A1 | 10/2009 | Virginio |
| 2009/0270822 A1 | 10/2009 | Medeiros |
| 2009/0281510 A1 | 11/2009 | Fisher |
| 2009/0283982 A1 | 11/2009 | Thomas |
| 2009/0306610 A1 | 12/2009 | Van Den Heuvel et al. |
| 2010/0004612 A1 | 1/2010 | Thevenin |
| 2010/0030189 A1 | 2/2010 | Fleming |
| 2010/0031429 A1 | 2/2010 | Kim et al. |
| 2010/0032789 A1 | 2/2010 | Schoen et al. |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0198904 A1 | 8/2011 | Thomas et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0209225 A1 | 8/2012 | Hu et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0019374 A1 | 1/2013 | Schwartz |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0144240 A1 | 6/2013 | Ellis |
| 2013/0150813 A1 | 6/2013 | Gordon et al. |
| 2013/0158494 A1 | 6/2013 | Ong et al. |
| 2013/0165880 A1 | 6/2013 | Amos et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0274711 A1 | 10/2013 | O'Day |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0039440 A1 | 2/2014 | Doescher |
| 2014/0058347 A1 | 2/2014 | Marquette |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |

(56) References Cited

U.S. PATENT DOCUMENTS

| | | |
|---|---|---|
| 2014/0257231 A1 | 9/2014 | Wang et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0267862 A1 | 9/2015 | Mishler |
| 2015/0290421 A1 | 10/2015 | Glickman et al. |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0359996 A1 | 12/2015 | Arora et al. |
| 2015/0366699 A1 | 12/2015 | Nelson |
| 2016/0008193 A1 | 1/2016 | Schulke |
| 2016/0029998 A1 | 2/2016 | Brister et al. |
| 2016/0030228 A1 | 2/2016 | Jones |
| 2016/0038356 A1 | 2/2016 | Yao et al. |
| 2016/0051395 A1 | 2/2016 | Ugarte |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0135792 A1 | 5/2016 | Cai |
| 2016/0136338 A1 | 5/2016 | Lee et al. |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0042724 A1 | 2/2017 | Ugarte |
| 2017/0042748 A1 | 2/2017 | Griffin |
| 2017/0100276 A1 | 4/2017 | Joh |
| 2017/0107312 A1 | 4/2017 | Hinayama et al. |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0281419 A1 | 10/2017 | Pintado |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0215649 A1 * | 8/2018 | Wada ........................ B28D 7/02 |
| 2018/0221216 A1 | 8/2018 | Benz et al. |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133126 A1 | 5/2019 | Modak et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0226189 A1 | 7/2019 | Braxton |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365303 A1 | 12/2019 | Bullington et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-Schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1 | 6/2020 | Wiygul |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |

(56) References Cited

U.S. PATENT DOCUMENTS

| | | |
|---|---|---|
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0384242 A1 | 12/2020 | Havard et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0186744 A1 | 6/2021 | Spector |
| 2021/0211568 A1 | 7/2021 | Zhou et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315726 A1 | 10/2021 | Lin |
| 2021/0315727 A1 | 10/2021 | Jiang |
| 2021/0353449 A1 | 11/2021 | Sharma et al. |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0026546 A1 | 1/2022 | Aono et al. |
| 2022/0031290 A1 | 2/2022 | Weed |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062025 A1 | 3/2022 | Shields et al. |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0118165 A1 | 4/2022 | Knapp et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0280710 A1 | 9/2022 | Agrawal et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339023 A1 | 10/2022 | Davis et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0387693 A1 | 12/2022 | Bannwart et al. |
| 2022/0395390 A1 | 12/2022 | Brooks |
| 2022/0395391 A1 | 12/2022 | Saunders et al. |
| 2022/0401252 A1 | 12/2022 | Warren |
| 2022/0409419 A1 | 12/2022 | Garvey et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062944 A1 | 3/2023 | Vollenberg et al. |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0091118 A1 | 3/2023 | Watson |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Yin et al. |
| 2023/0190511 A1 | 6/2023 | Sharma et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277360 A1 | 9/2023 | Lambert et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0389900 A1 | 12/2023 | Xie et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |

(56)  References Cited

U.S. PATENT DOCUMENTS

| | | |
|---|---|---|
| 2024/0033148 A1 | 2/2024 | Gordon et al. |
| 2024/0041638 A1 | 2/2024 | Johannes et al. |
| 2024/0058160 A1 | 2/2024 | Young Joyner et al. |
| 2024/0058161 A1 | 2/2024 | Ulreich et al. |
| 2024/0058520 A1 | 2/2024 | Yin et al. |
| 2024/0065881 A1 | 2/2024 | Kuroda et al. |
| 2024/0082044 A1 | 3/2024 | Nguyen et al. |
| 2024/0099874 A1 | 3/2024 | Sanchez et al. |
| 2024/0108268 A1 | 4/2024 | Woodard et al. |
| 2024/0110318 A1 | 4/2024 | Bendt et al. |
| 2024/0122773 A1 | 4/2024 | Nguyen et al. |
| 2024/0123134 A1 | 4/2024 | Kharkar et al. |
| 2024/0130885 A1 | 4/2024 | Young Joyner et al. |
| 2024/0148539 A1 | 5/2024 | Austermann et al. |
| 2024/0156633 A1 | 5/2024 | Fallows et al. |
| 2024/0164935 A1 | 5/2024 | Newton |
| 2024/0252343 A1 | 8/2024 | Voda |
| 2024/0261131 A1 | 8/2024 | Garvey et al. |
| 2024/0268986 A1 | 8/2024 | Barnes et al. |
| 2024/0268989 A1 | 8/2024 | Martin et al. |
| 2024/0268991 A1 | 8/2024 | Davis |
| 2024/0269027 A1 | 8/2024 | Tourchak et al. |
| 2024/0285425 A1 | 8/2024 | Donohoe et al. |
| 2024/0325190 A1 | 10/2024 | Minchew et al. |
| 2024/0358539 A1 | 10/2024 | Gallup |
| 2024/0358542 A1 | 10/2024 | Richardson et al. |
| 2024/0374414 A1 | 11/2024 | Richardson et al. |
| 2025/0009552 A1 | 1/2025 | Blabas et al. |
| 2025/0073055 A1 | 3/2025 | Ecklund et al. |
| 2025/0107920 A1 | 4/2025 | Fallows et al. |
| 2025/0107921 A1 | 4/2025 | Sanchez et al. |

FOREIGN PATENT DOCUMENTS

| | | | | |
|---|---|---|---|---|
| AU | 2022349367 A1 | 4/2024 | | |
| CA | 2165286 C | 9/1999 | | |
| CA | 2335223 A1 | 1/2000 | | |
| CA | 2354132 A1 | 6/2000 | | |
| CA | 2359091 C | 9/2003 | | |
| CA | 2488867 C | 8/2007 | | |
| CA | 3050918 A1 | 8/2018 | | |
| CA | 3098571 A1 | 11/2019 | | |
| CA | 3144181 A1 | 1/2021 | | |
| CA | 3188651 A1 | 7/2023 | | |
| CN | 2269203 Y | 12/1997 | | |
| CN | 1332620 A | 1/2002 | | |
| CN | 1434693 A | 8/2003 | | |
| CN | 1533755 A | 10/2004 | | |
| CN | 1579348 A | 2/2005 | | |
| CN | 1602825 A | 4/2005 | | |
| CN | 1638708 A | 7/2005 | | |
| CN | 1720888 A | 1/2006 | | |
| CN | 2936204 Y | 8/2007 | | |
| CN | 101262836 A | 9/2008 | | |
| CN | 101522148 A | 9/2009 | | |
| CN | 102159159 A | 8/2011 | | |
| CN | 202184840 U | 4/2012 | | |
| CN | 102481441 A | 5/2012 | | |
| CN | 202463712 U | 10/2012 | | |
| CN | 202950810 U | 5/2013 | | |
| CN | 103533968 A | 1/2014 | | |
| CN | 103717180 A | 4/2014 | | |
| CN | 204562697 U | 8/2015 | | |
| CN | 105411783 A | 3/2016 | | |
| CN | 105451693 A | 3/2016 | | |
| CN | 105534632 A | 5/2016 | | |
| CN | 106132360 A | 11/2016 | | |
| CN | 205849719 U | 1/2017 | | |
| CN | 205924282 U | 2/2017 | | |
| CN | 106726089 A | 5/2017 | | |
| CN | 107847384 A | 3/2018 | | |
| CN | 107920912 A | 4/2018 | | |
| CN | 108420590 A | 8/2018 | | |
| CN | 110171118 A | * 8/2019 | .............. | B26D 3/16 |
| CN | 209285902 U | 8/2019 | | |
| CN | 110381883 A | 10/2019 | | |
| CN | 211198839 U | 8/2020 | | |
| CN | 111991136 A | 11/2020 | | |
| CN | 112022488 A | 12/2020 | | |
| CN | 212234893 U | 12/2020 | | |
| CN | 212466312 U | 2/2021 | | |
| CN | 112566550 A | 3/2021 | | |
| CN | 112603184 A | 4/2021 | | |
| CN | 213490035 U | 6/2021 | | |
| CN | 114007493 A | 2/2022 | | |
| CN | 114375187 A | 4/2022 | | |
| CN | 116096332 A | 5/2023 | | |
| DE | 1516466 A1 | 6/1969 | | |
| DE | 2721330 A1 | 11/1977 | | |
| DE | 2742298 A1 | 3/1978 | | |
| DE | 3104356 A1 | * 9/1982 | .............. | B26D 5/26 |
| DE | 9407554.9 U1 | 5/1995 | | |
| DE | 4443710 A1 | 6/1995 | | |
| DE | 4416094 A1 | 11/1995 | | |
| DE | 4236097 C2 | 10/1996 | | |
| DE | 19619597 A1 | 11/1997 | | |
| DE | 102005037762 B3 | 9/2006 | | |
| DE | 202006018506 U1 | * 3/2007 | .......... | B26D 7/0625 |
| DE | 102011103783 A1 | 12/2012 | | |
| DE | 102012112818 A1 | 6/2014 | | |
| DE | 202015104597 U1 | 7/2016 | | |
| DE | 102018118570 A1 | 2/2020 | | |
| DE | 102020121462 B3 | 1/2022 | | |
| DK | 9600118 | 11/1996 | | |
| EP | 0032138 A2 | 7/1981 | | |
| EP | 0066070 B1 | 12/1982 | | |
| EP | 0068712 A1 | 1/1983 | | |
| EP | 0140470 A1 | 5/1985 | | |
| EP | 0220962 A1 | 5/1987 | | |
| EP | 0140471 B1 | 5/1988 | | |
| EP | 0274753 A2 | 7/1988 | | |
| EP | 0119143 B1 | 11/1988 | | |
| EP | 0483592 A1 | 5/1992 | | |
| EP | 0483730 A1 | 5/1992 | | |
| EP | 0610638 A1 | 8/1994 | | |
| EP | 0613355 A1 | 9/1994 | | |
| EP | 0711536 A1 | 5/1996 | | |
| EP | 0613355 B1 | 1/1997 | | |
| EP | 0680296 B1 | 5/1997 | | |
| EP | 0787472 A1 | 8/1997 | | |
| EP | 0945231 A2 | * 9/1999 | .............. | B26D 5/40 |
| EP | 0966936 A1 | 12/1999 | | |
| EP | 0987293 A1 | 3/2000 | | |
| EP | 1063953 A1 | 1/2001 | | |
| EP | 0653928 B1 | 10/2002 | | |
| EP | 1332738 A1 | 8/2003 | | |
| EP | 1382318 A1 | 1/2004 | | |
| EP | 1089684 B1 | 10/2004 | | |
| EP | 1616542 A1 | 1/2006 | | |
| EP | 1382318 B1 | 5/2006 | | |
| EP | 1063953 B1 | 1/2007 | | |
| EP | 1658831 B1 | 1/2008 | | |
| EP | 1872752 A1 | 1/2008 | | |
| EP | 2180907 A1 | 5/2010 | | |
| EP | 2380532 A1 | 10/2011 | | |
| EP | 2389908 A1 | 11/2011 | | |
| EP | 2601916 A1 | 6/2013 | | |
| EP | 2676643 A1 | 12/2013 | | |
| EP | 2997950 A2 | 3/2016 | | |
| EP | 2879534 B1 | 3/2017 | | |
| EP | 3424471 A1 | 1/2019 | | |
| EP | 3169292 B1 | 11/2019 | | |
| EP | 3753492 A1 | 12/2020 | | |
| EP | 3777801 A1 | 2/2021 | | |
| EP | 3788992 A1 | 3/2021 | | |
| EP | 3576689 B1 | 3/2022 | | |
| EP | 3752110 B1 | 3/2022 | | |
| EP | 3787570 B1 | 3/2022 | | |
| EP | 4025163 A1 | 7/2022 | | |
| EP | 3463180 B1 | 3/2023 | | |
| EP | 3569205 B1 | 6/2023 | | |
| EP | 4218702 A1 | 8/2023 | | |
| EP | 4382082 A2 | 6/2024 | | |
| EP | 4445881 A2 | 10/2024 | | |

(56)    References Cited

FOREIGN PATENT DOCUMENTS

| | | | |
|---|---|---|---|
| EP | 4464288 | A2 | 11/2024 |
| EP | 4527361 | A2 | 3/2025 |
| FR | 2294812 | A1 * | 7/1976 ........... B26D 7/0683 |
| FR | 2826704 | A1 | 1/2003 |
| GB | 871820 | A | 7/1961 |
| GB | 0873045 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H08117271 | A | 5/1996 |
| JP | 2686634 | B2 | 12/1997 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022554252 | A | 12/2022 |
| JP | 2023532132 | A | 7/2023 |
| KR | 200290061 | Y1 | 9/2002 |
| KR | 20030047451 | | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 20120005922 | A | 1/2012 |
| KR | 20140039485 | A | 4/2014 |

(56) References Cited

FOREIGN PATENT DOCUMENTS

| | | | | |
|---|---|---|---|---|
| KR | 101432639 B1 | 8/2014 | | |
| KR | 20180106659 A | 10/2018 | | |
| KR | 20180108774 A | 10/2018 | | |
| KR | 101976679 B1 * | 5/2019 | ............. | B65H 49/34 |
| KR | 101998130 B1 * | 7/2019 | ............. | F16L 11/20 |
| KR | 20230034343 A | 3/2023 | | |
| PT | 2068717 E | 6/2013 | | |
| SE | 505542 C2 | 9/1997 | | |
| TW | 408207 B | 10/2000 | | |
| WO | 8101957 A1 | 7/1981 | | |
| WO | 8804558 A1 | 6/1988 | | |
| WO | 9104714 A2 | 4/1991 | | |
| WO | 9104714 A3 | 6/1991 | | |
| WO | 9220299 A3 | 2/1993 | | |
| WO | 9303690 A1 | 3/1993 | | |
| WO | 9307839 A1 | 4/1993 | | |
| WO | 9309736 A2 | 5/1993 | | |
| WO | 9309736 A3 | 6/1993 | | |
| WO | 9416914 A1 | 8/1994 | | |
| WO | 9514448 A2 | 6/1995 | | |
| WO | 9600096 A1 | 1/1996 | | |
| WO | 9634636 A1 | 11/1996 | | |
| WO | 9817211 A1 | 4/1998 | | |
| WO | 9830336 A1 | 7/1998 | | |
| WO | 0000112 A1 | 1/2000 | | |
| WO | 0000113 A1 | 1/2000 | | |
| WO | 0025651 A1 | 5/2000 | | |
| WO | 0033773 A1 | 6/2000 | | |
| WO | 0057784 A1 | 10/2000 | | |
| WO | 0069377 A1 | 11/2000 | | |
| WO | 0079497 A1 | 12/2000 | | |
| WO | 0145618 A1 | 6/2001 | | |
| WO | 0145621 A1 | 6/2001 | | |
| WO | 02094160 A1 | 11/2002 | | |
| WO | 03013967 A1 | 2/2003 | | |
| WO | 03015671 A1 | 2/2003 | | |
| WO | 03024824 A1 | 3/2003 | | |
| WO | 03055423 A1 | 7/2003 | | |
| WO | 03071931 A2 | 9/2003 | | |
| WO | 03079942 A1 | 10/2003 | | |
| WO | 03071931 A3 | 2/2004 | | |
| WO | 2004019836 A1 | 3/2004 | | |
| WO | 2004024046 A1 | 3/2004 | | |
| WO | 2004026195 A1 | 4/2004 | | |
| WO | 2005051252 A1 | 6/2005 | | |
| WO | 2005060558 A2 | 7/2005 | | |
| WO | 2005074571 A3 | 9/2005 | | |
| WO | 2005089687 A2 | 9/2005 | | |
| WO | 2005107661 A2 | 11/2005 | | |
| WO | 2006021220 A1 | 3/2006 | | |
| WO | 2006037140 A2 | 4/2006 | | |
| WO | 2007005851 A2 | 1/2007 | | |
| WO | 2007007845 A1 | 1/2007 | | |
| WO | 2007042823 A2 | 4/2007 | | |
| WO | 2007055651 A1 | 5/2007 | | |
| WO | 2006098950 A3 | 11/2007 | | |
| WO | 2007128156 A3 | 2/2008 | | |
| WO | 2008026106 A2 | 3/2008 | | |
| WO | 2008078117 A1 | 7/2008 | | |
| WO | 2008104019 A1 | 9/2008 | | |
| WO | 2008141471 A1 | 11/2008 | | |
| WO | 2009004368 A1 | 1/2009 | | |
| WO | 2009004369 A1 | 1/2009 | | |
| WO | 2009052496 A1 | 4/2009 | | |
| WO | 2009052502 A1 | 4/2009 | | |
| WO | 2009007702 A4 | 7/2009 | | |
| WO | 2009101738 A1 | 8/2009 | | |
| WO | 2010058192 A1 | 5/2010 | | |
| WO | 2010030122 A3 | 7/2010 | | |
| WO | 2010101915 A3 | 1/2011 | | |
| WO | 2011018132 A1 | 2/2011 | | |
| WO | 2011018133 A1 | 2/2011 | | |
| WO | 2011024864 A1 | 3/2011 | | |
| WO | 2011054118 A1 | 5/2011 | | |
| WO | 2011079132 A1 | 6/2011 | | |
| WO | 2011107972 A1 | 9/2011 | | |
| WO | 2011108972 A1 | 9/2011 | | |
| WO | 2011117292 A1 | 9/2011 | | |
| WO | 2011123219 A1 | 10/2011 | | |
| WO | 2011132043 A1 | 10/2011 | | |
| WO | 2012012908 A1 | 2/2012 | | |
| WO | 2012020506 A1 | 2/2012 | | |
| WO | 2012065274 A1 | 5/2012 | | |
| WO | 2012097462 A1 | 7/2012 | | |
| WO | 2012098796 A1 | 7/2012 | | |
| WO | 2012101288 A1 | 8/2012 | | |
| WO | 2012175916 A1 | 12/2012 | | |
| WO | 2013018435 A1 | 2/2013 | | |
| WO | 2013033429 A1 | 3/2013 | | |
| WO | 2013055434 A1 | 4/2013 | | |
| WO | 2013082397 A1 | 6/2013 | | |
| WO | 2013103291 A2 | 7/2013 | | |
| WO | 2013131109 A1 | 9/2013 | | |
| WO | 2013167478 A1 | 11/2013 | | |
| WO | 2013177716 A1 | 12/2013 | | |
| WO | 2014041534 A1 | 3/2014 | | |
| WO | 2014046420 A1 | 3/2014 | | |
| WO | 2014118518 A1 | 8/2014 | | |
| WO | 2014160852 A1 | 10/2014 | | |
| WO | 2015023599 A1 | 2/2015 | | |
| WO | 2015052348 A1 | 4/2015 | | |
| WO | 2015068384 A1 | 5/2015 | | |
| WO | 2015169403 A1 | 11/2015 | | |
| WO | 2015170307 A1 | 11/2015 | | |
| WO | 2015197462 A1 | 12/2015 | | |
| WO | 2016051385 A1 | 4/2016 | | |
| WO | 2016055989 A1 | 4/2016 | | |
| WO | 2016071894 A1 | 5/2016 | | |
| WO | 2016103242 A1 | 6/2016 | | |
| WO | 2016116915 A1 | 7/2016 | | |
| WO | 2016124203 A1 | 8/2016 | | |
| WO | 2016139448 A1 | 9/2016 | | |
| WO | 2016166562 A1 | 10/2016 | | |
| WO | 2016167535 A1 | 10/2016 | | |
| WO | 2016191574 A1 | 12/2016 | | |
| WO | 2016200088 A1 | 12/2016 | | |
| WO | 2016200361 A1 | 12/2016 | | |
| WO | 2016204731 A1 | 12/2016 | | |
| WO | 2017001532 A2 | 1/2017 | | |
| WO | 2017075226 A1 | 5/2017 | | |
| WO | 2017100511 A1 | 6/2017 | | |
| WO | 2017152198 A1 | 9/2017 | | |
| WO | 2017153357 A1 | 9/2017 | | |
| WO | 2017162559 A1 | 9/2017 | | |
| WO | 2017205446 A1 | 11/2017 | | |
| WO | 2017209779 A1 | 12/2017 | | |
| WO | 2017210524 A1 | 12/2017 | | |
| WO | 2018022414 A1 | 2/2018 | | |
| WO | 2018044781 A1 | 3/2018 | | |
| WO | 2018056953 A1 | 3/2018 | | |
| WO | 2018090550 A1 | 5/2018 | | |
| WO | 2018138513 A1 | 8/2018 | | |
| WO | 2018144318 A1 | 8/2018 | | |
| WO | 2018144463 A1 | 8/2018 | | |
| WO | 2018150263 A1 | 8/2018 | | |
| WO | 2018150268 A1 | 8/2018 | | |
| WO | 2018152156 A1 | 8/2018 | | |
| WO | 2018183791 A1 | 10/2018 | | |
| WO | 2018150267 A3 | 11/2018 | | |
| WO | 2018235026 A1 | 12/2018 | | |
| WO | 2018235065 A1 | 12/2018 | | |
| WO | 2019004404 A1 | 1/2019 | | |
| WO | 2019041005 A1 | 3/2019 | | |
| WO | 2019044217 A1 | 3/2019 | | |
| WO | 2019044218 A1 | 3/2019 | | |
| WO | 2019044219 A1 | 3/2019 | | |
| WO | 2019050959 A1 | 3/2019 | | |
| WO | 2019065541 A1 | 4/2019 | | |
| WO | 2019096845 A1 | 5/2019 | | |
| WO | 2019150385 A1 | 8/2019 | | |
| WO | 2019161094 A1 | 8/2019 | | |
| WO | 2019188566 A1 | 10/2019 | | |
| WO | 2019190593 A1 | 10/2019 | | |
| WO | 2019212949 A1 | 11/2019 | | |

(56) References Cited

FOREIGN PATENT DOCUMENTS

| | | | |
|---|---|---|---|
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025071622 | A1 | 4/2025 |
| WO | 2025179267 | A1 | 8/2025 |

OTHER PUBLICATIONS

Advisory Action for U.S. Appl. No. 16/433,773 mailed Dec. 29, 2023.

Advisory Action for U.S. Appl. No. 16/449,039 mailed Jan. 25, 2024.

Advisory Action for U.S. Appl. No. 16/452,258 mailed Apr. 8, 2024.

Advisory Action for U.S. Appl. No. 16/478,180 mailed Jun. 7, 2024.

Advisory Action for U.S. Appl. No. 16/478,180 mailed Sep. 7, 2023.

Advisory Action for U.S. Appl. No. 16/904,868 mailed Jan. 2, 2024.

Advisory Action for U.S. Appl. No. 17/051,550 mailed Sep. 8, 2023.

Advisory Action for U.S. Appl. No. 17/051,585 mailed Oct. 17, 2023.

Advisory Action for U.S. Appl. No. 17/051,585 mailed Oct. 8, 2024.

Advisory Action for U.S. Appl. No. 17/179,116 mailed Jan. 8, 2024.

Advisory Action for U.S. Appl. No. 17/444,792 mailed Jul. 8, 2024.

Advisory Action for U.S. Appl. No. 17/446,256 mailed Dec. 8, 2023.

Advisory Action for U.S. Appl. No. 17/446,654 mailed Apr. 15, 2024.

Advisory Action for U.S. Appl. No. 17/448,811 mailed Nov. 15, 2023.

(56)        References Cited

OTHER PUBLICATIONS

Advisory Action for U.S. Appl. No. 17/450,864 mailed Mar. 21, 2024.

Advisory Action for U.S. Appl. No. 17/451,345 mailed Jul. 3, 2024.

Advisory Action for U.S. Appl. No. 17/451,345 mailed Oct. 20, 2023.

Advisory Action for U.S. Appl. No. 17/451,354 mailed Jan. 30, 2024.

Advisory Action for U.S. Appl. No. 17/453,260 mailed Dec. 22, 2023.

Advisory Action for U.S. Appl. No. 17/501,591 mailed Feb. 22, 2024.

Advisory Action for U.S. Appl. No. 17/645,821 mailed Jul. 2, 2024.

Advisory Action for U.S. Appl. No. 17/646,771 mailed Feb. 29, 2024.

Advisory Action for U.S. Appl. No. 17/653,137 mailed Dec. 1, 2023.

Advisory Action for U.S. Appl. No. 17/653,920 mailed Oct. 28, 2024.

Advisory Action for U.S. Appl. No. 17/655,464 mailed Dec. 13, 2023.

Advisory Action for U.S. Appl. No. 17/661,090 mailed Feb. 26, 2024.

Advisory Action for U.S. Appl. No. 17/663,330 mailed Feb. 27, 2024.

Advisory Action for U.S. Appl. No. 17/664,487 mailed Mar. 13, 2024.

Advisory Action for U.S. Appl. No. 17/808,354 mailed Jun. 12, 2024.

Advisory Action for U.S. Appl. No. 18/134,857 mailed Oct. 23, 2024.

Advisory Action for U.S. Appl. No. 18/139,523 mailed Apr. 24, 2024.

Advisory Action for U.S. Appl. No. 18/140,163 mailed Jun. 3, 2024.

Advisory Action for U.S. Appl. No. 18/140,751 mailed Apr. 24, 2024.

Advisory Action for U.S. Appl. No. 18/164,800 mailed Feb. 12, 2024.

Communication of Notice of Opposition of European Application No. 17807547.9 mailed Jan. 5, 2024.

Corrected Notice of Allowability for U.S. Appl. No. 16/369,676 mailed Dec. 7, 2023.

Corrected Notice of Allowability for U.S. Appl. No. 17/326,980 mailed Feb. 8, 2024.

Corrected Notice of Allowability for U.S. Appl. No. 17/450,864 mailed Oct. 24, 2024.

Corrected Notice of Allowability for U.S. Appl. No. 17/501,591 mailed Aug. 9, 2024.

Corrected Notice of Allowability for U.S. Appl. No. 17/657,474 mailed Mar. 13, 2024.

Corrected Notice of Allowability for U.S. Appl. No. 17/657,474 mailed May 14, 2024.

Corrected Notice of Allowability for U.S. Appl. No. 17/664,914 mailed Aug. 9, 2024.

Final Office Action for U.S. Appl. No. 16/369,676 mailed Aug. 31, 2023.

Final Office Action for U.S. Appl. No. 16/433,773 mailed Oct. 10, 2023.

Final Office Action for U.S. Appl. No. 16/433,773 mailed Sep. 9, 2024.

Final Office Action for U.S. Appl. No. 16/449,039 mailed Nov. 21, 2023.

Final Office Action for U.S. Appl. No. 16/452,258 mailed Dec. 21, 2023.

Final Office Action for U.S. Appl. No. 16/478,180 mailed Feb. 28, 2024.

Final Office Action for U.S. Appl. No. 16/904,868 mailed Nov. 2, 2023.

Final Office Action for U.S. Appl. No. 17/051,399 mailed Jan. 8, 2024.

Final Office Action for U.S. Appl. No. 17/051,585 mailed Jul. 5, 2024.

Final Office Action for U.S. Appl. No. 17/051,600 mailed Jun. 27, 2024.

Final Office Action for U.S. Appl. No. 17/179,116 mailed Oct. 31, 2023.

Final Office Action for U.S. Appl. No. 17/444,792 mailed Apr. 3, 2024.

Final Office Action for U.S. Appl. No. 17/446,256 mailed Aug. 7, 2024.

Final Office Action for U.S. Appl. No. 17/446,256 mailed Sep. 19, 2023.

Final Office Action for U.S. Appl. No. 17/446,654 mailed Jan. 31, 2024.

Final Office Action for U.S. Appl. No. 17/447,123 mailed May 14, 2024.

Final Office Action for U.S. Appl. No. 17/450,864 mailed Dec. 28, 2023.

Final Office Action for U.S. Appl. No. 17/451,345 mailed Apr. 18, 2024.

Final Office Action for U.S. Appl. No. 17/451,354 mailed Oct. 28, 2024.

Final Office Action for U.S. Appl. No. 17/451,354 mailed Oct. 30, 2023.

Final Office Action for U.S. Appl. No. 17/453,260 mailed Oct. 5, 2023.

Final Office Action for U.S. Appl. No. 17/501,591 mailed Nov. 14, 2023.

Final Office Action for U.S. Appl. No. 17/597,673 mailed Oct. 22, 2024.

Final Office Action for U.S. Appl. No. 17/645,821 mailed Apr. 3, 2024.

Final Office Action for U.S. Appl. No. 17/646,771 mailed Dec. 21, 2023.

Final Office Action for U.S. Appl. No. 17/653,137 mailed Aug. 7, 2024.

Final Office Action for U.S. Appl. No. 17/653,137 mailed Sep. 21, 2023.

Final Office Action for U.S. Appl. No. 17/653,920 mailed Aug. 14, 2024.

Final Office Action for U.S. Appl. No. 17/655,464 mailed Sep. 1, 2023.

Final Office Action for U.S. Appl. No. 17/661,090 mailed Dec. 11, 2023.

Final Office Action for U.S. Appl. No. 17/663,330 mailed Dec. 12, 2023.

Final Office Action for U.S. Appl. No. 17/664,487 mailed Jan. 4, 2024.

Final Office Action for U.S. Appl. No. 17/808,354 mailed Apr. 10, 2024.

Final Office Action for U.S. Appl. No. 18/003,029 mailed Oct. 22, 2024.

Final Office Action for U.S. Appl. No. 18/134,857 mailed Jul. 25, 2024.

Final Office Action for U.S. Appl. No. 18/139,523 mailed Dec. 22, 2023.

Final Office Action for U.S. Appl. No. 18/140,163 mailed Mar. 27, 2024.

Final Office Action for U.S. Appl. No. 18/140,751 mailed Jan. 17, 2024.

Final Office Action for U.S. Appl. No. 18/164,800 mailed Dec. 6, 2023.

Final Office Action for U.S. Appl. No. 18/164,800 mailed Oct. 22, 2024.

International Search Report and Written Opinion from International Application No. PCT/US2023/018474 mailed Sep. 11, 2023.

International Search Report and Written Opinion from International Application No. PCT/US2023/024805 mailed Dec. 14, 2023.

International Search Report and Written Opinion from International Application No. PCT/US2023/025192 mailed Feb. 7, 2024.

International Search Report and Written Opinion from International Application No. PCT/US2023/025939 mailed Feb. 7, 2024.

(56)             References Cited

OTHER PUBLICATIONS

International Search Report and Written Opinion from International Application No. PCT/US2023/030365 mailed Mar. 13, 2024.

International Search Report and Written Opinion from International Application No. PCT/US2023/030373 mailed Mar. 13, 2024.

International Search Report and Written Opinion from International Application No. PCT/US2023/031433 mailed Mar. 4, 2024.

International Search Report and Written Opinion from International Application No. PCT/US2023/031740 mailed Mar. 4, 2024.

International Search Report and Written Opinion from International Application No. PCT/US2023/036238 mailed Jul. 22, 2024.

International Search Report and Written Opinion from International Application No. PCT/US2023/036868 mailed Jun. 5, 2024.

International Search Report and Written Opinion from International Application No. PCT/US2023/075507 mailed Jun. 13, 2024.

International Search Report and Written Opinion from International Application No. PCT/US2023/077168 mailed Jun. 24, 2024.

International Search Report and Written Opinion from International Application No. PCT/US2023/077208 mailed May 10, 2024.

International Search Report and Written Opinion from International Application No. PCT/US2023/080680 mailed Jul. 22, 2024.

International Search Report and Written Opinion from International Application No. PCT/US2023/085516 mailed Aug. 26, 2024.

Issue Notification for U.S. Appl. No. 16/245,726 mailed Oct. 18, 2023.

Issue Notification for U.S. Appl. No. 16/369,676 mailed Oct. 2, 2024.

Issue Notification for U.S. Appl. No. 16/449,039 mailed Jun. 19, 2024.

Issue Notification for U.S. Appl. No. 16/452,145 mailed Oct. 23, 2024.

Issue Notification for U.S. Appl. No. 17/051,550 mailed Mar. 13, 2024.

Issue Notification for U.S. Appl. No. 17/051,554 mailed Mar. 6, 2024.

Issue Notification for U.S. Appl. No. 17/326,980 mailed Jul. 10, 2024.

Issue Notification for U.S. Appl. No. 17/448,811 mailed Jul. 3, 2024.

Issue Notification for U.S. Appl. No. 17/453,260 mailed Jul. 10, 2024.

Issue Notification for U.S. Appl. No. 17/453,560 mailed Aug. 7, 2024.

Issue Notification for U.S. Appl. No. 17/461,036 mailed Oct. 11, 2023.

Issue Notification for U.S. Appl. No. 17/657,474 mailed Jun. 19, 2024.

Issue Notification for U.S. Appl. No. 17/662,700 mailed Oct. 23, 2024.

Issue Notification for U.S. Appl. No. 17/663,046 mailed Dec. 20, 2023.

Issue Notification for U.S. Appl. No. 18/299,788 mailed Feb. 21, 2024.

Non-Final Office Action for U.S. Appl. No. 16/369,676 mailed Feb. 29, 2024.

Non-Final Office Action for U.S. Appl. No. 16/433,773 mailed Feb. 26, 2024.

Non-Final Office Action for U.S. Appl. No. 16/452,145 mailed Nov. 2, 2023.

Non-Final Office Action for U.S. Appl. No. 16/452,258 mailed Jun. 20, 2024.

Non-Final Office Action for U.S. Appl. No. 16/478,180 mailed Aug. 7, 2024.

Non-Final Office Action for U.S. Appl. No. 16/478,180 mailed Nov. 7, 2023.

Non-Final Office Action for U.S. Appl. No. 16/904,868 mailed Mar. 12, 2024.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,600 mailed Jan. 17, 2024.

Non-Final Office Action for U.S. Appl. No. 17/179,116 mailed Feb. 26, 2024.

Non-Final Office Action for U.S. Appl. No. 17/378,015 mailed Jul. 5, 2024.

Non-Final Office Action for U.S. Appl. No. 17/444,792 mailed Nov. 17, 2023.

Non-Final Office Action for U.S. Appl. No. 17/444,792 mailed Oct. 30, 2024.

Non-Final Office Action for U.S. Appl. No. 17/446,256 mailed Feb. 13, 2024.

Non-Final Office Action for U.S. Appl. No. 17/446,654 mailed Jun. 25, 2024.

Non-Final Office Action for U.S. Appl. No. 17/446,654 mailed Sep. 8, 2023.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/450,864 mailed May 29, 2024.

Non-Final Office Action for U.S. Appl. No. 17/451,345 mailed Jan. 17, 2024.

Non-Final Office Action for U.S. Appl. No. 17/451,345 mailed Jul. 25, 2024.

Non-Final Office Action for U.S. Appl. No. 17/451,354 mailed Apr. 4, 2024.

Non-Final Office Action for U.S. Appl. No. 17/453,560 mailed Oct. 16, 2023.

Non-Final Office Action for U.S. Appl. No. 17/595,747 mailed Jun. 7, 2024.

Non-Final Office Action for U.S. Appl. No. 17/597,408 mailed Aug. 15, 2024.

Non-Final Office Action for U.S. Appl. No. 17/597,673 mailed Mar. 20, 2024.

Non-Final Office Action for U.S. Appl. No. 17/614,173 mailed Sep. 24, 2024.

Non-Final Office Action for U.S. Appl. No. 17/628,411 mailed Sep. 23, 2024.

Non-Final Office Action for U.S. Appl. No. 17/645,821 mailed Oct. 25, 2023.

Non-Final Office Action for U.S. Appl. No. 17/645,821 mailed Sep. 6, 2024.

Non-Final Office Action for U.S. Appl. No. 17/646,771 mailed Apr. 24, 2024.

Non-Final Office Action for U.S. Appl. No. 17/653,137 mailed Jan. 18, 2024.

Non-Final Office Action for U.S. Appl. No. 17/653,314 mailed Aug. 29, 2024.

Non-Final Office Action for U.S. Appl. No. 17/653,920 mailed Mar. 15, 2024.

Non-Final Office Action for U.S. Appl. No. 17/655,464 mailed Mar. 26, 2024.

Non-Final Office Action for U.S. Appl. No. 17/657,474 mailed Sep. 12, 2023.

Non-Final Office Action for U.S. Appl. No. 17/661,090 mailed May 22, 2024.

Non-Final Office Action for U.S. Appl. No. 17/663,330 mailed Jul. 1, 2024.

Non-Final Office Action for U.S. Appl. No. 17/664,487 mailed Jun. 17, 2024.

Non-Final Office Action for U.S. Appl. No. 17/664,914 mailed Jan. 31, 2024.

Non-Final Office Action for U.S. Appl. No. 17/749,340 mailed Aug. 14, 2024.

Non-Final Office Action for U.S. Appl. No. 17/757,311 mailed Oct. 22, 2024.

Non-Final Office Action for U.S. Appl. No. 17/758,316 mailed Aug. 28, 2024.

(56) References Cited

OTHER PUBLICATIONS

Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 26, 2024.
Non-Final Office Action for U.S. Appl. No. 18/140,163 mailed Nov. 9, 2023.
Non-Final Office Action for U.S. Appl. No. 18/140,751 mailed Jun. 21, 2024.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/369,676 mailed Nov. 14, 2023.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/904,868 mailed Sep. 29, 2024.
Notice of Allowance for U.S. Appl. No. 17/051,550 mailed Feb. 7, 2024.
Notice of Allowance for U.S. Appl. No. 17/051,554 mailed Oct. 18, 2023.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/299,788 mailed Nov. 6, 2023.
Notice of Allowance for U.S. Appl. No. 18/389,009 mailed Aug. 28, 2024.
Restriction Requirement for U.S. Appl. No. 17/051,600 mailed Sep. 21, 2023.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/667,097 mailed Mar. 20, 2024.
Restriction Requirement for U.S. Appl. No. 17/756,201 mailed Oct. 4, 2024.
Restriction Requirement for U.S. Appl. No. 17/878,268 mailed Sep. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 15/611,587, filed Jun. 1, 2017.
U.S. Appl. No. 17/013,822, filed Sep. 7, 2020.
U.S. Appl. No. 17/444,792, filed Aug. 10, 2021.
U.S. Appl. No. 17/451,719, filed Oct. 19, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.

(56)                References Cited

OTHER PUBLICATIONS

U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 63,564,696, filed Mar. 13, 2024.
U.S. Appl. No. 63/561,893, filed Dec. 11, 2023.
U.S. Appl. No. 63/568,615, filed Mar. 22, 2024.
U.S. Appl. No. 63/596,012, filed Nov. 3, 2023.
U.S. Appl. No. 63/608,553, filed Dec. 11, 2023.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
"Dictionary.com, ABUT Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (Polyox) in Hydrophilic Matrices", Hydrophilic Matrix Tablets for Oral Controlled Release, AAPS Advances in the Pharmaceutical Sciences vol. 16, 2014, pp. 123-141.
Merriam-Webster Dictionary,, "Embed Definition & Meaning", https://www.merriam-webster.com/dictionary/embed last accessed Aug. 3, 2023, 2003.
Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 17/444,792 mailed Aug. 25, 2023.
Final Office Action for U.S. Appl. No. 16/478,180 mailed May 31, 2023.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/448,811 mailed Aug. 3, 2023.
Final Office Action for U.S. Appl. No. 17/451,345 mailed May 3, 2023.
International Search Report and Written Opinion from International Application No. PCT/US2022/039018 mailed Jan. 10, 2023.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
Issue Notification for U.S. Appl. No. 16/899,956 mailed Mar. 29, 2023.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,258 mailed Apr. 26, 2023.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 18/139,523 mailed Aug. 17, 2023.
Notice of Allowance for U.S. Appl. No. 16/245,726 mailed Jul. 6, 2023.
Notice of Allowance for U.S. Appl. No. 17/051,554 mailed Jul. 6, 2023.
Notice of Allowance for U.S. Appl. No. 17/461,036 mailed Feb. 22, 2023.

(56)     References Cited

OTHER PUBLICATIONS

Notice of Allowance for U.S. Appl. No. 17/461,036 mailed Jun. 30, 2023.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 18/299,788 mailed Jul. 24, 2023.
Restriction Requirement for U.S. Appl. No. 17/326,980 mailed Mar. 20, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Text Messages to Lorena Eckert Re Prototype PureWick Holder dated Apr. 16, 2022.
U.S. Appl. No. 17/664,487, filed May 23, 2022.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/548,152, filed Aug. 28, 2023.
U.S. Appl. No. 63/150,640, filed Feb. 18, 2021.
U.S. Appl. No. 63/308,190, filed Feb. 9, 2022.
*PureWick Corporation* v. *Sage Products, LLC* Transcripts vol. 5, Apr. 1, 2022, 72 pages.
*PureWick Corporation* v. *Sage Products, LLC* Transcripts vol. 1, Mar. 28, 2022, 99 pages.
*PureWick Corporation* v. *Sage Products, LLC* Transcripts vol. 2, Mar. 29, 2022, 106 pages.
*PureWick Corporation* v. *Sage Products, LLC* Transcripts vol. 3, Mar. 30, 2022, 115 pages.
*PureWick Corporation* v. *Sage Products, LLC* Transcripts vol. 4, Mar. 31, 2022, 117 pages.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.

Pieper , et al., "An external urine-collection device for women: A clinical trial", Journal of ER Nursing, vol. 20, No. 2, Mar./Apr. 1993, pp. 51-55.
Vinas , "A Solution for an Awkward—But Serious—Subject", http://www.aero-news.net/index.cfm?do=main.textpost&id=69ae2bb1-838b-4098-a7b5-7flbb2505688 last accessed Feb. 8, 2021, 3 pages.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Advisory Action for U.S. Appl. No. 17/662,700 mailed Jan. 30, 2023.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/899,956 mailed Apr. 19, 2021.
Final Office Action for U.S. Appl. No. 16/904,868 mailed Mar. 10, 2022.

(56)     References Cited

OTHER PUBLICATIONS

Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 17/662,700 mailed Sep. 30, 2022.
Final Office Action for U.S. Appl. No. 29/624,661 mailed Feb. 18, 2020.
International Search Report and Written Opinion from International Application No. PCT/IB2021/057173 mailed Nov. 5, 2021.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.

(56)     References Cited

OTHER PUBLICATIONS

International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/044107 mailed Dec. 23, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 16/905,400 mailed Nov. 30, 2022.

Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 29/624,661 mailed Aug. 4, 2021.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/051,550 mailed Dec. 15, 2022.
Non-Final Office Action for U.S. Appl. No. 17/088,272 mailed Jan. 25, 2021.
Non-Final Office Action for U.S. Appl. No. 17/330,657 mailed Aug. 11, 2021.

(56) References Cited

OTHER PUBLICATIONS

Non-Final Office Action for U.S. Appl. No. 17/451,345 mailed Dec. 7, 2022.
Non-Final Office Action for U.S. Appl. No. 17/662,700 mailed Jul. 22, 2022.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Oct. 6, 2022.
Notice of Allowance for U.S. Appl. No. 17/663,046 mailed Jan. 30, 2023.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.

Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
Restriction Requirement for U.S. Appl. No. 17/446,256 mailed Jan. 23, 2023.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.

(56)          References Cited

OTHER PUBLICATIONS

U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/164,800, filed Feb. 6, 2023.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.

U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.

(56) References Cited

OTHER PUBLICATIONS

Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. No's 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.

Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
"Surface Energy Data for Cellulose acetate, CAS # 9004-35-7", Diviersified Enterprises, 2009, 1 page.
"TUBE Definition & Meaning" Merriam Webster Dictionary, 2025,.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/446,256 mailed Nov. 19, 2024.
Advisory Action for U.S. Appl. No. 17/446,256 mailed Nov. 6, 2025.

(56) References Cited

OTHER PUBLICATIONS

Advisory Action for U.S. Appl. No. 17/446,654 mailed Feb. 28, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/653,137 mailed Nov. 20, 2024.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/757,311 mailed Jul. 2, 2025.
Advisory Action for U.S. Appl. No. 18/003,029 mailed Jan. 8, 2025.
Advisory Action for U.S. Appl. No. 18/164,800 mailed Jan. 8, 2025.
Corrected Notice of Allowability for U.S. Appl. No. 17/444,792 mailed Jun. 24, 2025.
Corrected Notice of Allowability for U.S. Appl. No. 17/646,771 mailed Jan. 17, 2025.
Corrected Notice of Allowability for U.S. Appl. No. 17/653,314 mailed Oct. 29, 2025.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowability for U.S. Appl. No. 18/260,122 mailed Aug. 11, 2025.
Corrected Notice of Allowability for U.S. Appl. No. 18/426,795 mailed Dec. 4, 2024.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 16/452,258 mailed Jan. 6, 2025.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/595,747 mailed Dec. 12, 2024.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/003,029 mailed Nov. 26, 2025.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/164,800 mailed Dec. 5, 2025.
Final Office Action for U.S. Appl. No. 18/265,736 mailed Dec. 1, 2025.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
International Search Report and Written Opinion from International Application No. PCT/US2023/031432 mailed Feb. 29, 2024.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/179,116 mailed Dec. 25, 2024.
Issue Notification for U.S. Appl. No. 17/444,792 mailed Jun. 25, 2025.
Issue Notification for U.S. Appl. No. 17/447,123 mailed Nov. 13, 2024.
Issue Notification for U.S. Appl. No. 17/450,864 mailed Jan. 8, 2025.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/646,771 mailed Mar. 19, 2025.
Issue Notification for U.S. Appl. No. 17/653,920 mailed Oct. 22, 2025.
Issue Notification for U.S. Appl. No. 17/661,090 mailed Feb. 5, 2025.
Issue Notification for U.S. Appl. No. 17/663,330 mailed Feb. 26, 2025.
Issue Notification for U.S. Appl. No. 17/664,914 mailed Nov. 6, 2024.
Issue Notification for U.S. Appl. No. 17/667,097 mailed Dec. 11, 2024.

(56) References Cited

OTHER PUBLICATIONS

Issue Notification for U.S. Appl. No. 17/749,340 mailed May 28, 2025.

Issue Notification for U.S. Appl. No. 17/755,236 mailed Oct. 29, 2025.

Issue Notification for U.S. Appl. No. 17/758,316 mailed Jun. 25, 2025.

Issue Notification for U.S. Appl. No. 17/996,064 mailed Nov. 5, 2025.

Issue Notification for U.S. Appl. No. 17/996,155 mailed Oct. 8, 2025.

Issue Notification for U.S. Appl. No. 17/996,253 mailed Oct. 29, 2025.

Issue Notification for U.S. Appl. No. 17/996,468 mailed Nov. 26, 2025.

Issue Notification for U.S. Appl. No. 18/007,105 mailed Oct. 1, 2025.

Issue Notification for U.S. Appl. No. 18/134,857 mailed May 28, 2025.

Issue Notification for U.S. Appl. No. 18/140,163 mailed Dec. 4, 2024.

Issue Notification for U.S. Appl. No. 18/140,751 mailed Feb. 12, 2025.

Issue Notification for U.S. Appl. No. 18/198,464 mailed Nov. 20, 2024.

Issue Notification for U.S. Appl. No. 18/260,122 mailed Nov. 12, 2025.

Issue Notification for U.S. Appl. No. 18/389,009 mailed Dec. 18, 2024.

Issue Notification for U.S. Appl. No. 18/415,080 mailed Apr. 9, 2025.

Issue Notification for U.S. Appl. No. 18/426,795 mailed Feb. 19, 2025.

Issue Notification for U.S. Appl. No. 18/584,002 mailed Apr. 16, 2025.

Non-Final Office Action for U.S. Appl. No. 16/433,773 mailed Feb. 28, 2025.

Non-Final Office Action for U.S. Appl. No. 16/452,258 mailed Sep. 24, 2025.

Non-Final Office Action for U.S. Appl. No. 17/051,600 mailed Feb. 28, 2025.

Non-Final Office Action for U.S. Appl. No. 17/378,015 mailed Dec. 12, 2025.

Non-Final Office Action for U.S. Appl. No. 17/394,055 mailed Mar. 13, 2025.

Non-Final Office Action for U.S. Appl. No. 17/394,055 mailed Mar. 19, 2025.

Non-Final Office Action for U.S. Appl. No. 17/446,256 mailed Dec. 13, 2024.

Non-Final Office Action for U.S. Appl. No. 17/446,256 mailed Dec. 2, 2025.

Non-Final Office Action for U.S. Appl. No. 17/446,654 mailed May 1, 2025.

Non-Final Office Action for U.S. Appl. No. 17/451,354 mailed Mar. 19, 2025.

Non-Final Office Action for U.S. Appl. No. 17/595,747 mailed Jun. 12, 2025.

Non-Final Office Action for U.S. Appl. No. 17/625,941 mailed Nov. 4, 2024.

Non-Final Office Action for U.S. Appl. No. 17/631,619 mailed Mar. 19, 2025.

Non-Final Office Action for U.S. Appl. No. 17/635,866 mailed Jul. 29, 2025.

Non-Final Office Action for U.S. Appl. No. 17/645,821 mailed Mar. 31, 2025.

Non-Final Office Action for U.S. Appl. No. 17/653,137 mailed Jan. 28, 2025.

Non-Final Office Action for U.S. Appl. No. 17/653,314 mailed May 8, 2025.

Non-Final Office Action for U.S. Appl. No. 17/653,920 mailed Nov. 27, 2024.

Non-Final Office Action for U.S. Appl. No. 17/655,464 mailed Mar. 20, 2025.

Non-Final Office Action for U.S. Appl. No. 17/664,487 mailed May 19, 2025.

Non-Final Office Action for U.S. Appl. No. 17/754,736 mailed Mar. 31, 2025.

Non-Final Office Action for U.S. Appl. No. 17/756,201 mailed Apr. 24, 2025.

Non-Final Office Action for U.S. Appl. No. 17/758,152 mailed Apr. 8, 2025.

Non-Final Office Action for U.S. Appl. No. 17/759,697 mailed Dec. 4, 2024.

Non-Final Office Action for U.S. Appl. No. 17/759,697 mailed Sep. 17, 2025.

Non-Final Office Action for U.S. Appl. No. 17/808,354 mailed Dec. 13, 2024.

Non-Final Office Action for U.S. Appl. No. 17/809,083 mailed Apr. 2, 2025.

Non-Final Office Action for U.S. Appl. No. 17/809,083 mailed Mar. 7, 2025.

Non-Final Office Action for U.S. Appl. No. 17/878,268 mailed Mar. 17, 2025.

Non-Final Office Action for U.S. Appl. No. 17/907,125 mailed Dec. 13, 2024.

Non-Final Office Action for U.S. Appl. No. 17/912,147 mailed May 29, 2025.

Non-Final Office Action for U.S. Appl. No. 17/929,887 mailed Jun. 25, 2025.

Non-Final Office Action for U.S. Appl. No. 17/930,238 mailed Jun. 30, 2025.

Non-Final Office Action for U.S. Appl. No. 17/933,590 mailed Jul. 29, 2025.

Non-Final Office Action for U.S. Appl. No. 17/996,064 mailed Mar. 6, 2025.

Non-Final Office Action for U.S. Appl. No. 18/003,029 mailed Apr. 18, 2025.

Non-Final Office Action for U.S. Appl. No. 18/006,807 mailed May 29, 2025.

Non-Final Office Action for U.S. Appl. No. 18/042,842 mailed May 22, 2025.

Non-Final Office Action for U.S. Appl. No. 18/043,618 mailed May 19, 2025.

Non-Final Office Action for U.S. Appl. No. 18/115,444 mailed Oct. 22, 2025.

Non-Final Office Action for U.S. Appl. No. 18/139,523 mailed Nov. 19, 2025.

Non-Final Office Action for U.S. Appl. No. 18/150,360 mailed Nov. 5, 2025.

Non-Final Office Action for U.S. Appl. No. 18/164,800 mailed Apr. 25, 2025.

Non-Final Office Action for U.S. Appl. No. 18/247,986 mailed Jun. 4, 2025.

Non-Final Office Action for U.S. Appl. No. 18/249,577 mailed Nov. 17, 2025.

Non-Final Office Action for U.S. Appl. No. 18/254,638 mailed Nov. 17, 2025.

Non-Final Office Action for U.S. Appl. No. 18/259,626 mailed Jul. 11, 2025.

Non-Final Office Action for U.S. Appl. No. 18/264,004 mailed May 15, 2025.

Non-Final Office Action for U.S. Appl. No. 18/264,278 mailed Nov. 10, 2025.

Non-Final Office Action for U.S. Appl. No. 18/265,736 mailed Jul. 1, 2025.

Non-Final Office Action for U.S. Appl. No. 18/548,152 mailed Sep. 16, 2025.

Non-Final Office Action for U.S. Appl. No. 18/553,625 mailed Oct. 2, 2025.

Non-Final Office Action for U.S. Appl. No. 18/757,964 mailed Aug. 20, 2025.

(56)                    References Cited

OTHER PUBLICATIONS

Notice of Allowance for U.S. Appl. No. 16/433,773 mailed Oct. 10, 2025.

Notice of Allowance for U.S. Appl. No. 16/478,180 mailed Dec. 16, 2024.

Notice of Allowance for U.S. Appl. No. 16/904,868 mailed Jan. 21, 2025.

Notice of Allowance for U.S. Appl. No. 17/051,399 mailed Nov. 17, 2025.

Notice of Allowance for U.S. Appl. No. 17/051,585 mailed Dec. 26, 2024.

Notice of Allowance for U.S. Appl. No. 17/444,792 mailed Mar. 28, 2025.

Notice of Allowance for U.S. Appl. No. 17/451,345 mailed Jun. 24, 2025.

Notice of Allowance for U.S. Appl. No. 17/451,354 mailed Nov. 18, 2025.

Notice of Allowance for U.S. Appl. No. 17/501,591 mailed Nov. 20, 2024.

Notice of Allowance for U.S. Appl. No. 17/527,769 mailed Nov. 20, 2024.

Notice of Allowance for U.S. Appl. No. 17/596,629 mailed Jan. 29, 2025.

Notice of Allowance for U.S. Appl. No. 17/596,629 mailed May 27, 2025.

Notice of Allowance for U.S. Appl. No. 17/597,673 mailed Feb. 26, 2025.

Notice of Allowance for U.S. Appl. No. 17/625,941 mailed Nov. 13, 2025.

Notice of Allowance for U.S. Appl. No. 17/645,821 mailed Nov. 24, 2025.

Notice of Allowance for U.S. Appl. No. 17/646,771 mailed Dec. 17, 2024.

Notice of Allowance for U.S. Appl. No. 17/653,137 mailed Oct. 22, 2025.

Notice of Allowance for U.S. Appl. No. 17/653,314 mailed Oct. 20, 2025.

Notice of Allowance for U.S. Appl. No. 17/653,920 mailed Jul. 9, 2025.

Notice of Allowance for U.S. Appl. No. 17/663,330 mailed Nov. 20, 2024.

Notice of Allowance for U.S. Appl. No. 17/749,340 mailed Feb. 14, 2025.

Notice of Allowance for U.S. Appl. No. 17/755,236 mailed Jul. 17, 2025.

Notice of Allowance for U.S. Appl. No. 17/758,316 mailed Mar. 24, 2025.

Notice of Allowance for U.S. Appl. No. 17/808,354 mailed Nov. 12, 2025.

Notice of Allowance for U.S. Appl. No. 17/878,268 mailed Oct. 15, 2025.

Notice of Allowance for U.S. Appl. No. 17/907,125 mailed Sep. 26, 2025.

Notice of Allowance for U.S. Appl. No. 17/912,147 mailed Dec. 3, 2025.

Notice of Allowance for U.S. Appl. No. 17/930,238 mailed Dec. 16, 2025.

Notice of Allowance for U.S. Appl. No. 17/996,064 mailed Jul. 29, 2025.

Notice of Allowance for U.S. Appl. No. 17/996,155 mailed Jun. 24, 2025.

Notice of Allowance for U.S. Appl. No. 17/996,155 mailed Mar. 11, 2025.

Notice of Allowance for U.S. Appl. No. 17/996,253 mailed Apr. 11, 2025.

Notice of Allowance for U.S. Appl. No. 17/996,253 mailed Jul. 11, 2025.

Notice of Allowance for U.S. Appl. No. 17/996,468 mailed Apr. 14, 2025.

Notice of Allowance for U.S. Appl. No. 17/996,468 mailed Jul. 15, 2025.

Notice of Allowance for U.S. Appl. No. 18/007,105 mailed Jun. 17, 2025.

Notice of Allowance for U.S. Appl. No. 18/044,413 mailed Sep. 16, 2025.

Notice of Allowance for U.S. Appl. No. 18/134,857 mailed Feb. 20, 2025.

Notice of Allowance for U.S. Appl. No. 18/260,122 mailed Jul. 30, 2025.

Notice of Allowance for U.S. Appl. No. 18/415,080 mailed Dec. 30, 2024.

Notice of Allowance for U.S. Appl. No. 18/426,795 mailed Nov. 20, 2024.

Notice of Allowance for U.S. Appl. No. 18/584,002 mailed Jan. 8, 2025.

Restriction Requirement for U.S. Appl. No. 17/625,887 mailed Sep. 2, 2025.

Restriction Requirement for U.S. Appl. No. 17/754,736 mailed Nov. 20, 2024.

Restriction Requirement for U.S. Appl. No. 17/755,236 mailed Apr. 24, 2025.

Restriction Requirement for U.S. Appl. No. 17/758,152 mailed Nov. 5, 2024.

Restriction Requirement for U.S. Appl. No. 17/809,083 mailed Dec. 31, 2024.

Restriction Requirement for U.S. Appl. No. 17/929,887 mailed Mar. 10, 2025.

Restriction Requirement for U.S. Appl. No. 17/930,238 mailed Apr. 17, 2025.

Restriction Requirement for U.S. Appl. No. 17/996,556 mailed Aug. 11, 2025.

Restriction Requirement for U.S. Appl. No. 18/034,902 mailed Nov. 6, 2025.

Restriction Requirement for U.S. Appl. No. 18/150,360 mailed May 19, 2025.

Restriction Requirement for U.S. Appl. No. 18/246,121 mailed Jul. 25, 2025.

Restriction Requirement for U.S. Appl. No. 18/249,577 mailed Aug. 25, 2025.

Restriction Requirement for U.S. Appl. No. 18/254,638 mailed Jul. 21, 2025.

Restriction Requirement for U.S. Appl. No. 18/294,370 mailed Nov. 26, 2025.

Restriction Requirement for U.S. Appl. No. 18/373,424 mailed Nov. 14, 2025.

Restriction Requirement for U.S. Appl. No. 18/376,274 mailed Dec. 10, 2025.

Restriction Requirement for U.S. Appl. No. 18/549,387 mailed Dec. 9, 2025.

Restriction Requirement for U.S. Appl. No. 18/551,492 mailed Nov. 10, 2025.

Restriction Requirement for U.S. Appl. No. 18/662,216 mailed Nov. 26, 2025.

Restriction Requirement for U.S. Appl. No. 19/237,638 mailed Dec. 18, 2025.

Supplemental Notice of Allowance for U.S. Appl. No. 17/597,673 mailed Apr. 10, 2025.

U.S. Appl. No. 17/596,629, filed Dec. 15, 2021.

U.S. Appl. No. 18/034,902, filed May 2, 2023.

U.S. Appl. No. 18/951,944, filed Nov. 19, 2024.

U.S. Appl. No. 18/957,011, filed Nov. 22, 2024.

U.S. Appl. No. 18/974,367, filed Dec. 9, 2024.

U.S. Appl. No. 18/982,930, filed Dec. 16, 2024.

U.S. Appl. No. 19/038,774, filed Jan. 28, 2025.

U.S. Appl. No. 19/039,165, filed Jan. 28, 2025.

U.S. Appl. No. 19/046,047, filed Feb. 5, 2025.

U.S. Appl. No. 19/047,728, filed Feb. 7, 2025.

U.S. Appl. No. 19/048,004, filed Feb. 7, 2025.

U.S. Appl. No. 19/049,501, filed Feb. 10, 2025.

U.S. Appl. No. 19/049,783, filed Feb. 10, 2025.

U.S. Appl. No. 19/058,726, filed Feb. 20, 2025.

U.S. Appl. No. 19/069,480, filed Mar. 4, 2025.

(56)     References Cited

OTHER PUBLICATIONS

U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/491,481, filed Dec. 9, 2025.
U.S. Appl. No. 19/494,631, filed Dec. 18, 2025.
U.S. Appl. No. 63/181,709, filed Apr. 29, 2021.
U.S. Appl. No. 63/720,004, filed Nov. 13, 2024.

* cited by examiner

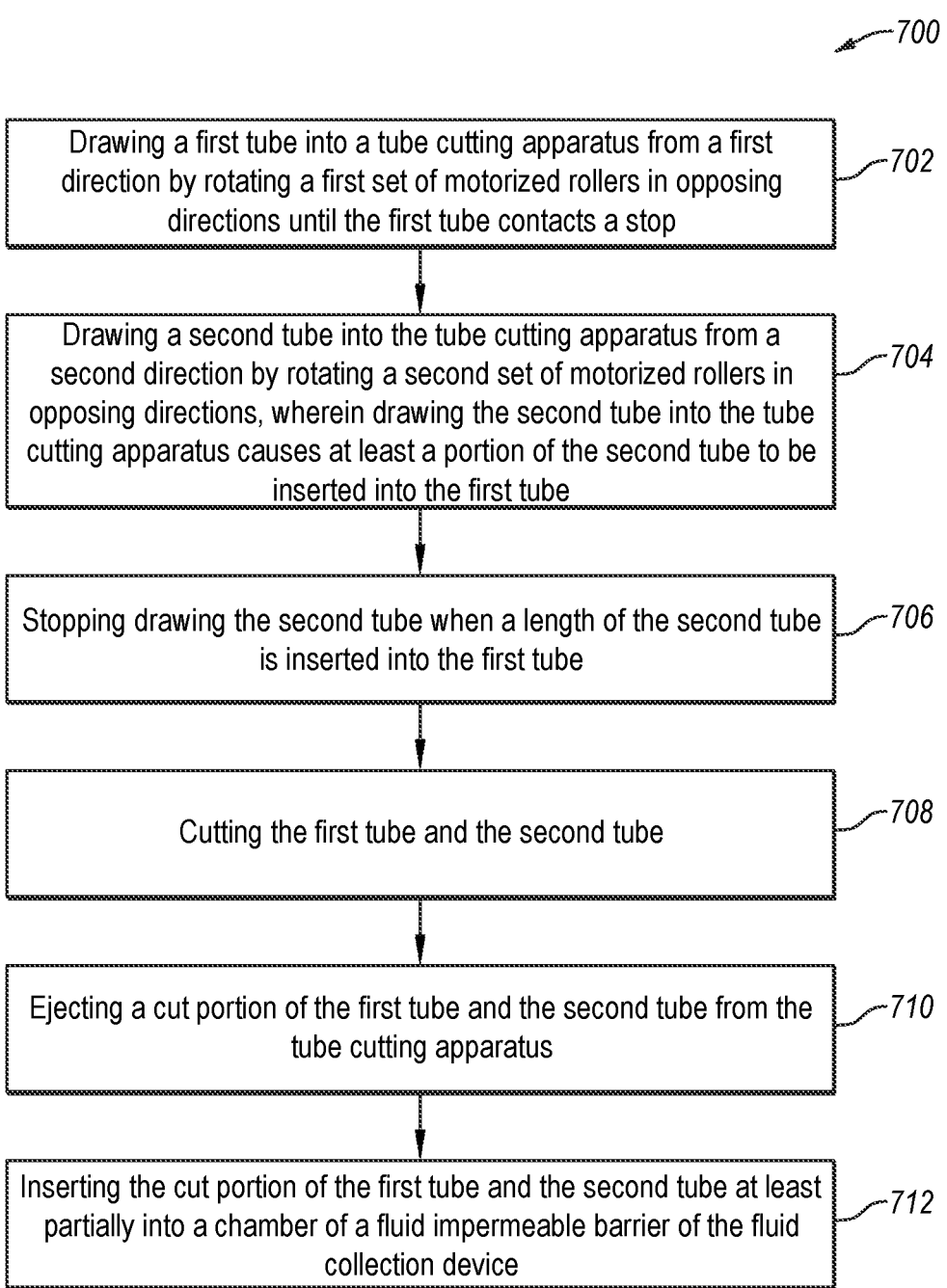

┌─ 700

┌──────────────────────────────────────────────────────────────┐
│ Drawing a first tube into a tube cutting apparatus from a first │  ─ 702
│ direction by rotating a first set of motorized rollers in opposing │
│ directions until the first tube contacts a stop                 │
└──────────────────────────────────────────────────────────────┘

┌──────────────────────────────────────────────────────────────┐
│ Drawing a second tube into the tube cutting apparatus from a    │  ─ 704
│ second direction by rotating a second set of motorized rollers in │
│ opposing directions, wherein drawing the second tube into the tube │
│ cutting apparatus causes at least a portion of the second tube to be │
│ inserted into the first tube                                    │
└──────────────────────────────────────────────────────────────┘

┌──────────────────────────────────────────────────────────────┐
│ Stopping drawing the second tube when a length of the second tube │  ─ 706
│ is inserted into the first tube                                 │
└──────────────────────────────────────────────────────────────┘

┌──────────────────────────────────────────────────────────────┐
│ Cutting the first tube and the second tube                      │  ─ 708
└──────────────────────────────────────────────────────────────┘

┌──────────────────────────────────────────────────────────────┐
│ Ejecting a cut portion of the first tube and the second tube from the │  ─ 710
│ tube cutting apparatus                                          │
└──────────────────────────────────────────────────────────────┘

┌──────────────────────────────────────────────────────────────┐
│ Inserting the cut portion of the first tube and the second tube at least │  ─ 712
│ partially into a chamber of a fluid impermeable barrier of the fluid │
│ collection device                                               │
└──────────────────────────────────────────────────────────────┘

FIG. 7

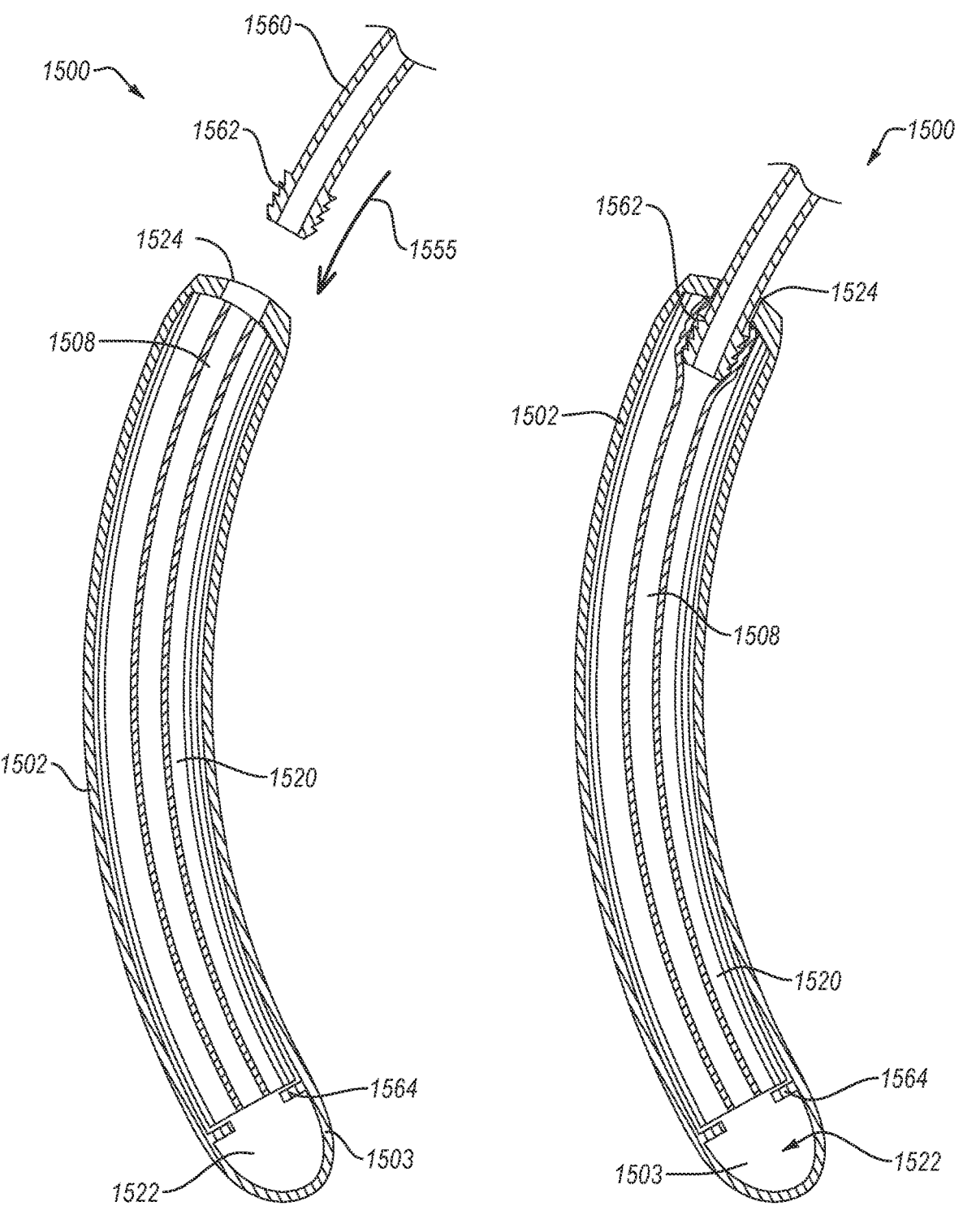
FIG. 15A         FIG. 15B

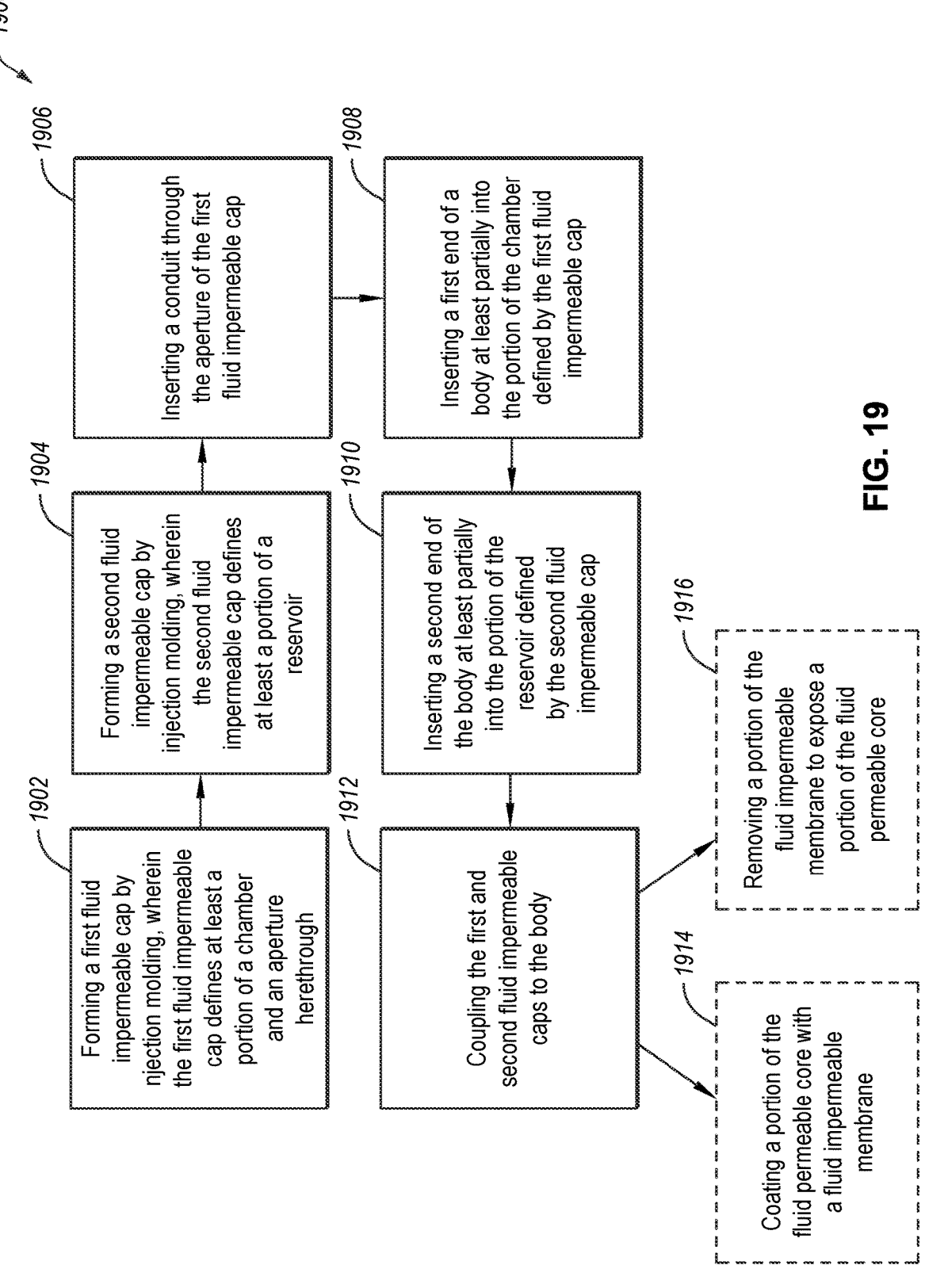

1900

1902 Forming a first fluid impermeable cap by injection molding, wherein the first fluid impermeable cap defines at least a portion of a chamber and an aperture herethrough 1904 Forming a second fluid impermeable cap by injection molding, wherein the second fluid impermeable cap defines at least a portion of a reservoir 1906 Inserting a conduit through the aperture of the first fluid impermeable cap 1908 Inserting a first end of a body at least partially into the portion of the chamber defined by the first fluid impermeable cap 1910 Inserting a second end of the body at least partially into the portion of the reservoir defined by the second fluid impermeable cap 1912 Coupling the first and second fluid impermeable caps to the body 1914 Coating a portion of the fluid permeable core with a fluid impermeable membrane 1916 Removing a portion of the fluid impermeable membrane to expose a portion of the fluid permeable core

FIG. 19

FLUID COLLECTION DEVICES AND METHODS OF MANUFACTURING SAME

CROSS-REFERENCE TO RELATED APPLICATIONS

This application is a U.S. Nationalization of PCT International Application No. PCT/US2021/045188 filed on Aug. 9, 2021, which claims priority to U.S. Provisional Patent Application No. 63/064,017 filed on Aug. 11, 2020, the disclosure of each of which is incorporated herein, in their entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, pressure ulcers, spills, and other hygiene issues. Urinary catheters be can be uncomfortable, painful, and can cause urinary tract infections. Recently, non-invasive fluid collection devices have been developed for use with immobile and/or limited mobility individuals. By non-invasive, it is meant that the catheter may be placed externally (e.g., outside an opening of the urethra).

Due to the nature of bodily fluids, fluid collection devices may need to be sterilized and/or replaced frequently. Accordingly, improved manufacturing techniques of fluid collection devices to ensure quality consistency and/or reduce cost may be desired.

SUMMARY

Embodiments disclosed herein are fluid collection devices, methods of manufacturing fluid collection devices and components thereof.

According to an example of the present disclosure, a method of manufacturing a portion of a fluid collection device may include drawing a length of tubing through a first set of motorized rollers by rotating rollers of the first set of motorized rollers in opposing directions, drawing the length of tubing through a second set of motorized rollers by rotating rollers of the second set of motorized rollers in opposing directions, stopping rotation of the first set of motorized rollers and the second set of motorized rollers when an end of the length of tubing contacts a stop, cutting the length of tubing at a location between the first set of motorized rollers and the second set of motorized rollers, and inserting the length of tubing at least partially into a chamber of a fluid impermeable barrier of the fluid collection device.

According to an example of the present disclosure, a method of manufacturing a portion of a fluid collection device may include drawing a first tube into a tube cutting apparatus from a first direction by rotating a first set of motorized rollers in opposing directions until the first tube contacts a stop, drawing a second tube into the tube cutting apparatus from a second direction by rotating a second set of motorized rollers in opposing directions, wherein drawing the second tube into the tube cutting apparatus causes at least a portion of the second tube to be inserted into the first tube, stopping drawing the second tube when a length of the second tube is inserted into the first tube, cutting the first tube and the second tube, and inserting the cut portion of the first tube and the second tube at least partially into a chamber of a fluid impermeable barrier of the fluid collection device.

According to an example of the present disclosure, a method of manufacturing a portion of a fluid collection device may include drawing a tube from a first reel, drawing a strip of material from a second reel, positioning the strip of material on a portion of a perimeter of the tube, coupling the strip of material to the tube to form a fluid permeable body, and inserting at least a portion of the fluid permeable body into a chamber of a fluid impermeable barrier.

According to an example of the present disclosure, a fluid collection apparatus may include a fluid impermeable barrier having an inner surface at least partially defining a chamber, a first end region defining an aperture extending therethrough and including a first outer surface portion, and a second end region distal to the first end region, the fluid impermeable barrier also defining an opening extending longitudinally along the fluid impermeable barrier and configured to be positioned adjacent to a female urethra, and a fluid permeable body positioned at least partially within the chamber to extend across at least a portion of the opening and configured to wick fluid away from the opening, wherein the fluid permeable body includes a support positioned at least partially within the chamber and a fluid permeable membrane coupled to the support and covering only a portion of the support.

According to an example of the present disclosure, a fluid collection apparatus may include a fluid impermeable barrier having an inner surface at least partially defining a chamber, a first end region defining an aperture extending therethrough and including a first outer surface portion, and a second end region distal to the first end region, the fluid impermeable barrier also defining an opening extending longitudinally along the fluid impermeable barrier and configured to be positioned adjacent to a female urethra, and a fluid permeable body positioned at least partially within the chamber to extend across at least a portion of the opening and configured to wick fluid away from the opening, wherein the fluid permeable body includes a support positioned at least partially within the chamber, and a fluid permeable membrane covering at least a portion of the support, wherein the fluid permeable membrane is coupled to the fluid impermeable barrier at a perimeter proximate to the opening.

According to an example of the present disclosure, a fluid collection apparatus may include a fluid impermeable barrier having an inner surface at least partially defining a chamber, a first end region defining an aperture extending therethrough and including a first outer surface portion, and a second end region distal to the first end region, the fluid impermeable barrier also defining an opening extending longitudinally along the fluid impermeable barrier and configured to be positioned adjacent to a female urethra, and a fluid permeable body positioned at least partially within the chamber to extend across at least a portion of the opening and configured to wick fluid away from the opening, wherein the fluid permeable body includes an open cell polyethylene foam.

According to an example of the present disclosure, a fluid collection apparatus may include a fluid impermeable barrier having an inner surface at least partially defining a chamber, a first end region defining an aperture extending therethrough and including a first outer surface portion, and a second end region distal to the first end region, the fluid impermeable barrier also defining an opening extending longitudinally along the fluid impermeable barrier and configured to be positioned adjacent to a female urethra, and a fluid permeable body positioned at least partially within the chamber to extend across at least a portion of the opening and configured to wick fluid away from the opening, wherein the fluid permeable body includes a support at least partially defining a channel along a long axis of the fluid permeable body, wherein the fluid permeable body is positioned such that the channel is enclosed within the chamber.

According to an example of the present disclosure, a fluid collection apparatus may include a fluid impermeable barrier having an inner surface at least partially defining a chamber, a first end region defining an aperture extending therethrough and including a first outer surface portion, and a second end region distal to the first end region, the fluid impermeable barrier also defining an opening extending longitudinally along the fluid impermeable barrier and configured to be positioned adjacent to a female urethra, wherein the inner surface further defines a channel extending from the aperture longitudinally along the fluid impermeable barrier, and a fluid permeable body positioned at least partially within the chamber to extend across at least a portion of the opening and configured to wick fluid away from the opening.

According to an example of the present disclosure, a fluid collection apparatus may include a fluid impermeable barrier having an inner surface at least partially defining a chamber, a first end region defining an aperture extending therethrough and including a first outer surface portion, and a second end region distal to the first end region, the fluid impermeable barrier also defining an opening extending longitudinally along the fluid impermeable barrier and configured to be positioned adjacent to a female urethra, and a fluid permeable body positioned at least partially within the chamber to extend across at least a portion of the opening and configured to wick fluid away from the opening, wherein the fluid permeable body includes a fluid permeable membrane surrounding a support, wherein the support includes a central tube and a plurality of fins extending from an outer perimeter of the central tube to the fluid permeable membrane.

According to an example of the present disclosure, a fluid collection apparatus may include a fluid impermeable barrier having an inner surface at least partially defining a chamber, a first end region defining an aperture extending therethrough and including a first outer surface portion, and a second end region distal to the first end region, the fluid impermeable barrier also defining an opening extending longitudinally along the fluid impermeable barrier and configured to be positioned adjacent to a female urethra, a fluid permeable body positioned at least partially within the chamber to extend across at least a portion of the opening and configured to wick fluid away from the opening, a conduit extending through a bore defined by the fluid permeable body, and a hydraulic connector extending through the aperture from the first outer surface portion and coupled to the conduit.

According to an example of the present disclosure, a fluid collection apparatus may include a fluid impermeable barrier comprising an integrally formed main body having a first inner surface at least partially defining a chamber, the main body further defining a tube extending from a first end region into the chamber and further extending from an outer surface portion of the first end region and an end cap at a second end region distal to the first end region, the end cap having a second inner surface at least partially defining the chamber and a second end region distal to the first end region, wherein the fluid impermeable barrier also defines an opening extending longitudinally along the fluid impermeable barrier and configured to be positioned adjacent to a female urethra, and a fluid permeable body positioned at least partially within the chamber to extend across at least a portion of the opening and configured to wick fluid away from the opening.

According to an example of the present disclosure, a method of manufacturing at least a portion of a fluid collection device may include integrally forming a main body of a fluid impermeable barrier by injection molding, wherein the main body defines at least a portion of a chamber of the fluid impermeable barrier, at least a portion of an opening into the chamber and a tube extending from the chamber to an external surface of the fluid impermeable barrier, forming an end cap of the fluid impermeable barrier by injection molding, wherein the end cap defines at least another portion of the chamber, inserting a fluid permeable body at least partially into the portion of the chamber defined by the main body, placing the end cap on the fluid permeable body such that the fluid permeable body is at least partially inserted in the portion of the chamber defined by the end cap, and coupling the main body to the end cap.

According to an example of the present disclosure, a fluid collection apparatus may include a first fluid impermeable cap having a first inner surface at least partially defining a chamber and an aperture extending from the first inner surface to an outer surface at a first end region, a second fluid impermeable cap having a second inner surface at least partially defining a reservoir at a second end region, a body including a fluid permeable core partially surrounded by a fluid impermeable membrane, the fluid permeable core defining a bore, wherein the fluid permeable core is partially exposed by an opening in the fluid impermeable membrane and configured to wick fluid away from the opening, and a conduit extending through the aperture from the outer surface and further extending at least partially through the bore.

According to an example of the present disclosure, a method of manufacturing at least a portion of a fluid collection device may include forming a first fluid impermeable cap by injection molding, wherein the first fluid impermeable cap defines at least a portion of a chamber and an aperture therethrough, forming a second fluid impermeable cap by injection molding, wherein the second fluid impermeable cap defines at least a portion of a reservoir, inserting a conduit through the aperture of the first fluid impermeable cap, inserting a first end of a body at least partially into the portion of the chamber defined by the first fluid impermeable cap, and inserting a second end of the body at least partially into the portion of the reservoir defined by the second fluid impermeable cap.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 7 is a flow chart of a method according to at least one embodiment of the disclosure.

FIG. 15A is a cross-sectional view of a fluid collection device along a long axis of the fluid collection device according to at least one embodiment of the disclosure.

FIG. 15B is a cross-sectional view of the fluid collection device of FIG. 15A showing the hydraulic connector inserted according to an embodiment of the disclosure.

FIG. 19 is a flow chart of a method according to at least one embodiment of the disclosure.

DETAILED DESCRIPTION

Embodiments disclosed herein are directed to fluid collection devices and methods of manufacturing same. The fluid collection devices disclosed herein are configured to collect fluids from an individual. The fluids collected by the fluid collection devices can include urine. The fluids collected by the fluid collection devices can also include at least one of vaginal discharge, penile discharge, reproductive fluids, blood, sweat, or other bodily fluids.

The fluid collection devices may include one or more components for drawing (e.g., wicking) fluid from a wearer and/or a surface of the fluid collection device into an interior of the fluid collection device. In some embodiments, the fluid collection devices may include a fluid permeable body for wicking fluid into the fluid collection device. In some embodiments, the fluid permeable body may include a fluid permeable membrane at least partially surrounding a support. In some embodiments, the support may be a fluid permeable support. In some embodiments, the fluid collection device may include a fluid permeable support without a fluid permeable membrane. The support alone or in combination with the fluid permeable membrane may direct fluids to an interior of the fluid collection device where the fluid may be removed from the fluid collection device.

Figure 1A:
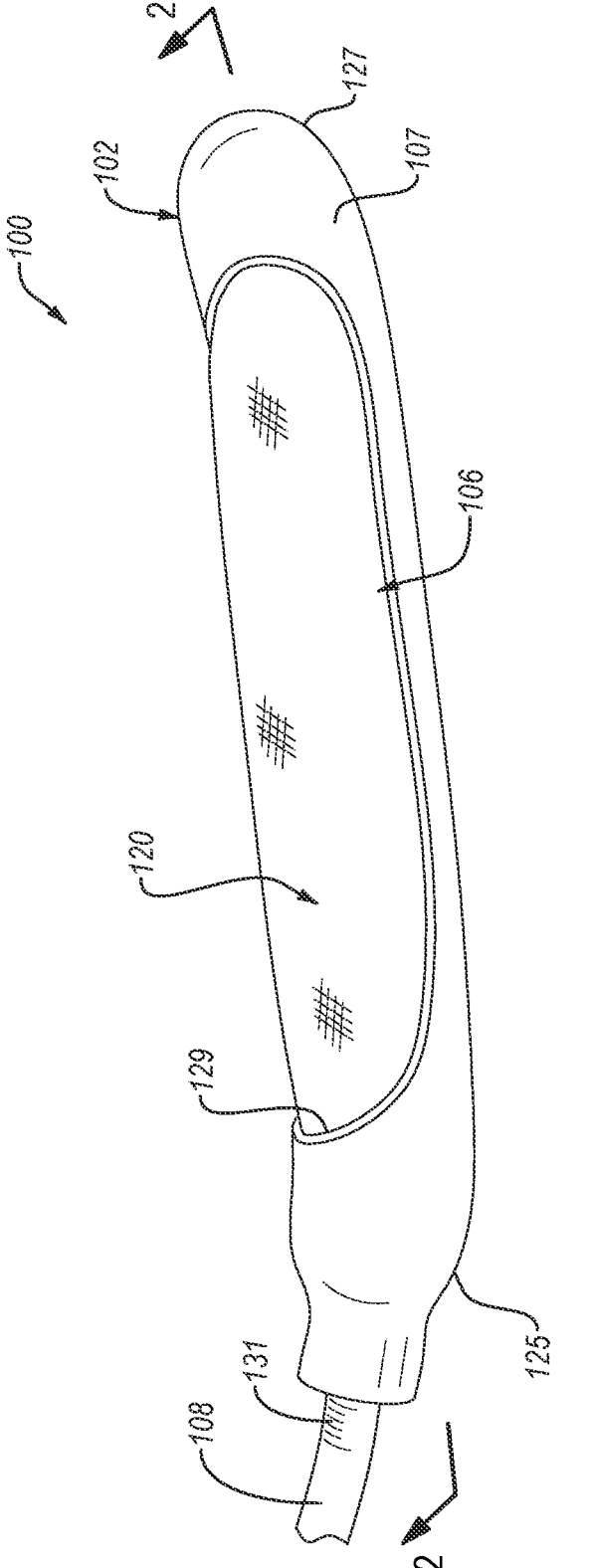
FIG. 1A is an isometric front view of a female fluid collection device according to at least one embodiment of the disclosure.
Figure 1B:
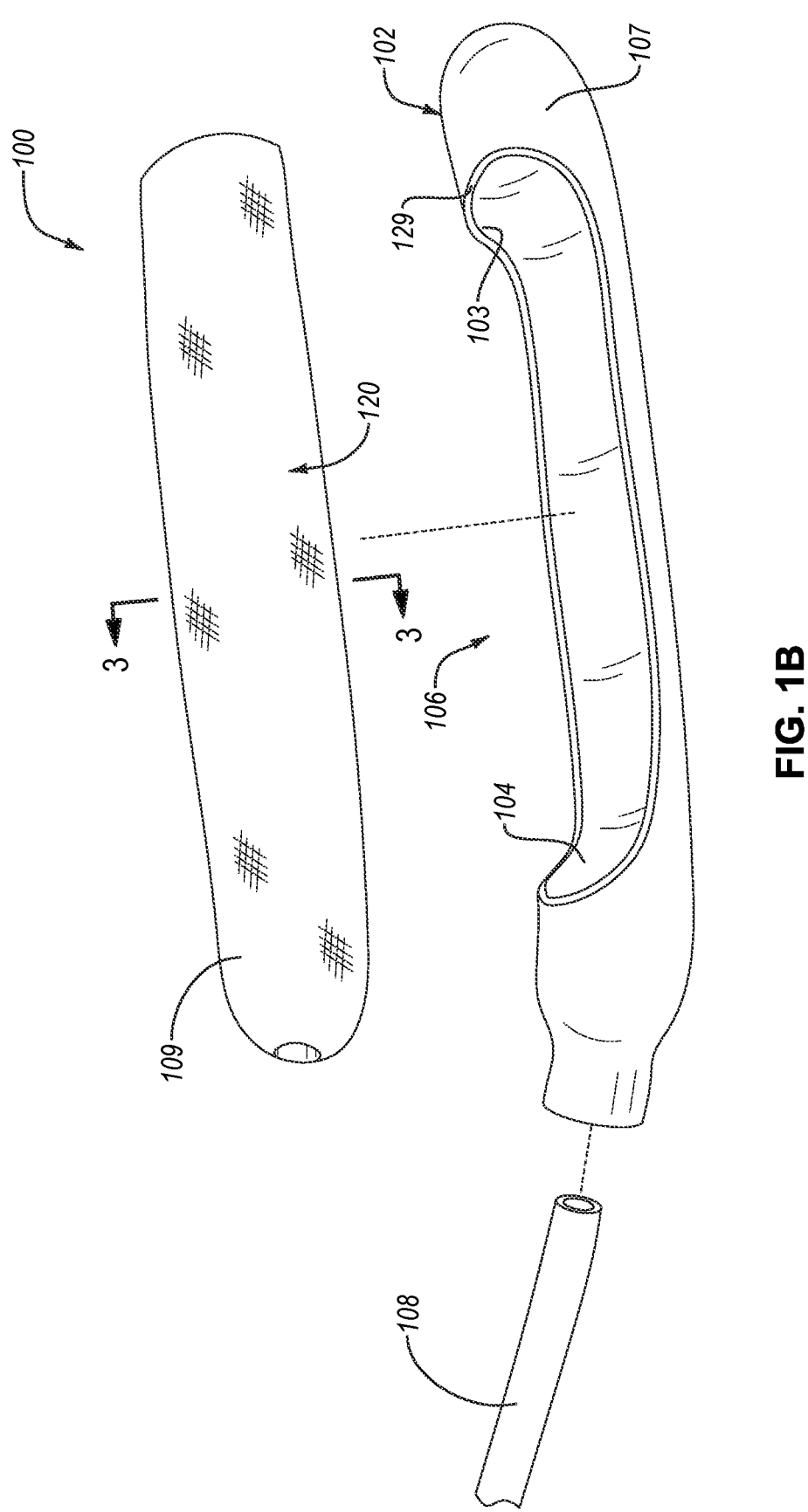
FIG. 1B is an exploded isometric view of the female fluid collection device of FIG. 1A.

FIG. 1A is an isometric view of a fluid collection device 100 according to at least one embodiment of the disclosure. The fluid collection device 100 is an example of a female fluid collection device 100 that is configured to receive fluids from a female wearer. The fluid collection device 100 includes a fluid impermeable barrier 102 having a first end region 125 and a second end region 127. The first end region 125 may include an aperture 124 for accepting a conduit 108 that may couple the fluid collection device 100 to a vacuum source. The fluid impermeable barrier 102 at least partially defines a chamber 104 (e.g., interior region, shown in FIG. 1B) and includes an inward border or edge 129 defining an opening 106. The fluid impermeable barrier 102 may be substantially cylindrical in shape between the first end region 125 and the second end region 127. The opening 106 is formed in and extends through the fluid impermeable barrier 102, thereby enabling fluids to enter the chamber 104 from outside of the fluid collection device 100. The opening 106 can be configured to be positioned adjacent to a female urethra in some applications.

In the fluid collection device 100 is configured to receive fluids into the chamber 104 via the opening 106. For example, the opening 106 can exhibit an elongated shape that is configured to extend from a first location below the urethral opening (e.g., at or near the anus or the vaginal opening) to a second location above the urethral opening (e.g., at or near the clitoris or the pubic hair). The opening 106 can exhibit an elongated shape since the space between the legs of a female wearer is relatively small when the legs of the female wearer are closed, thereby only permitting the flow of the fluids along a path that corresponds to the elongated shape of the opening 106. For example, the opening 106 can extend longitudinally along the fluid impermeable barrier. The opening 106 in the fluid impermeable barrier 102 can exhibit a width that is measured transverse to the longitudinal direction and may be at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 can exhibit a width that is greater than 50% of the circumference of the fluid collection device 100 since a vacuum (e.g., suction) through a conduit 108 pulls the fluid into the conduit 108. In some embodiments, the opening 106 may be vertically oriented (e.g., having a major axis parallel to the longitudinal axis of the device 100). In some embodiments (not shown), the opening 106 may be horizontally oriented (e.g., having a major axis perpendicular to the longitudinal axis of the device 100). In some embodiments, the inward border or edge 129 of the fluid impermeable barrier 102 defines the opening 106. The edge 129 can include two opposing arced portions, the arcs following the outer circumference or periphery of the substantially cylindrical fluid impermeable barrier 102.

The fluid impermeable barrier 102 may also temporarily store the fluids in the chamber 104. As such, the fluid impermeable barrier 102 substantially prevents the fluids from exiting the portions of the chamber 104 that are spaced from the opening 106. The fluid impermeable barrier 102 may be flexible, allowing the fluid collection device 100 to bend or curve when positioned against the body of a wearer. For example, the fluid impermeable barrier 102 can be formed of any suitable fluid impermeable materials, such as a fluid impermeable polymer (e.g., silicone, polypropylene, polyethylene, polyethylene terephthalate, a polycarbonate, etc.), polyurethane films, TPE, oil, another suitable material, or combinations thereof. In some embodiments, the fluid impermeable barrier 102 can include one or more thermoplastic elastomers. The one or more thermoplastic elastomers may be combined with at least one of silicone and oil. In many embodiments, the fluid impermeable barrier 102 can include a composition having at least silicone and oil therein.

The fluid collection device 100 can include a fluid permeable body 120 or layer disposed in the chamber 104. The fluid permeable body 120 can cover or extend across at least a portion (e.g., all) of the opening 106. The fluid permeable body 120 can be configured to wick fluid away from the opening 106, thereby preventing the fluid from escaping the chamber 104. The fluid permeable body 120 also can wick the fluid generally towards an interior of the chamber 104, as discussed in more detail below. A portion of the fluid permeable body 120 can define a portion of an outer surface of the fluid collection device 100. Specifically, the portion of the fluid permeable body 120 defining the portion of the outer surface of the fluid collection device 100 can be the portion of the fluid permeable body 120 exposed by the opening 106 defined by the fluid impermeable barrier 102. At least a portion of the fluid permeable body 120 exposed by the opening 106 may contact the wearer.

The fluid permeable body 120 can include any material that can wick the fluid. The permeable properties referred to herein can be wicking, capillary action, diffusion, or other similar properties or processes, and are referred to herein as "permeable" and/or "wicking." Such "wicking" may exclude absorption into the wicking material (e.g., retention of fluid by the material). Put another way, substantially no absorption of fluid in the material may take place after the material is exposed to the fluid and removed from the fluid for a time. While no absorption is desired, the term "substantially no absorption" may allow for nominal amounts of absorption of fluid into the wicking material (e.g., absorbency), such as less than about 10 wt % of the dry weight of the wicking material, less than about 7 wt %, less than about 5 wt %, less than about 3 wt %, less than about 2 wt %, less than about 1 wt %, or less than about 0.5 wt % of the dry weight of the wicking material.

The fluid permeable body 120 can enable the fluid to flow generally towards a reservoir 122 (shown in FIGS. 2A and 2B) of void space formed within the chamber 104. For example, the fluid permeable body 120 can include a porous or fibrous material, such as spun nylon fibers or a hydrophilic polyolefin. Examples of polyolefin that can be used in the fluid permeable body 120 include, but are not limited to, polyethylene, polypropylene, polyisobutylene, ethylene propylene rubber, ethylene propylene diene monomer, or combinations thereof. In some embodiments, the porous or fibrous material can be extruded into a substantially cylindrically shape to fit within the chamber 104 of the fluid impermeable barrier 102. The fluid permeable body 120 can be manufactured according to various manufacturing methods, such as molding, extrusion, or sintering as will be described in more detail with reference to FIGS. 4-19.

In some embodiments, during use, the fluid permeable body 120 extends from the conduit 108 to interface the fluid impermeable barrier 102 and the opening 106. In some embodiments, a majority of the outer surface 109 (shown in FIG. 1B and FIG. 3) of the fluid permeable body 120 interfaces with an inner surface 103 (shown in FIG. 1B) of the fluid impermeable barrier 102. In other embodiments, a majority of the outer surface 109 may be exposed by the opening 106 of the fluid impermeable barrier 102. In some embodiments, at least a portion of the fluid permeable body 120 extends continuously between the opening 106 and the reservoir 122. In some embodiments, the fluid collection device 100 is free from a seal or cushioning ring on the inward edge 129 defining the opening 106.

Figure 3:
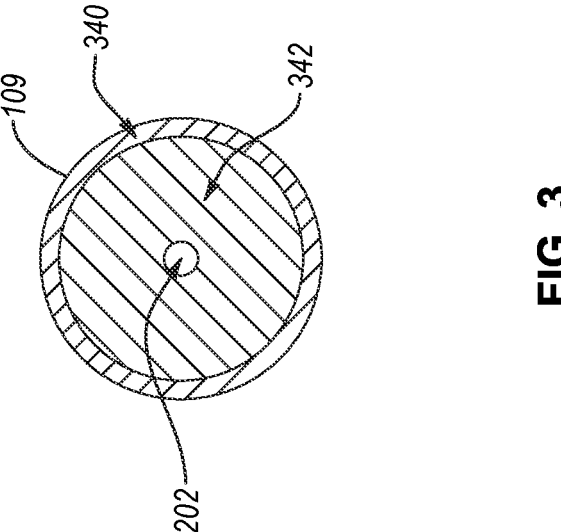
FIG. 3 is a cross-sectional view of the fluid collection device taken along line 3-3 of FIG. 1A according to at least one embodiment of the disclosure.

FIG. 3 is a cross-sectional view of the fluid collection device 100 taken along line 3-3 of FIG. 1A. As shown in FIG. 3, the fluid permeable body 120 can include a fluid permeable membrane 340 covering or wrapped around at least a portion of a fluid permeable support 342, with both the fluid permeable membrane 340 and the fluid permeable support 342 being disposed at least partially in the chamber 104. The fluid permeable membrane 340 can cover or extend across at least a portion (e.g., all) of the opening 106. In some embodiments, at least one of the fluid permeable membrane 340 or the fluid permeable support 342 include nylon configured to wick fluid away from the opening 106. The material of the fluid permeable membrane 340 and the fluid permeable support 342 also can include natural fibers. In such examples, the material may have a coating to prevent or limit absorption of fluid into the material, such as a water repellent (e.g., hydrophobic) coating.

The fluid permeable membrane 340 can include any material that can wick the fluid. For example, the fluid permeable membrane 340 can include fabric, such as a gauze (e.g., a silk, linen, polymer based materials such as polyester, or cotton gauze), another soft fabric (e.g., jersey knit fabric or the like), or another smooth fabric (e.g., rayon, satin, or the like). Forming the fluid permeable membrane 340 from gauze, soft fabric, and/or smooth fabric can improve comfort of the wearer, for example by reducing chaffing of the wearer's skin caused by the fluid collection device 100. In some embodiments, the fluid permeable body 120 includes a fluid permeable support 342 including a porous nylon structure (e.g., spun nylon fibers) and a fluid permeable membrane 340 including gauze.

The fluid permeable body 120 is disposed within a chamber 104 (shown in FIGS. 2A and 2B) of the fluid impermeable barrier 102 of the fluid collection device 100 and is exposed to the urethra of the user 150 through the opening 106 in the fluid collection device 100. Fluids received in the chamber 104 of the fluid collection device 100 from the urethra can be removed through the conduit 108.

Figure 2A:
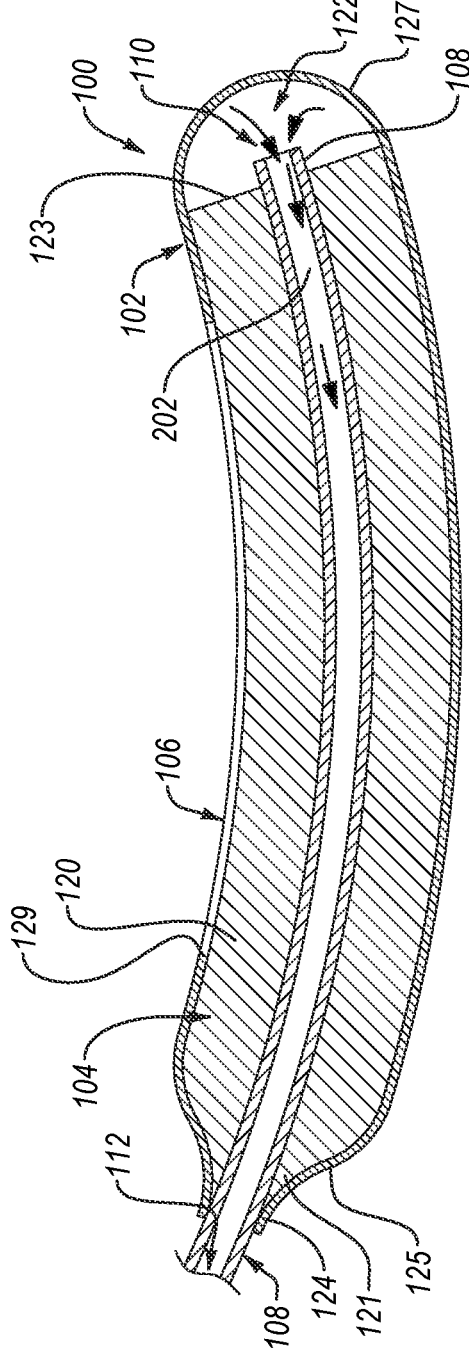
FIGS. 2A and 2B are cross-sectional views of the female fluid collection device of FIG. 1A taken along line 2-2 thereof according to at least one embodiment of the disclosure.
Figure 2B:
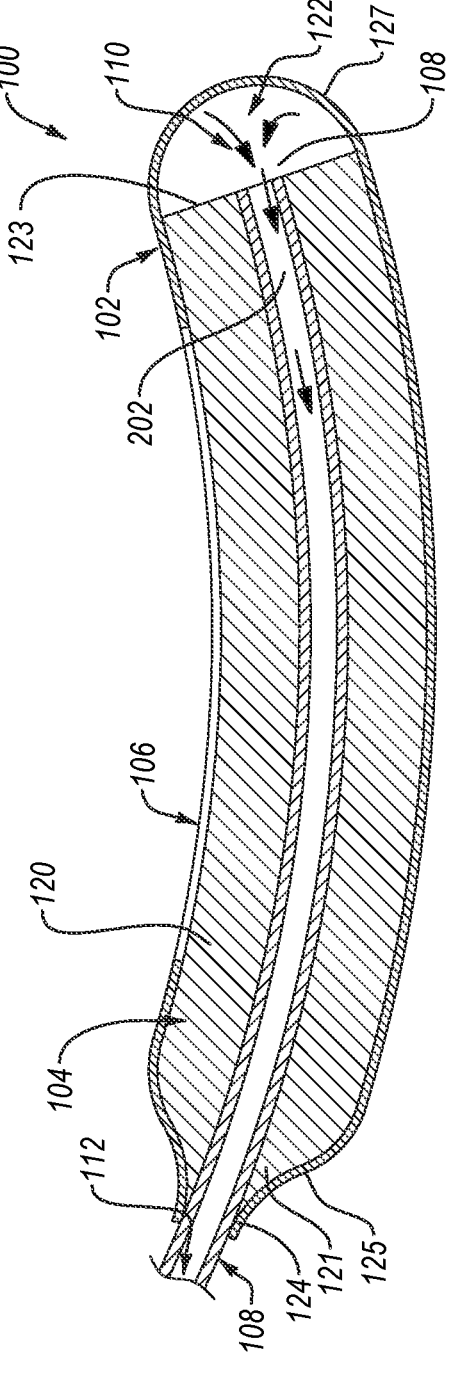

FIG. 2A is a cross-sectional view of the fluid collection device 100 taken along line 2-2 of FIG. IA. The fluid collection device 100 also includes conduit 108 that is at least partially disposed in the chamber 104. The conduit 108 (e.g., a tube) includes an inlet 110 at a second end region 127 of the fluid impermeable barrier 102 and an outlet 112 at a first end region 125 of the fluid impermeable barrier 102 positioned downstream from the inlet 110. The conduit 108 provides fluid communication between an interior region of the chamber 104 and a fluid storage container (not shown) and/or a portable vacuum source (not shown). For example, the conduit 108 may directly or indirectly fluidly couple the interior region of the chamber 104 and/or the reservoir 122 with the fluid storage container or the portable vacuum source.

In the illustrated embodiment, the fluid permeable body 120 defines a bore 202 extending through the fluid permeable body 120 from a first body end 121 of the fluid permeable body 120 to a second body end 123 of the fluid permeable body 120 distal to the first body end 121. In other embodiments, the bore 202 extends only partially into the fluid permeable body from the first body end 121 of the fluid permeable body 120.

In the illustrated embodiment, the conduit 108 is at least partially disposed in the chamber 104 and interfaces at least a portion of the bore 202 of the fluid permeable body 120. For example, the conduit 108 may extend into the fluid impermeable barrier 102 from the first end region 125 (e.g., proximate to the outlet 112) and may extend through the bore 202 to the second end region 127 (e.g., opposite the first end region 125) to a point proximate to a reservoir 122 such that the inlet 110 is in fluid communication with the reservoir 122. For example, in the illustrated embodiment, the inlet 110 is positioned in the reservoir 122. However, in other embodiments such as in FIG. 2B, the inlet 110 may be positioned flush with or behind an end of the fluid permeable body 120 that partially defines the reservoir 122. The fluid collected in the fluid collection device 100 may be removed from the interior region of the chamber 104 via the conduit 108. The conduit 108 may include a flexible material such as plastic tubing (e.g., medical tubing). Such plastic tubing may include a thermoplastic elastomer, polyvinyl chloride (PVC), ethylene vinyl acetate, polytetrafluoroethylene, etc., tubing. In some embodiments, the conduit 108 may include silicone or latex.

The fluid impermeable barrier 102 can store fluids in a reservoir 122 therein. The reservoir 122 is an unoccupied portion of the chamber 104 and is void of other material. In some embodiments, the reservoir 122 is defined at least partially by the fluid permeable body 120 and the fluid impermeable barrier 102. The reservoir 122 may be disposed in any portion of the interior region of the chamber 104. For example, the fluid reservoir 122 may be positioned in the second end region 127 of the chamber 104. In the illustrated embodiment, the reservoir 122 is defined by the second body end 123 of the fluid permeable body 120 and the second end region 127 of the fluid impermeable barrier 102.

In an embodiment, the reservoir 122 can be located at the portion of the chamber 104 that is closest to the inlet 110 (e.g., the second end 127 region). However, the reservoir 122 can be located at different locations in the chamber 104 (e.g., the first end 125 region, a portion of the chamber 104 away from the opening 106). In some embodiments, the conduit 108 may extend through the fluid impermeable barrier to the reservoir 122 without extending through the fluid permeable body 120. Accordingly, in these and other embodiments, the fluid permeable body 120 may be free from the bore 202. In another embodiment, the fluid collection device 100 can include multiple reservoirs, such as a first reservoir that is located at the portion of the chamber of the chamber 104 that is closest to the inlet 110 (e.g., second end region) and a second reservoir that is located at the portion of the of the chamber 104 that is closest to the outlet 112 (e.g., first end region). In another example, the fluid permeable body 120 is spaced from at least a portion of the conduit 108 and the reservoir 122 can be the space between the fluid permeable body 120 and the conduit 108.

The fluid impermeable barrier 102 can define an aperture 124 sized to receive the conduit 108 (e.g., at least one tube). The at least one conduit 108 can be disposed in the chamber 104 via the aperture 124. The apertures 124 can be configured to form an at least substantially fluid tight seal against the conduit 108 or the at least one tube thereby substantially preventing the fluids from escaping the chamber 104.

When secured to the fluid collection device 100, the conduit 108 is configured to provide fluid communication with and at least partially extend between one or more of a fluid storage containers (not shown) and a portable vacuum source (not shown). For example, the conduit 108 may be configured to be fluidly coupled to and at least partially extend between one or more of the fluid storage containers and the portable vacuum source. In an embodiment, the conduit 108 is configured to be directly connected to the portable vacuum source. In such an example, the conduit 108 can extend from the fluid impermeable barrier 102 by at least one foot, at least two feet, at least three feet, or at least six feet. In another example, the conduit 108 is configured to be indirectly connected to at least one of the fluid storage container or the portable vacuum source.

The inlet 110 and the outlet 112 are configured to provide fluid communication (e.g., directly or indirectly) between the portable vacuum source and the chamber 104 (e.g., the reservoir 122). For example, the inlet 110 and the outlet 112 of the conduit 108 may be configured to directly or indirectly fluidly couple the portable vacuum source to the reservoir 122. In an embodiment, the inlet 110 and/or the outlet 112 can form a male connector. In another example, the inlet 110 and/or the outlet 112 can form a female connector. In an embodiment, the inlet 110 and/or the outlet 112 can include ribs that are configured to facilitate secure couplings. In an embodiment, the inlet 110 and/or the outlet 112 can form a tapered shape. In an embodiment, the inlet 110 and/or the outlet 112 can include a rigid or flexible material.

As the portable vacuum source applies a vacuum/suction in the conduit 108, the fluid(s) in the chamber 104 (e.g., such as in the reservoir 122 positioned at the first end region 125, the second end region 127, or other intermediary positions within the chamber 104) may be drawn into the inlet 110 and out of the fluid collection device 100 via the conduit 108.

In an embodiment, the conduit 108 is configured to be at least insertable into the chamber 104. In such an embodiment, the conduit 108 can include one or more markers 131

(shown in FIG. 1A) on an exterior thereof that are configured to facilitate insertion of the conduit 108 into the chamber 104. For example, the conduit 108 can include one or more markings thereon that are configured to prevent over or under insertion of the conduit 108, such as when the conduit 108 defines an inlet 110 that is configured to be disposed in or adjacent to the reservoir 122. In another embodiment, the conduit 108 can include one or more markings thereon that are configured to facilitate correct rotation of the conduit 108 relative to the chamber 104. In an embodiment, the one or more markings can include a line, a dot, a sticker, or any other suitable marking. In examples, the conduit 108 may extend into the fluid impermeable barrier 102 from the first end 125 region (e.g., proximate to the outlet 112) and may extend to the second end 127 region (e.g., opposite the first end region) to a point proximate to the reservoir 122 such that the inlet 110 is in fluid communication with the reservoir 122. In some embodiments (not shown), the conduit 108 may enter the second end 127 region and the inlet 110 may be disposed in the second end 127 region (e.g., in the reservoir 122). The fluid collected in the fluid collection device 100 may be removed from the interior region of the chamber 104 via the conduit 108. The conduit 108 may include a flexible material such as plastic tubing (e.g., medical tubing) as disclosed herein. In some examples, the conduit 108 may include one or more portions that are resilient, such as to by having one or more of a diameter or wall thickness that allows the conduit to be flexible.

As disclosed herein, embodiments of fluid collection devices and components thereof may be manufactured by a variety of methods. For example, the fluid collection device 100 including the fluid impermeable barrier 102 and the fluid permeable body 120 may be manufactured by a variety of methods. Certain manufacturing methods may automate one or more fabrication and/or assembly steps. In some applications, this may increase consistency, reduce time, and/or improve sterility. Certain manufacturing methods may reduce or eliminate one or more components of the fluid collection device (e.g., the fluid permeable membrane 140 of the fluid permeable body 120). In some applications, this may reduce cost, permit additional automation, and/or reduce time of manufacture. Certain manufacturing methods may add components to the fluid collection device. In some applications, this may make the fluid collection device easier to assemble, couple to a vacuum source and/or external fluid collection reservoir, and/or otherwise put into use. Certain manufacturing methods may alter a shape, arrangement, and/or configuration of one or more components of the fluid collection device. In some applications, this may permit additional automation in manufacturing, reduce cost, improve performance of the fluid collection device, and/or make the fluid collection device easier to assemble or put in use.

Various manufacturing methods of fluid collection devices and components thereof will now be described in more detail with reference to FIGS. 4-19.

FIGS. 4A-4D illustrate the operation of a tube cutting apparatus according to at least one embodiment of the disclosure. In some embodiments, the tube cutting apparatus 400 may be used to reduce or eliminate manual cutting of tubing used for a conduit of a fluid collection device, such as conduit 108. In some embodiments, the tube cutting apparatus 400 may be used to reduce or eliminate manual cutting of a tube of fluid wicking material for a fluid permeable body, such as fluid permeable membrane 340 and/or support 342 of fluid permeable body 120.

The tube cutting apparatus 400 may include a reel 402 around which is wrapped a length of tubing 404. In some embodiments, the tubing 404 may be tubing associated with a conduit of a fluid collection device, a fluid permeable membrane of the fluid collection device, and/or a support of the fluid collection device. The tube cutting apparatus 400 may further include a set of motorized rollers 406 and a second set of motorized rollers 408. The sets of motorized rollers 406, 408 may be mounted to a housing 424. In some embodiments, the housing 424 may include motors for rotating the motorized rollers 406, 408. The tube cutting apparatus 400 may further include a stop 410 mounted to the housing 424. The motorized rollers 406, 408 may include metal, plastic, or a combination thereof. For example, the motorized rollers 406, 408 may include metal with a plastic non-slip coating to prevent the tubing 404 from slipping between the motorized rollers 406, 408.

Figures 4A, 4B, 4C, 4D:
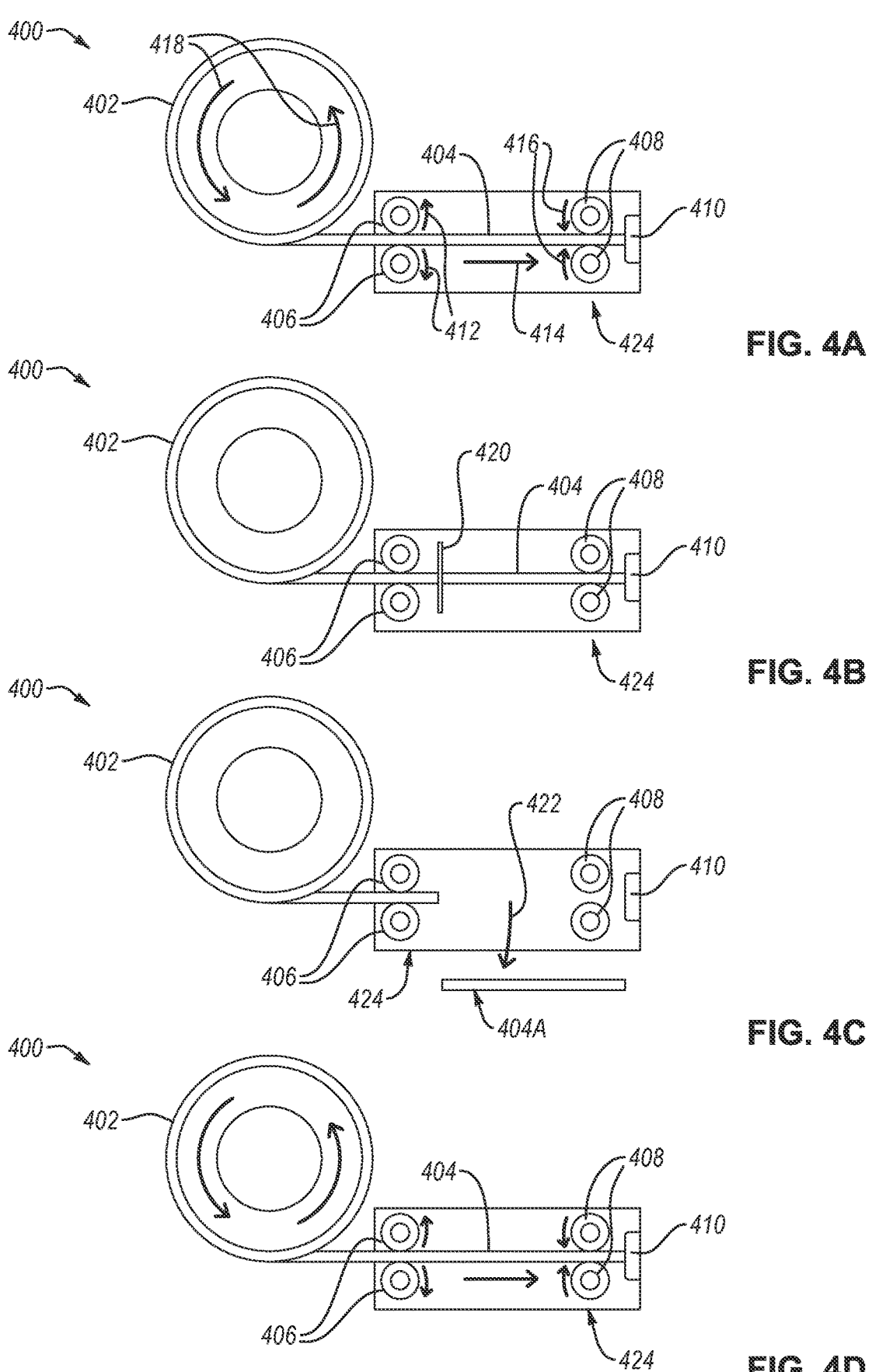
FIGS. 4A-4D illustrate the operation of a tube cutting apparatus according to at least one embodiment of the disclosure.

As shown in FIG. 4A, the motorized rollers 406 may rotate in opposing directions as indicated by arrows 412 to draw the tubing 404 off the reel 402 and between the motorized rollers 406. The tubing 404 may be drawn along a direction indicated by arrow 414 to the motorized rollers 408. The motorized rollers 408 may rotate in opposing directions as indicated by arrows 416 to draw the tubing 404 between the motorized rollers 408 to the stop 410. In some embodiments, the movement of the motorized rollers 406, 408 may cause the reel 402 to rotate as indicated by arrows 418. In other embodiments, the reel 402 may also be motorized.

In some embodiments, the stop 410 includes a sensor that detects when the tubing 404 contacts the stop 410. Examples of suitable sensors include, but are not limited to, a spring switch, pressure pad, optical detector). In some embodiments, the motorized rollers 406 and/or 408 may include torque sensors. The torque may increase when the tubing 404 contacts the stop 410. When the sensor of the stop 410 and/or the torque sensors indicate the tubing 404 is in contact with the stop 410, the motorized rollers 406, 408 may stop rotating.

The tube cutting apparatus 400 may further include a blade (e.g., sharp edge) 420 as shown in FIG. 4B. The blade 420 may cut the tubing 404 to length. The location of the blade 420 may be based, at least in part, on a desired length of a cut tube. In some embodiments, the position of the blade 420 may be adjustable. In some embodiments, the blade 420 may include metal, a ceramic, and/or a combination thereof. In some embodiments, the blade 420 may be replaced by an alternative cutting element such as a laser, ultrasonic cutter, electric arc, etc. As shown in FIG. 4C, the cut tubing 404A may be removed from the tube cutting apparatus 400. In some embodiments, the cut tubing 404A may be placed in a collection container (not shown). In some embodiments, the cut tubing 404A may fall as indicated by arrow 422, due to gravity. In other embodiments, the cut tubing 404A may be ejected from the tube cutting apparatus 400, for example, by a piston (not shown). In some embodiments, the cut tubing 404A may be manually removed from the tube cutting apparatus 400 by a user. Once the cut tubing 404A is removed from the tube cutting apparatus 400, the next length of tubing 404 can be drawn through the motorized rollers 406, 408 to the stop 410 as shown in FIG. 4D.

In some embodiments, the housing 424 may further include a processor and/or other circuitry for controlling the various components of the tube cutting apparatus 400. For example, the speed of the motorized rollers 406, 408, stopping the motorized rollers 406,408 responsive to the tubing 404 contacting the stop 410, and actuating the blade 420. In some embodiments, the operation of the tube cutting apparatus 400 illustrated in FIGS. 4A-4D is completely automated. In other embodiments, some or all of the actions may be initiated by a user by actuating one or more buttons, switches, foot pedals, etc. For example, the user may push a foot pedal to actuate the blade 420 whereas the actions of the motorized rollers 406,408 may be automated. In some embodiments, the tube cutting apparatus 400 may further include a graphical user interface (e.g., a touch screen, a conventional screen in combination with a keypad and/or trackpad) for the user to initiate some or all of the actions and/or configure the tube cutting apparatus 400 for fully automated operation. For example, a user may set a speed of the motorized rollers 406, 408, a distance between rollers of a set of the motorized rollers 406, 408, and/or a location of the blade 420 between the two sets of motorized rollers 406, 408.

Figure 5:
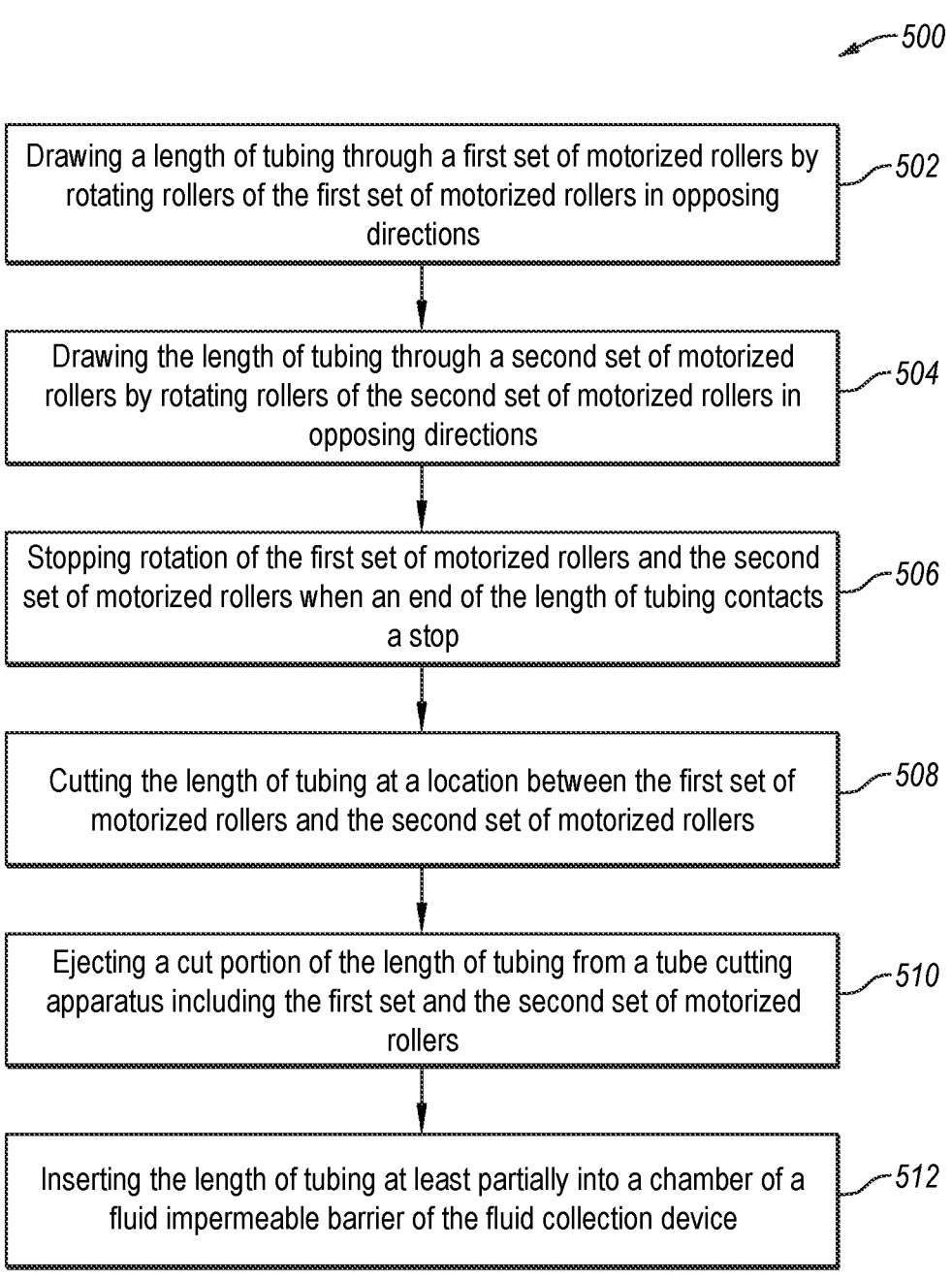
FIG. 5 is a flow chart of a method according to at least one embodiment of the disclosure.

FIG. 5 is a flow chart of a method according to at least one embodiment of the disclosure. The method 500 may be performed, at least in part, by a tube cutting apparatus, such as tube cutting apparatus 400 in some embodiments. The method 500 may be used to manufacture at least a portion of a fluid collection device disclosed herein, for example, fluid collection device 100.

At block 502, "drawing a length of tubing through a first set of motorized rollers by rotating rollers of the first set of motorized rollers in opposing directions" may be performed. At block 504, "drawing the length of tubing through a second set of motorized rollers by rotating rollers of the second set of motorized rollers in opposing directions" may be performed. In some embodiments, blocks 502 and 504 may be performed simultaneously. In some embodiments, block 502 may be initiated first and continue while block 504 is initiated. 6. In some embodiments, the length of tubing comprises a fluid impermeable tubing. In some embodiments, the fluid impermeable tubing comprises polyvinyl chloride. In some embodiments, the length of tubing comprises a fluid permeable material. In some embodiments, the fluid permeable material comprises an open cell foam.

At block 506, "stopping rotation of the first set of motorized rollers and the second set of motorized rollers when an end of the length of tubing contacts a stop" may be performed. In some embodiments, when the end of the length of tubing contacts the stop may be detected with a sensor included with the stop. In some embodiments, when the end of the length of tubing contacts the stop may be detected when a torque on at least one of the first set of motorized rollers or the second set of motorized rollers increases.

At block 508, "cutting the length of tubing at a location between the first set of motorized rollers and the second set of motorized rollers" may be performed. In some embodiments cutting the tubing may include actuating a blade, such as blade 420. In other embodiments, cutting the tubing may include activating a laser, an ultrasound cutter, and/or other cutting implement.

At block 510, "ejecting a cut portion of the length of tubing from a tube cutting apparatus including the first set and the second set of motorized rollers" may be performed. In some embodiments, ejecting the cut portion of the length of tubing may include actuating a piston.

At block 512, "inserting the length of tubing at least partially into a chamber of a fluid impermeable barrier of the fluid collection device" may be performed. For example, the tubing may inserted into chamber 104 of fluid collection device 100.

FIGS. 6A-6D illustrate the operation of a tube cutting apparatus according to at least one embodiment of the disclosure. In some embodiments, the tube cutting apparatus 600 may be used to reduce or eliminate manual cutting of tubing used for a conduit of a fluid collection device, such as conduit 108. In some embodiments, the tube cutting apparatus 600 may be used to reduce or eliminate manual cutting of a tube of fluid wicking material for a fluid permeable body, such as fluid permeable membrane 340 and/or support 342 of fluid permeable body 120. In some embodiments, the tube cutting apparatus 600 may be used to reduce manual insertion of the conduit into the fluid permeable body.

The tube cutting apparatus 600 may include a reel 602 around which is wrapped a length of tubing 604. In some embodiments, the tubing 604 may be tubing associated with a conduit of a fluid collection device, which may include a fluid impermeable material. The tube cutting apparatus 600 may include one or more sets of motorized rollers 606. The sets of motorized rollers 606 may be mounted to a housing (not shown), similar to housing 424 in FIGS. 4A-D. The tube cutting apparatus may include another reel 608 around which is wrapped another length of tubing 610. The tubing 610 may be tubing associated with a fluid permeable body of the fluid collection device. For example, the tubing 610 may be used to implement the support and/or fluid permeable membrane of the fluid permeable body. The tube cutting apparatus 600 may include one or more additional sets of motorized rollers 612. The motorized rollers 606, 612 may include metal, plastic, or a combination thereof. For example, the motorized rollers 606, 612 may include metal with a plastic non-slip coating to prevent the tubing 604, 610 from slipping between the motorized rollers 606, 612.

The tube cutting apparatus 600 may include a housing 614 which may have an opening 620 at a first end 622 (indicated in FIG. 6B) sized to accept the tubing 604 therein and an opening 624 at a second end 626 opposite the first end 622 sized to accept the tubing 610. In some embodiments, the opening 624 may be larger than the opening 620. The housing 614 may further include a stop 616 (indicated in FIG. 6A). In some embodiments, the stop 616 may be a ledge formed by the opening 620 meeting the opening 624 when opening 620 is smaller than opening 624.

Figures 6A, 6B, 6C, 6D:
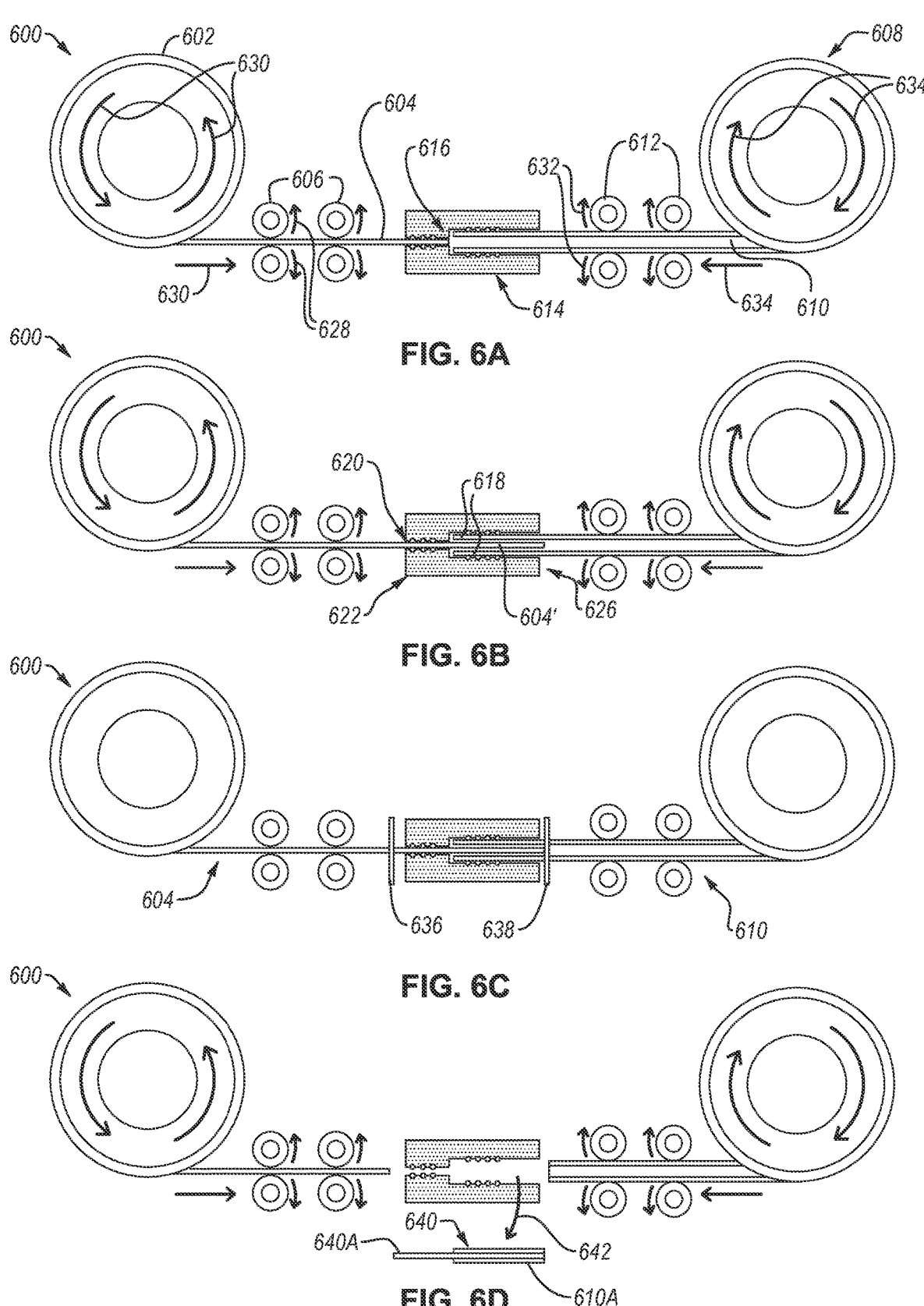
FIGS. 6A-6D illustrate the operation of a tube cutting apparatus according to at least one embodiment of the disclosure.

As shown in FIG. 6A, the motorized rollers 606 may rotate in opposing directions as indicated by arrows 628 to draw the tubing 604 off the reel 602 and between the motorized rollers 606. The tubing 604 may be drawn along a direction indicated by arrow 630 through the opening 620 of the housing 614. In some embodiments, the movement of the motorized rollers 606 may cause the reel 602 to rotate as indicated by arrows 630. In other embodiments, the reel 602 may also be motorized.

The motorized rollers 612 may rotate in opposing directions as indicated by arrows 632 to draw the tubing 610 between the motorized rollers 612 through the opening 624 of the housing 614 to the stop 616. In some embodiments, the movement of the motorized rollers 612 may cause the reel 608 to rotate as indicated by arrows 634. In other embodiments, the reel 608 may also be motorized.

In some embodiments, the stop 616 may include a sensor that detects when the tubing 610 contacts the stop 616. Examples of suitable sensors include, but are not limited to, a spring switch, pressure pad, optical detector). In some embodiments, the housing 614 may include sensors 618 (indicated in FIG. 6B) along the opening 624 to detect the tubing 610. In some embodiments, the motorized rollers 612 may include torque sensors. The torque may increase when the tubing 610 contacts the stop 616. When the sensor of the stop 616, sensors 618, and/or the torque sensors indicate the tubing 610 is in contact with the stop 616, the motorized rollers 612 may stop rotating.

As shown in FIG. 6B, the motorized rollers 606 may continue to rotate until a portion (e.g., length) of the tubing 604 (tubing 604') is inserted through the tubing 610. Thus, the tubing 610 may include a bore (e.g., similar to bore 202) sized to accept the tubing 604 therein. In some embodiments, the motorized rollers 606 may include encoders that detect when a desired length of the tubing 604 has been inserted into the tubing 610. In some embodiments, the sensors 618 may detect when the desired length of the tubing 604 has been inserted into the tubing 610. When the encoders and/or sensors 618 indicate the desired length of tubing 604 has been inserted into the tubing 610, the motorized rollers 606 may stop rotating.

The tube cutting apparatus 600 may include a blade (e.g., sharp edge) 636 as shown in FIG. 6C. The blade 636 may cut the tubing 604 to a desired length. The length may be such that the tubing 604 extends a distance outside the tubing 610. The location of the blade 636 may be based, at least in part, on a desired length of the tubing 604. The tube cutting apparatus 600 may include a blade 638 for cutting the tubing 610. In some embodiments, the blade 638 may be positioned to cut the tubing 610 flush with the portion of tubing 604'. In some embodiments, the blade 638 may be positioned such that tubing 610 extends beyond the portion of tubing 604'. In some embodiments, the position of the blade 636 and/or 638 may be adjustable. In some embodiments, the blade 636 and/or 638 may include metal, a ceramic, and/or a combination thereof. In some embodiments, the blade 636 and/or 638 may be replaced by an alternative cutting element such as a laser, ultrasonic cutter, electric arc, etc. In some embodiments, the tube cutting apparatus 600 may include a single blade that changes position to cut both tubes.

As shown in FIG. 6D, the cut tubing 640 may be removed from the tube cutting apparatus 600. In some embodiments, the cut tubing 640, including tube 604A and tube 610A, may be placed in a collection container (not shown). In some embodiments, the cut tubing 640 may fall as indicated by arrow 642, due to gravity. In other embodiments, the cut tubing 640 may be ejected from the tube cutting apparatus 600, for example, by a piston (not shown). In some embodiments, the cut tubing 640 may be manually removed from the tube cutting apparatus 600 by a user. In some embodiments, the cut tubing 640 may be inserted into a fluid impermeable barrier of a fluid collection device. For example, the cut tubing 640 may be inserted into a chamber (e.g., chamber 104) through an opening (e.g., opening 106) of the fluid impermeable barrier such that the tubing 604 pass through an aperture at an end of the chamber (e.g., aperture 124) and the tubing 610 substantially fills the opening of the chamber.

Similar to the tube cutting apparatus 400, in some embodiments, tube cutting apparatus 600 may further include a processor and/or other circuitry for controlling the various components of the tube cutting apparatus 600. For example, the speed of the motorized rollers 606, 612, stopping the motorized rollers 606, 612 responsive to the tubing 610 contacting the stop 616, and actuating the blades 636, 638. In some embodiments, the operation of the tube cutting apparatus 600 illustrated in FIGS. 6A-4D is completely automated. In other embodiments, some or all of the actions may be initiated by a user by actuating one or more buttons, switches, foot pedals, etc. For example, the user may push a foot pedal to actuate the blades 636, 638 whereas the actions of the motorized rollers 606, 612 may be automated. In some embodiments, the tube cutting apparatus

600 may further include a graphical user interface (e.g., a touch screen, a conventional screen in combination with a keypad and/or trackpad) for the user to initiate some or all of the actions and/or configure the tube cutting apparatus 600 for fully automated operation. For example, a user may set a speed of the motorized rollers 606, 612, a distance between rollers of a set of the motorized rollers 606, 612, and/or locations of the blades 636, 638.

FIG. 7 is a flow chart of a method according to at least one embodiment of the disclosure. The method 700 may be performed, at least in part, by a tube cutting apparatus, such as tube cutting apparatus 600 in some embodiments. The method 700 may be used to manufacture at least a portion of a fluid collection device disclosed herein, for example, fluid collection device 100.

At block 702, "drawing a first tube into a tube cutting apparatus from a first direction by rotating a first set of motorized rollers in opposing directions until the first tube contacts a stop" may be performed. In some embodiments, the first tube may include a fluid permeable material such as an open cell foam.

At block 704, "drawing a second tube into the tube cutting apparatus from a second direction by rotating a second set of motorized rollers in opposing directions, wherein drawing the second tube into the tube cutting apparatus causes at least a portion of the second tube to be inserted into the first tube" may be performed. In some embodiments, the second tube may include a fluid impermeable material such as PVC.

At block 706, "stopping drawing the second tube when a length of the second tube is inserted into the first tube" may be performed. In some embodiments, stopping is responsive to determining, with encoders of the second set of motorized rollers, the length of the second tube is inserted into the first tube.

At block 708, "cutting the first tube and the second tube" may be performed. In some embodiments, the first tube is cut with a first blade and the second tube is cut with a second blade. In other embodiments, a blade movable between two locations may be used to cut the first and second tubes. In some embodiments, other cutting implements may be used (e.g., lasers, ultrasound, thermal cutters).

At block 710, "ejecting a cut portion of the first tube and the second tube from the tube cutting apparatus" may be performed. In some embodiments, the cut portion may be ejected by actuating a piston. In some embodiments, the cut portion may be accepted in a collection container.

At block 712, "inserting the cut portion of the first tube and the second tube at least partially into a chamber of a fluid impermeable barrier of the fluid collection device" may be performed. For example, the cut portion of the first and second tubes may inserted into chamber 104 of fluid collection device 100.

Returning to FIG. 3, the fluid permeable body 120 is shown including the fluid permeable membrane 340 completely surrounding a perimeter of the support 342. However, in some applications, the fluid permeable membrane 340 may not provide a significant contribution to the wicking performance of the fluid permeable body 120. Rather, the fluid permeable membrane 340 may be provided primarily to increase comfort to a wearer (e.g., provide a less abrasive, smoother surface against the wearer's skin). According, the fluid permeable membrane 340 may not need to completely surround the support 342. Rather, only a portion of the fluid permeable body 120 in contact with a wearer's skin.

Figure 8B:
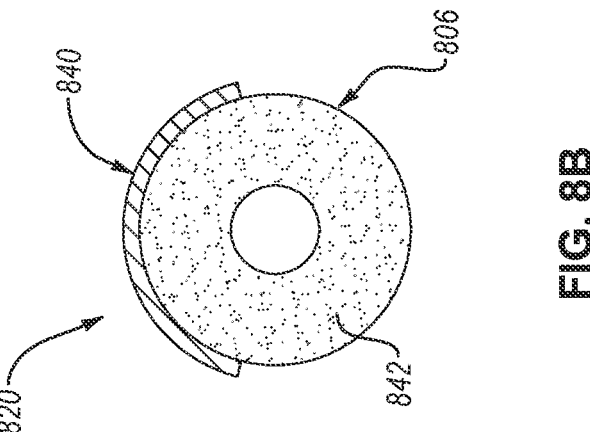
FIG. 8B is a cross-sectional view of the tube of fluid permeable body 820 along the line 8-8 in FIG. 8A.
Figure 8A:
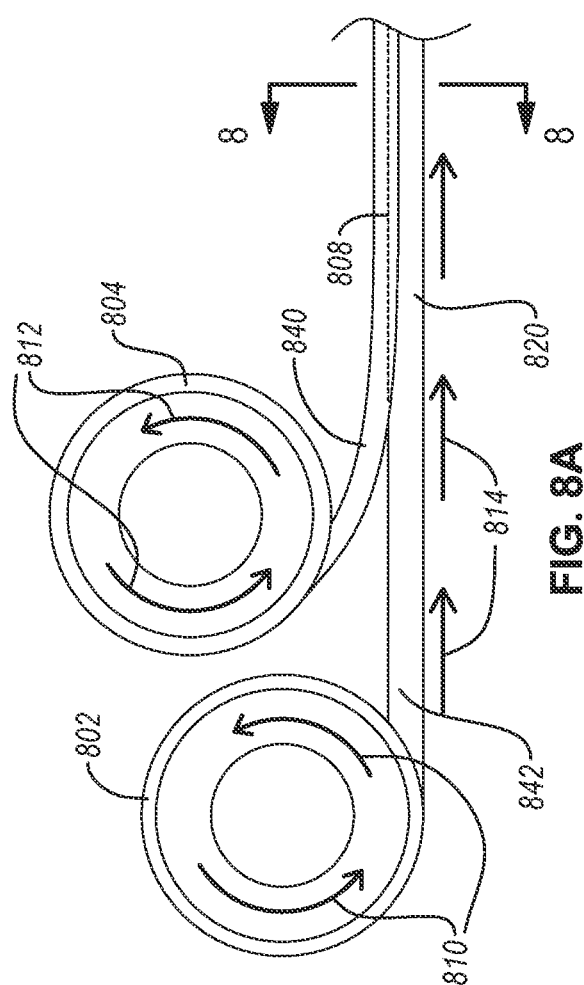
FIG. 8A illustrates a process for manufacturing a fluid permeable body according to at least one embodiment of the disclosure.

FIG. 8A illustrates a process for manufacturing a fluid permeable body according to at least one embodiment of the disclosure. A reel 802 may include a tubing 842 that may be used to implement a support of a fluid permeable body of a fluid collection device (e.g., fluid permeable body 120 of fluid collection device 100). In some embodiments, the tubing 842 may include an open cell foam. A reel 804 may include a strip of material 840 that may be used to implement a fluid permeable membrane. In some embodiments, the strip of material 840 may include a non-woven material and/or a compression bandage.

The reels 802 and 804 may rotate as indicated by arrows 810 and 812, respectively, as the tubing 842 and the strip of material 840 are drawn off the reels 802 and 804, respectively, in a direction indicated by arrows 814. In some embodiments, the tubing 842 and material 840 may be drawn by motorized rollers (not shown) similar to motorized rollers 406, 408, 606, and/or 612. The reels 802 and 804 may be arranged such that as the tubing 842 and strip of material 840 are drawn, the strip of material 840 is positioned upon a portion of an outer perimeter 806 of the tubing 842 (indicated in FIG. 8B). When the strip of material 840 is positioned on the tubing 842, the strip of material 840 may be coupled (e.g., secured) to the tubing 842 to form a tube of fluid permeable body 820. In the embodiment shown in FIG. 8A, the strip of material 840 is coupled to the tubing 842 by stitches 808. However, additional or other coupling methods may be used such as applying an adhesive between the tubing 842 and the strip of material 840, and/or melting a portion of the tubing 842 and/or strip of material 840 such that the two are bonded together. Once the tube of fluid permeable body 820 has been formed, the tube may be cut to a desired length (not shown). For example, the tube of fluid permeable body 820 may be drawn into a tube cutting apparatus, such as tube cutting apparatus 400 and/or tube cutting apparatus 600.

FIG. 8B is a cross-sectional view of the tube of fluid permeable body 820 along the line 8-8 in FIG. 8A. The strip of material 840 only covers a portion of the perimeter 806 of the tubing 842. In the embodiment shown, the strip of material 840 covers approximately one third of the perimeter 806. However, in other embodiments, the strip of material may cover a larger or smaller portion of the perimeter 806. The portion of the perimeter 806 covered may be based, at least in part, on a size of an opening of a fluid impermeable barrier of the fluid collection device (e.g., opening 106 of fluid impermeable barrier 102). The portion of the perimeter 806 of the tubing 842 covered by the strip of material 840 may be selected such that the entire portion of the fluid permeable body 820 exposed by the opening of the fluid impermeable barrier is covered by the strip of material 840.

Figure 9:
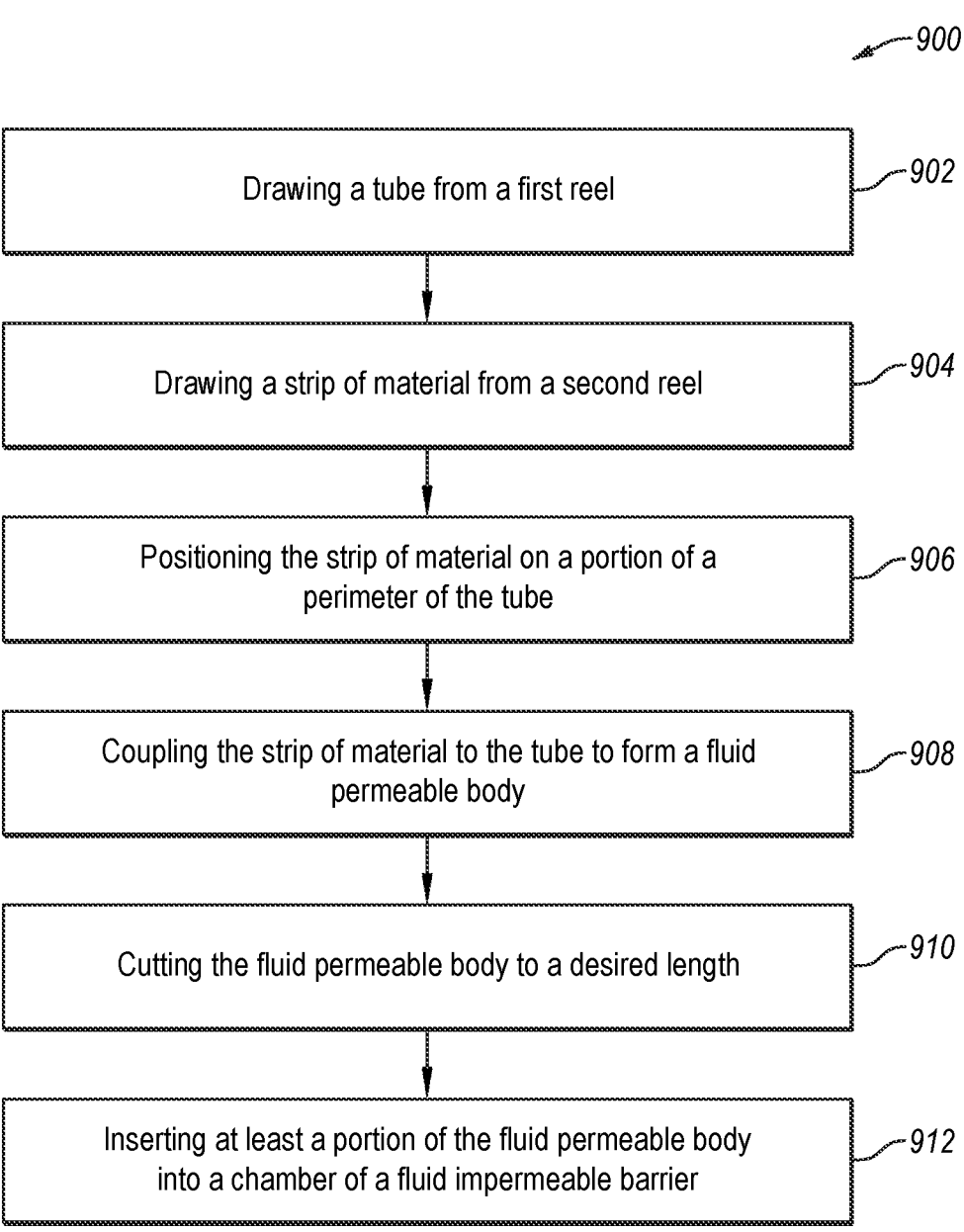
FIG. 9 is a flow chart of a method according to at least one embodiment of the disclosure.

FIG. 9 is a flow chart of a method according to at least one embodiment of the disclosure. In some embodiments, the method 900 may be used to couple a tube to a strip of material, such as tube 842 and strip of material 840.

At block 902 "drawing a tube from a first reel" may be performed. For example, tube 842 may be drawn from reel 802 in some embodiments. In some embodiments, the tube is drawn from the first reel by a set of motorized rollers.

At block 904 "drawing a strip of material from a second reel" may be performed. For example, strip of material 840 may be drawn from reel 804 in some embodiments. In some embodiments, the strip of material may be drawn from the second reel by a set of motorized rollers. In some embodiments, the set of motorized rollers may be the same set of motorized rollers to draw the tube from the first reel. In some embodiments, blocks 902 and 904 may be performed simultaneously or near simultaneously. In some embodiments, block 902 may be initiated first and continue when block 904 is initiated.

At block 906 "positioning the strip of material on a portion of a perimeter of the tube" may be performed. In some embodiments, the positioning may be achieved by the arrangement of the first and second reels. In other embodiments, additional reels, motorized rollers, slots, etc. may be used as guides to position the strip of material and/or tubing.

At block 908 "coupling the strip of material to the tube to form a fluid permeable body" may be performed. In some embodiments, coupling may be achieved by stitching the strip of material to the tube. In some embodiments, coupling may be achieved by applying an adhesive between the tube and the strip of material. In some embodiments, both stitching and adhesive may be used.

At block 910, "cutting the tube of fluid permeable body to a desired length" may be performed.

At block 912, "inserting at least a portion of the fluid permeable body into a chamber of a fluid impermeable barrier" may be performed. For example, the fluid permeable body may be inserted into a chamber of fluid impermeable barrier 102 of fluid collection device 100.

Figure 10B:
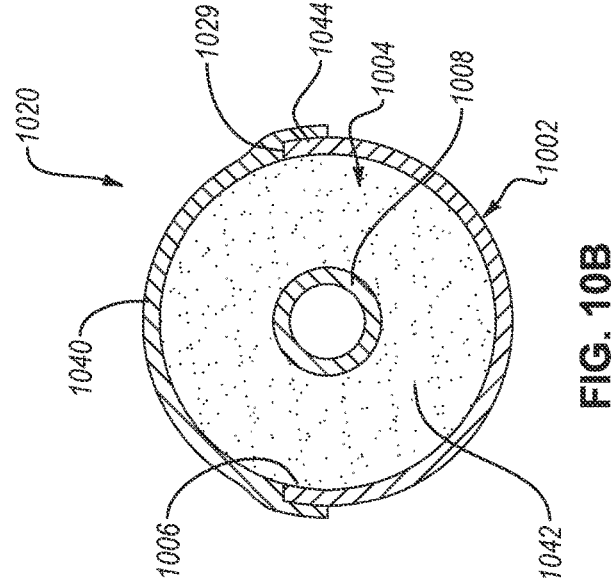
FIG. 10B is a cross-sectional view of the fluid collection device along line A-A shown in FIG. 10A.
Figure 10A:
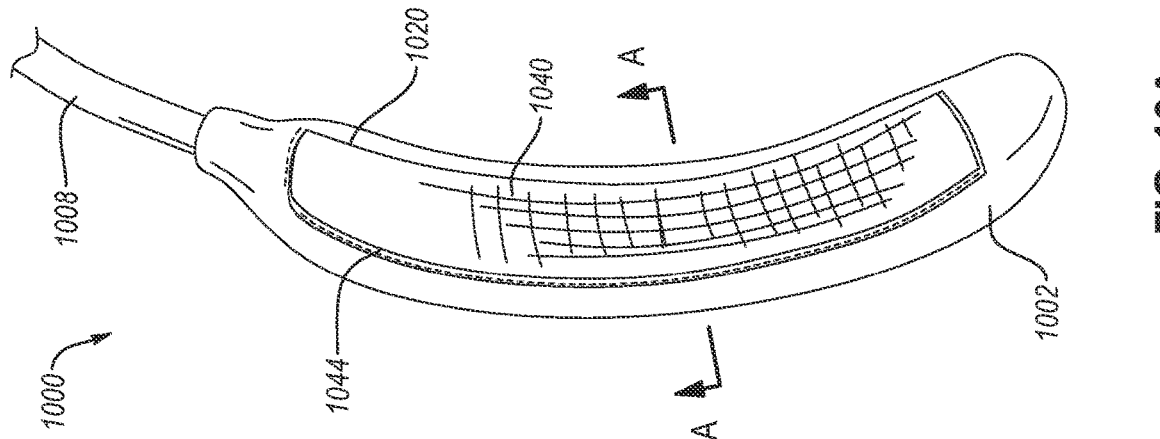
FIG. 10A is a view of a fluid collection device according to at least one embodiment of the disclosure.

FIG. 10A is a view of a fluid collection device according to at least one embodiment of the disclosure. The fluid collection device 1000 may include a fluid impermeable barrier 1002, a fluid permeable body 1020, and a conduit 1008. In some embodiments, the fluid impermeable barrier 1002 may be substantially the same as fluid impermeable barrier 102 and the conduit 1008 may be substantially the same as conduit 108.

The fluid permeable body 1020 may include a support 1042, which may be substantially the same as support 342. The fluid permeable body 1020 may also include a fluid permeable membrane 1040. Similar to the embodiment shown in FIGS. 8A-B, the fluid permeable membrane 1040 may only cover a portion of the support 1042. However, instead of coupling the fluid permeable membrane 1040 to the support 1042, the fluid permeable membrane 1040 may be coupled to the fluid impermeable barrier 1002 along a perimeter 1044 proximate to an opening 1006 of a chamber 1004 within the fluid impermeable barrier 1002 (Indicated in FIG. 10B). In the embodiment shown in FIG. 10A, the fluid permeable membrane 1040 is stitched to the fluid impermeable barrier 1002. However, in other embodiments, the fluid permeable membrane 1040 may be glued, thermally coupled, and/or ultrasonically welded to the fluid impermeable barrier 1002 instead of or in addition to stitching.

FIG. 10B is a cross-sectional view of the fluid collection device along line A-A shown in FIG. 10A. In the embodiment shown, the fluid permeable membrane 1040 extends beyond and edge 1029 of the opening 106 to be coupled at the perimeter 1044. However, in other embodiments, the fluid permeable membrane 1040 may only extend to and be coupled at the edge 1029.

The embodiments shown in FIGS. 9-10 may use less materials and/or simplify manufacturing since the support is only partially covered by the fluid permeable membrane.

Figure 11:
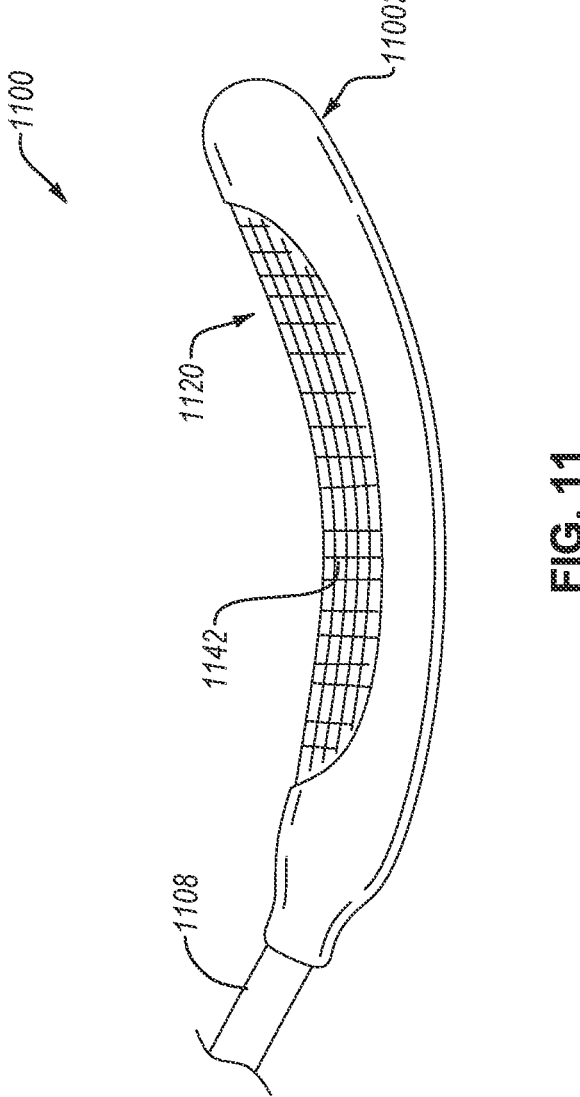
FIG. 11 is a view of a fluid collection device according to at least one embodiment of the disclosure.

FIG. 11 is a view of a fluid collection device according to at least one embodiment of the disclosure. The fluid collection device 1100 may include a fluid impermeable barrier 1102, a fluid permeable body 1120, and a conduit 1108. In some embodiments, the fluid impermeable barrier 1102 may be substantially the same as fluid impermeable barrier 102 and the conduit 1108 may be substantially the same as conduit 108.

The fluid permeable body 1120 may include a support 1142, which may be similar to the same as support 342. However, in some embodiments, the support 1142 may include an open cell polyethylene (PE) foam. In some embodiments, the open cell PE foam may be formed by extrusion. The open cell PE foam may be soft and/or smooth enough at a surface such that a fluid permeable membrane is not necessary to provide comfort to a wearer. Accordingly, in some embodiments, the fluid permeable body 1120 may not include a fluid permeable membrane. Thus, the embodiment shown in FIG. 11, may further reduce materials and manufacturing steps as no fluid permeable membrane needs to be coupled to the support and/or fluid impermeable barrier of the fluid collection device.

Figure 12:
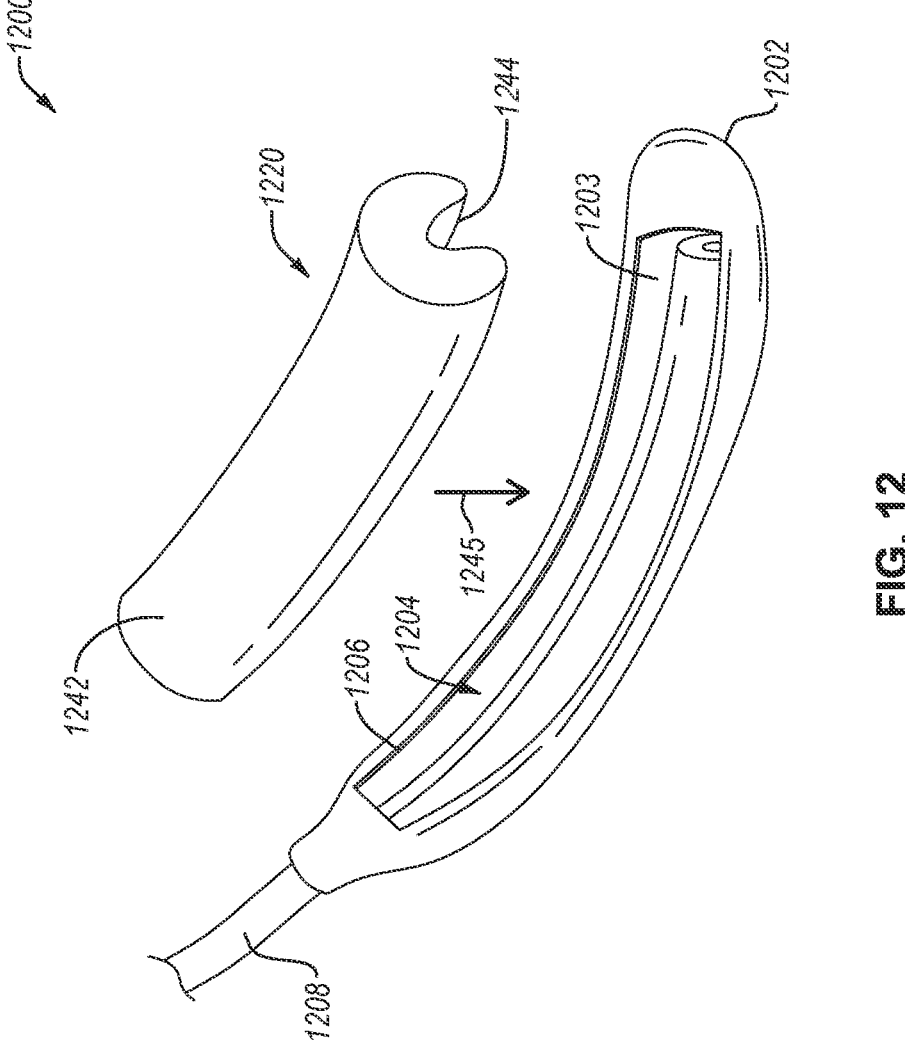
FIG. 12 is a view of a fluid collection device according to at least one embodiment of the disclosure.

FIG. 12 is a view of a fluid collection device according to at least one embodiment of the disclosure. The fluid collection device 1200 may include a fluid impermeable barrier 1202, a fluid permeable body 1220, and a conduit 1208. In some embodiments, the fluid impermeable barrier 1202 may be substantially the same as fluid impermeable barrier 102 and the conduit 1208 may be substantially the same as conduit 108.

In some embodiments, the fluid permeable body 1220 may include a support 1242 which may be configured to wick fluid away from an opening 1206 of the fluid impermeable barrier 1202, similar to support 342. However, instead of defining a bore 202 like support 342, the support 1242 may define a channel 1244 extending from an outer surface 1209 of the fluid permeable body 1220 toward an interior 1211 of the fluid permeable body 1220 along a long axis of the fluid permeable body 1220. The channel 1240 may be configured to at least partially enclose the conduit 1208. Thus, instead of passing through a central portion of the fluid permeable body 1220, for example as shown in the embodiments of FIGS. 1-3, the conduit 1208 may extend through the channel 1244 along an inner surface 1203 of the fluid impermeable barrier 1202 opposite the opening 1206. In some embodiments, the conduit 1208 may be adhered (e.g., adhesive, sonic welding, or a combination thereof) to the inner surface 1203 of the fluid impermeable barrier 1202 to keep it in place. In some embodiments, such as the one shown in FIGS. 13B-D, the fluid impermeable barrier 1202 may include a channel into which the conduit 1208 may be friction or snap-fit to hold the conduit 1208 in place.

The fluid collection device 1200 may be assembled by pressing the fluid permeable body 1220 through the opening 1206 into the chamber 1204 of the fluid impermeable barrier 1202 as indicated by arrow 1245. This may eliminate having to insert the conduit 1208 through a bore of the fluid permeable body 1220. In some embodiments, the fluid permeable body 1220 may extend a length greater than a length of the opening 1206 and/or extend a width greater than a width of the opening 1206. In some embodiments, the fluid impermeable barrier 1202 may include a flexible and/or deformable material that permits the opening 1206 to temporarily widen and/or lengthen in order to accept the fluid permeable body 1220 at least partially into the chamber 1204.

In some embodiments, the support 1242 may include an extruded open cell PE foam. In embodiments where the support 1242 may include a suitably comfortable material, the fluid permeable body 1220 may not include a fluid permeable membrane. In other embodiments, a fluid permeable membrane may be coupled to at least a portion of the outer surface of the support 1242, for example, as shown in FIGS. 8A-8B. In some embodiments, the fluid permeable membrane may cover a portion of the support 1242 and coupled to the fluid impermeable barrier 1202, for example as shown in FIGS. 10A-10B.

Figures 13A, 13B, 13C, 13D:
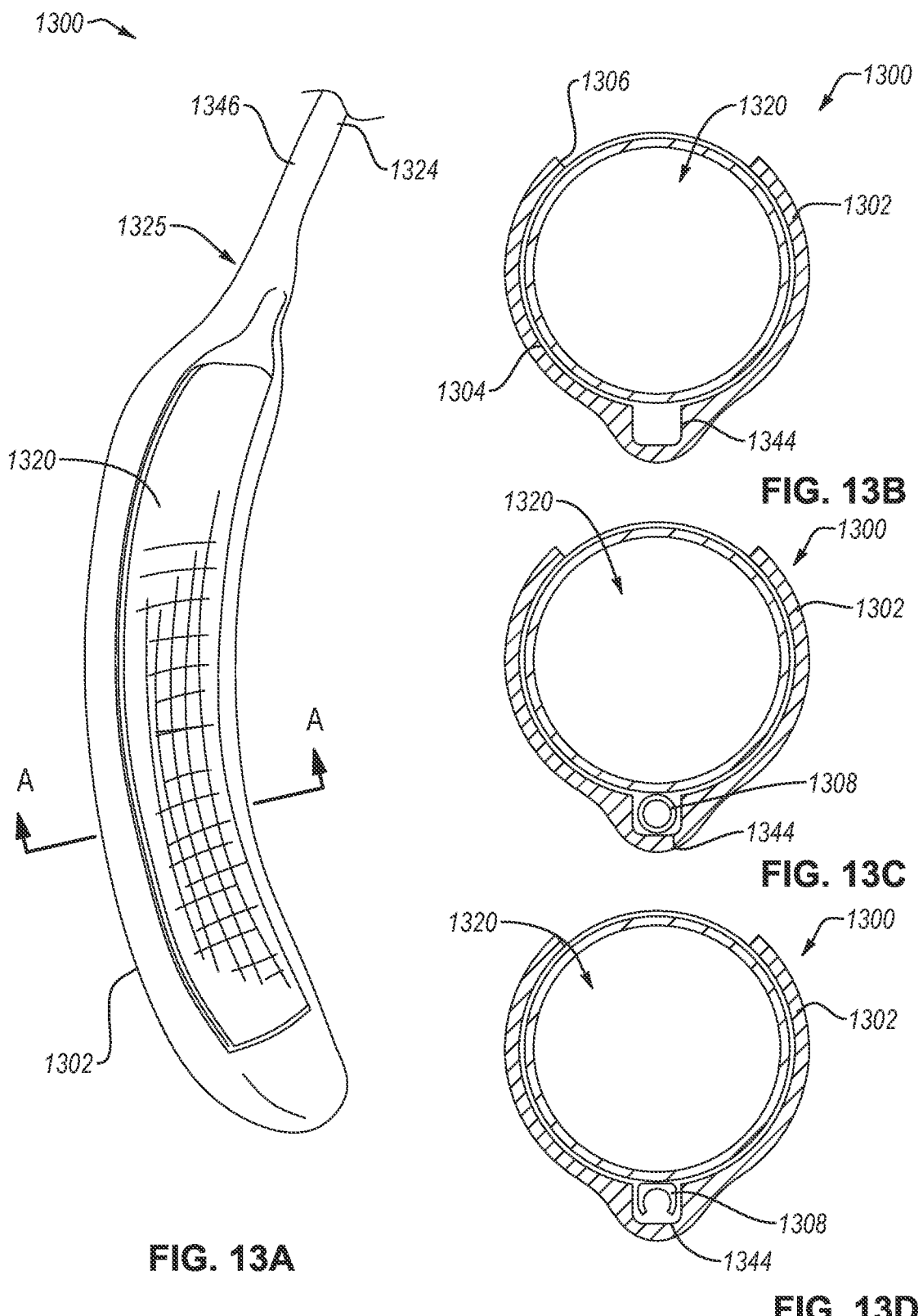
FIG. 13A is a view of a fluid collection device according to at least one embodiment of the disclosure.
FIG. 13B is a cross-sectional view of the fluid collection device along the line A-A in FIG. 13A according to at least one embodiment of the disclosure.
FIG. 13C is a cross-sectional view of the fluid collection device along the line A-A in FIG. 13A according to at least one embodiment of the disclosure.
FIG. 13D is a cross-sectional view of the fluid collection device along the line A-A in FIG. 13A according to at least one embodiment of the disclosure.

FIG. 13A is a view of a fluid collection device according to at least one embodiment of the disclosure. The fluid collection device 1300 may include a fluid impermeable barrier 1302, a fluid permeable body 1320, and, in some embodiments, a tube-like extension 1346. The tube-like extension 1346 may extend from a first end 1325 of the fluid impermeable barrier 1302 and define an aperture 1324 at an end thereof. In some embodiments, a conduit (not shown in FIG. 13A) may be inserted and/or coupled to the tube-like extension 1346.

FIG. 13B is a cross-sectional view of the fluid collection device along the line A-A in FIG. 13A according to at least one embodiment of the disclosure. In some embodiments, the fluid impermeable barrier 1302 may be similar to fluid impermeable barrier 102. However, in addition to defining an opening 1306 and a chamber 1304, the fluid impermeable barrier 1302 may further define a channel 1344 extending from the aperture 1324 (indicated in FIG. 13A) along at least a portion of a length of the fluid collection device 1300. In some embodiments, as shown in FIG. 13B, the channel 1344 may be disposed opposite the opening 1306. However, in other embodiments, the channel 1344 may be located elsewhere, for example, along a side of the chamber 1304 closer to the opening 1306. The fluid permeable body 1320 may be at least partially disposed in the chamber 1304 and cover at least a portion of the channel 1344. In some embodiments, the fluid permeable body 1320 may be substantially the same as fluid permeable body 120, 820, and/or 1020, except that no bore hole may be defined.

In some embodiments, the channel 1344 may replace at least a portion of the conduit typically inserted into the fluid impermeable barrier 1302 (e.g., conduit 108). The channel 1344 may collect fluid from the chamber 1304 and the fluid may flow through the channel 1344 to the aperture 1324 where it may be removed from the fluid collection device 1300. In some embodiments, the aperture 1324 may be coupled to a vacuum source and/or a tube coupled to the aperture may be coupled to a vacuum source and the channel 1344 may introduce suction into the chamber 1304 to facilitate removal of fluids from the chamber 1304.

FIG. 13C is a cross-sectional view of the fluid collection device along the line A-A in FIG. 13A according to at least one embodiment of the disclosure. In some embodiments, a conduit 1308 may be inserted through the aperture 1324 into the channel 1344. The channel 1344 may enclose at least a portion of the diameter of the conduit 1308. The conduit 1308 may or may not extend an entire length of the channel 1344. Other than the placement of the conduit 1308 in the channel 1344 rather than through a bore hole of the fluid permeable body 1320, the conduit 1308 may be substantially similar to the conduit 108 in some embodiments. The conduit 1308 may be retained in the channel 1344 by the fluid permeable body 1320 in some embodiments. In some embodiments, an adhesive, other bonding method (e.g., thermal), or a combination of bonding methods may be used to retain the conduit 1308 in the channel 1344. In some embodiments, the channel 1344 may be sized to provide a pressure, friction, and/or snap fit to retain the conduit 1308. In some embodiments, the conduit 1308 may extend beyond the aperture 1324. In some embodiments, the conduit 1308 may be coupled to another tube outside the aperture 1324. In some embodiments, conduit 1308 may not extend beyond the aperture 1324 and the conduit 1308 may be coupled to another tube inside the tube-like extension 1346. In some embodiments, another tube may be coupled to the tube-like extension 1346 rather than directly coupled to the conduit 1308.

FIG. 13D is a cross-sectional view of the fluid collection device along the line A-A in FIG. 13A according to at least one embodiment of the disclosure. In some embodiments, the conduit 1308 may not be a fully enclosed tube (e.g., a cylinder) but rather an arch. In these embodiments, the channel 1344 may enclose at least a portion of the sides of the arch of the conduit 1308. The channel 1344 may provide the "missing" portion of the tube in these embodiments. Similar to the embodiment shown in FIG. 13C, the conduit 1308 may be retained in the channel 1344 by the fluid permeable body 1320 in some embodiments. In some embodiments, an adhesive, other bonding method (e.g., thermal), or combination of bonding methods may be used to retain the conduit 1308 in the channel 1344. In some embodiments, the channel 1344 may be sized to provide a pressure, friction, and/or snap fit to retain the conduit 1308. In some embodiments, conduit 1308 may not extend beyond the aperture 1324 and the conduit 1308 may be coupled to another tube inside the tube-like extension 1346. In some embodiments, another tube may be coupled to the tube-like extension 1346 rather than directly coupled to the conduit 1308.

Similar to the embodiment shown in FIG. 12, the embodiments shown in FIGS. 13A-D may eliminate requiring a conduit to be inserted through the fluid permeable body. In some applications, this may reduce assembly and/or manufacturing complexity.

Figures 14A, 14B:
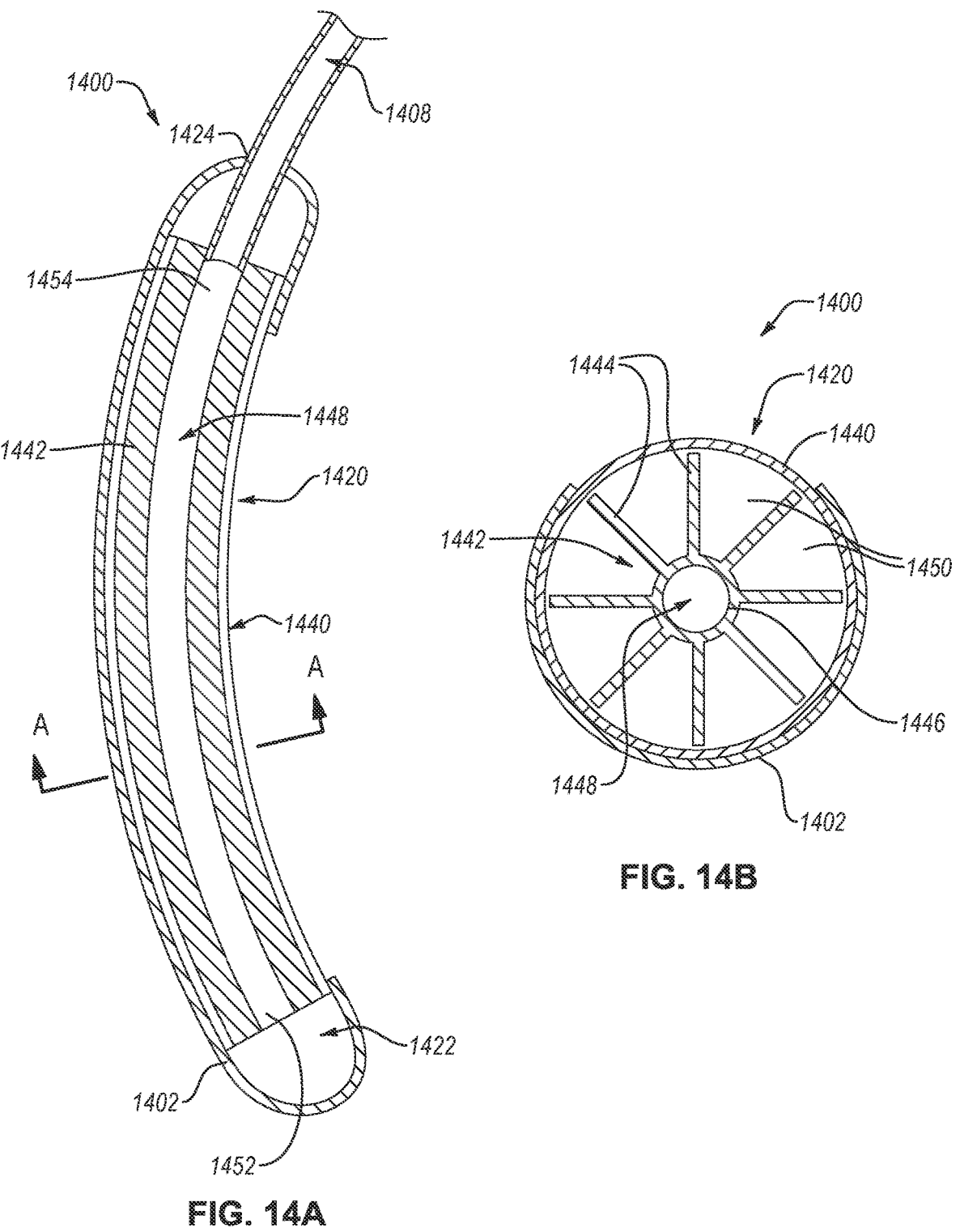
FIG. 14A is a cross-sectional view of a fluid collection device along a long axis of the fluid collection device according to at least one embodiment of the disclosure.
FIG. 14B is a cross-sectional view of the fluid collection device along the line A-A in FIG. 14A.

FIG. 14A is a cross-sectional view of a fluid collection device along a long axis of the fluid collection device according to at least one embodiment of the disclosure. The fluid collection device 1400 may include a fluid impermeable barrier 1402, a fluid permeable body 1420, and a conduit 1408. In some embodiments, the fluid impermeable barrier 1402 may be substantially the same as fluid impermeable barrier 102 and the conduit 1408 may be substantially the same as conduit 108.

In some embodiments, the fluid permeable body 1220 may include a fluid permeable membrane 1440 at least partially surrounding a support 1442. In some embodiments, the fluid permeable membrane 1440 may be substantially the same as fluid permeable membrane 340. The support 1442 may include a central tube 1448 that extends through the fluid permeable body 1420. The central tube 1448 may define a first outlet 1452 that is open to a reservoir 1422 of the fluid impermeable barrier 1402 and a second outlet 1454 proximate to an aperture 1424 defined by the fluid impermeable barrier 1402. In some embodiments, the central tube 1448 may be coupled to the conduit 1408, which may pass through the aperture 1424 as shown. The central tube 1448 may fluidly couple the conduit 1408 to the reservoir 1422. In some embodiments, such as the one shown in FIG. 14A, the conduit 1408 does not extend into the central tube 1448. In some embodiments, the conduit 1408 may extend a distance into the central tube 1448 to facilitate coupling.

FIG. 14B is a cross-sectional view of the fluid collection device along the line A-A in FIG. 14A. The support 1442 may further include multiple fins 1444 extending outward from a perimeter 1446 of the central tube 1448 to the fluid permeable membrane 1440. In some embodiments, the fins 1444 may have a length substantially equal to a length of the fluid permeable body 1420. In some embodiments, the fins 1444 may be equally spaced about the perimeter of the central tube 1448. In some embodiments, the spaces 1450 between the fins 1444 may be empty. In other embodiments, the spaces 1450 may be filled with a wicking material (e.g., open cell foam). In some embodiments, the central tube 1448 and fins 1444 may be formed of a single extruded component. The central tube 1448 and fins 1444 may include a fluid and/or air impermeable material in some embodiments. In some embodiments, the central tube 1448 and fins 1444 may include silicone, polypropylene, polyethylene, polyethylene terephthalate, a polycarbonate, a thermoplastic elastomer, etc.

Similar to the embodiment shown in FIGS. 12-13, the embodiments shown in FIGS. 14A-B may eliminate requiring a conduit to be inserted through the fluid permeable body. In some applications, this may reduce assembly and/or manufacturing complexity.

FIG. 15A is a cross-sectional view of a fluid collection device along a long axis of the fluid collection device according to at least one embodiment of the disclosure. The fluid collection device 1500 may include a fluid impermeable barrier 1502, a fluid permeable body 1520, and a conduit 1508. In some embodiments, the fluid impermeable barrier 1502 may be substantially the same as fluid impermeable barrier 102. In some embodiments, the fluid permeable body 1520 may be substantially the same as fluid permeable body 120. In some embodiments, the conduit 1508 may be substantially the same as conduit 108 except that the conduit 1508 only extends a length of the fluid permeable body 1520.

In some embodiments, a hydraulic connector 1560 may be used to couple the conduit 1508 to another tube (e.g., a tube coupled to an external reservoir and/or vacuum source), not shown. The hydraulic connector 1560 may be partially inserted into the fluid impermeable barrier 1502 through an aperture 1524 and into the conduit 1508 as indicated by arrow 1555. In some embodiments, the hydraulic connector 1560 may include barbs 1562 located proximate an end inserted through the aperture 1524. The barbs 1562 may help ensure the hydraulic connector 1560 is retained within the conduit 1508 and/or fluid impermeable barrier 1502.

FIG. 15B is a cross-sectional view of the fluid collection device of FIG. 15A showing the hydraulic connector inserted according to an embodiment of the disclosure. In some embodiments, in addition to barbs 1562, an adhesive, sealant, sonic welding, and/or other bonding technique may be used to retain the hydraulic connector 1560 in the fluid collection device 1500. The portion of the hydraulic connector 1560 extending from the fluid collection device 1500 may be coupled to another tube (not shown). Optionally, in some embodiments, the fluid impermeable barrier 1502 may include an annular rim 1564 extending from an inner surface 1503 between the fluid permeable body 1520 and a reservoir 1522. The annular rim 1564 may act as a stop to prevent the fluid permeable body 1520 from being displaced when the hydraulic connector 1560 is inserted.

In some embodiments, the fluid collection device 1500 may be assembled and provided to a wearer and/or other user (e.g., nurse, homecare assistant) with the hydraulic connector 1560 inserted through the aperture 1524. In other embodiments, the fluid collection device 1500 may be provided in a kit that includes the hydraulic connector 1560 and the wearer and/or other user may insert the hydraulic connector 1560 prior to use. In some embodiments, multiple hydraulic connectors 1560 may be provided in the kit. For example, hydraulic connectors 1560 of different sizes may be provided. The wearer and/or other user may select the appropriate hydraulic connector 1560 based on a tube size to be coupled to the hydraulic connector 1560.

In some embodiments, the hydraulic connector 1560 may allow the conduit 1508 to be made of a different material than a tube coupled to the other end of the hydraulic connector 1560. For example, in some embodiments, the conduit 1508 may include a material that is more flexible than a tube coupled to the hydraulic connector 1560. In some embodiments, the conduit 1508 may be omitted. For example, when the fluid permeable body 1420 is used to implement the fluid permeable body 1520, the hydraulic connector 1560 may be inserted into the central tube of the fluid permeable body rather than the conduit.

Figures 16A, 16B:
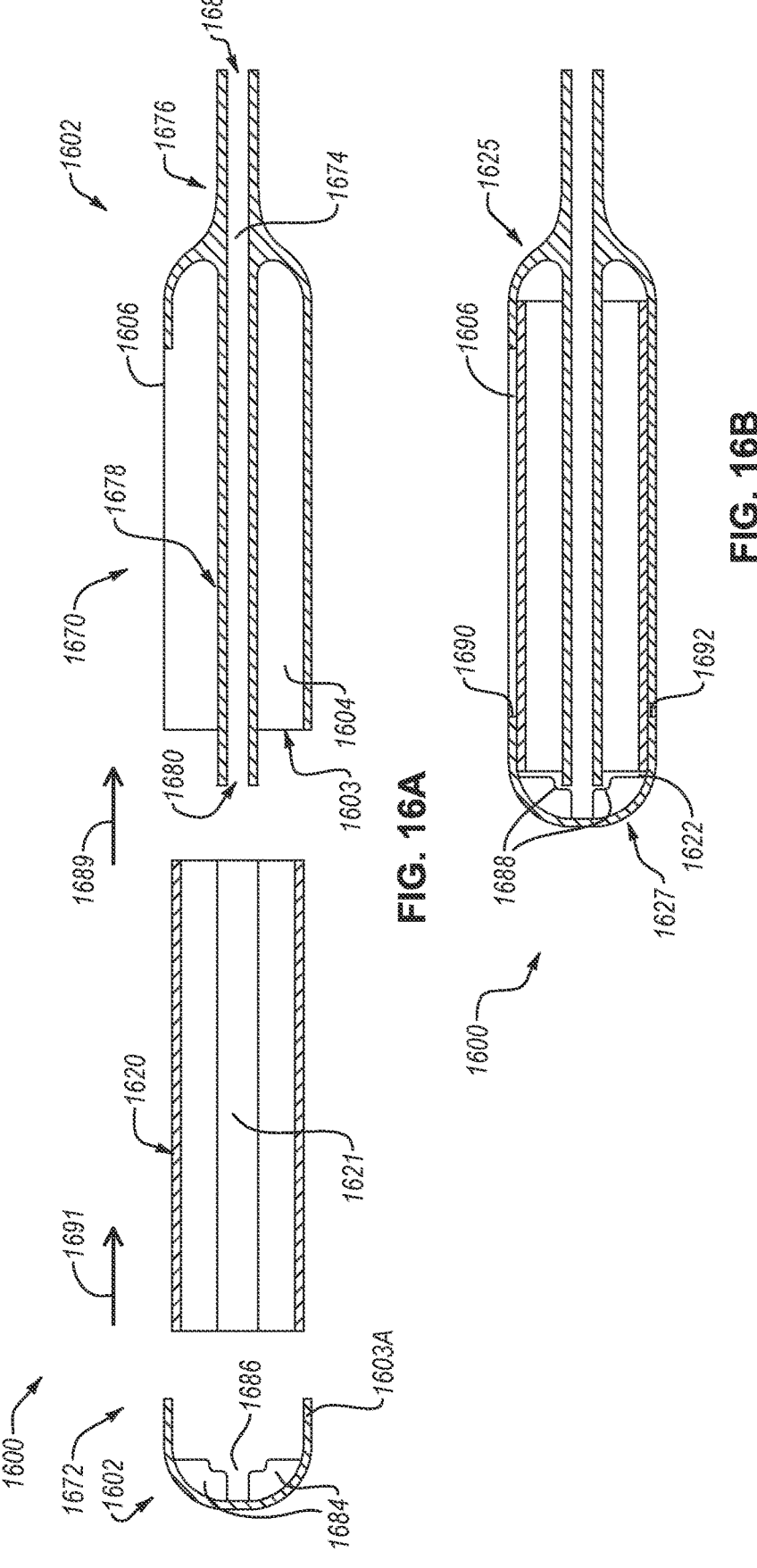
FIG. 16A is an exploded cross-sectional view of a fluid collection device along a long axis according to at least one embodiment of the present disclosure.
FIG. 16B is a cross-sectional view of the assembled fluid collection device of FIG. 16A.

FIG. 16A is an exploded cross-sectional view of a fluid collection device along a long axis according to at least one embodiment of the present disclosure. The fluid collection device 1600 may include a fluid impermeable barrier 1602 and a fluid permeable body 1620. In some embodiments, the fluid permeable body 1620 may be substantially the same as fluid permeable body 120. The fluid impermeable barrier 1602 may include a main body 1670 and an end cap 1672.

The main body 1670 may include an inner surface 1603 that defines a portion of a chamber 1604 of the fluid impermeable barrier 1602. The main body 1670 may define a portion of an opening 1606 that provides access to the chamber 1604. In some embodiments, such as the one shown, the main body 1670 may further define a tube 1674. The tube 1674 may include an outer portion 1676 that extends from an outer surface of the main body 1670 from a first end 1625 (indicated in FIG. 16B) of the fluid impermeable barrier 1602 and an inner portion 1678 that extends from the inner surface 1603 toward a second end 1627 (indicated in FIG. 16B) of the fluid impermeable barrier 1602. The tube 1674 may define an inlet 1680 at an end of the inner portion 1678 and an outlet 1682 at an end of the outer portion 1676. In some embodiments, the tube 1674 may act as at least a portion of a conduit (e.g., conduit 108) for removing fluids from the chamber 1604. In some embodiments, the tube 1674 may be fluidly coupled to another tube (not shown) at the outer portion 1676. The tube coupled to the outer portion 1676 may remove fluids from the fluid collection device 1600. In some embodiments, the tube coupled to the outer portion 1676 may provide suction (e.g., from a vacuum device) to the chamber 1604. As shown in FIG. 16A, in some embodiments, the main body 1670 may be an integrally formed component. That is, the tube 1674 and inner surface 1603 defining the chamber 1604 may be formed as a single part of the same materials at substantially the same time.

The end cap 1672 may include an inner surface 1603A that defines another portion of the chamber 1604, for example, a portion of the chamber 1604 including a reservoir 1622 (indicated in FIG. 16B). The end cap 1672 may further define a portion of the opening 1606. The end cap 1672 may include one or more tabs 1684 extending from the inner surface 1603A at the second end 1627 toward the first end 1625. The tabs 1684 may be sized to facilitate positioning of the end cap 1672 and/or tube 1674. For example, the tabs 1684 may prevent the tube 1674 from being pressed against the inner surface 1603A such that the inlet 1680 is fully or partially blocked, which may impede removal of fluid from the fluid collection device 1600. In some embodiments, the tabs 1684 may be arranged such that there is a space 1686 between the tabs 1684. The space 1686 may reduce or eliminate blockage of the inlet 1680 by the tabs 1684. In some embodiments, the tabs 1684 may have opposing curved portions 1688 (indicated in FIG. 16B). The curved portions 1688 may facilitate maintaining a position of the tube 1674 relative to the tabs 1684.

The main body 1670 and the end cap 1672 may both be injection molded components. In some embodiments, the main body 1670 and the end cap 1672 may include polypropylene and/or other materials suitable for injection molding. Optionally, in some embodiments, the main body 1670 and/or end cap 1672 may be over molded in a thermoplastic elastomer (TPE). In some applications, the TPE may replicate the look and/or feel of silicone, which may be desirable to some users.

As indicated by arrow 1689, the fluid permeable body 1620 may be inserted at least partially into the main body 1670. The fluid permeable body 1620 may define a bore 1621, through which the tube 1674 may be passed. As indicated by arrow 1691, the end cap 1672 may be placed on a portion of the fluid permeable body 1620.

FIG. 16B is a cross-sectional view of the assembled fluid collection device of FIG. 16A. In some embodiments, an edge 1690 of the end cap 1672 may be flush with an edge 1692 of the main body 1670. In other embodiments (not shown), the end cap 1672 may extend beyond the edge 1692 of the main body 1670 and partially enclose an outer surface of the main body 1670. In other embodiments (not shown), the end cap 1672 may extend beyond the edge 1692 and the edge 1690 of the end cap 1672 may be enclosed within the main body 1670. The end cap 1672 may be coupled to the main body 1670 by any suitable technique. Examples include, but are not limited to, ultrasonic welding, snap fit, adhesive, pressure fit, and/or friction fit. Once assembled, the opening 1606 and chamber 1604 may be substantially the same shape as the opening 106 and chamber 1604 in some embodiments.

The embodiment shown in FIGS. 16A-B may reduce or eliminate the need to insert a separate tube into the chamber 1604 of the fluid collection device 1600. The embodiment shown may also reduce or eliminate the need to size the opening 1606 and/or the fluid permeable body 1620 such that the fluid permeable body 1620 may be inserted through the opening 1606.

Figure 17:
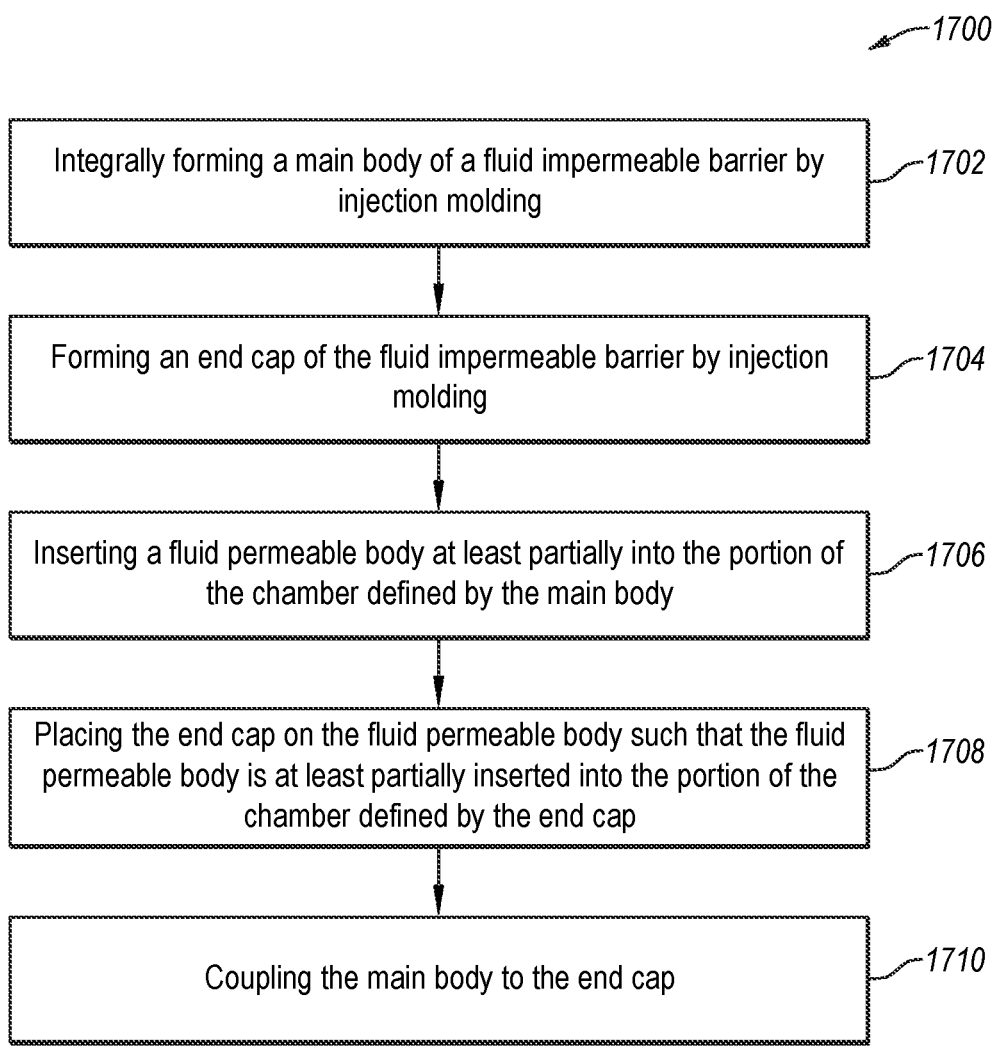
FIG. 17 is a flow chart of a method according to at least one embodiment of the disclosure.

FIG. 17 is a flow chart of a method according to at least one embodiment of the disclosure. The method 1700 may be used to manufacture, at least in part, the fluid collection device 1600 in some embodiments.

At block 1702 "integrally forming a main body of a fluid impermeable barrier by injection molding" may be performed. In some embodiments, the main body defines at least a portion of a chamber of the fluid impermeable barrier, at least a portion of an opening into the chamber and a tube extending from the chamber to an external surface of the fluid impermeable barrier. At block 1704 "forming an end cap of the fluid impermeable barrier by injection molding" may be performed. In some embodiments, the end cap defines at least another portion of the chamber. In some embodiments, blocks 1702 and 1704 may be performed simultaneously or near simultaneously. In some embodiments, block 1704 may be performed before block 1702. In some embodiments, the main body and the end cap may include polypropylene.

At block 1706 "inserting a fluid permeable body at least partially into the portion of the chamber defined by the main body" may be performed. In some embodiments, the fluid permeable body defines a bore and the tube is inserted into the bore when the fluid permeable body is inserted at least partially into the portion of the chamber defined by the main body.

At block 1708 "placing the end cap on the fluid permeable body such that the fluid permeable body is at least partially inserted in the portion of the chamber defined by the end cap" may be performed. In some embodiments, blocks 1706 and 1708 may be performed simultaneously or near simultaneously. In some embodiments, block 1708 may be performed before block 1706.

At block 1710, "coupling the main body to the end cap" may be performed. In some embodiments, coupling may include ultrasonically welding the main body to the end cap. In some embodiments, coupling may include adhering the main body to the end cap with an adhesive. In some embodiments, coupling may include snap fitting, pressure fitting, and/or friction fitting the main body and the end cap together.

Optionally, in some embodiments, the method 1700 may further include over molding at least one of the main body or the end cap with a thermoplastic elastomer. In some embodiments, this additional step may be performed after block 1702, after block 1704, or before or after block 1710.

Figures 18A, 18B, 18C:
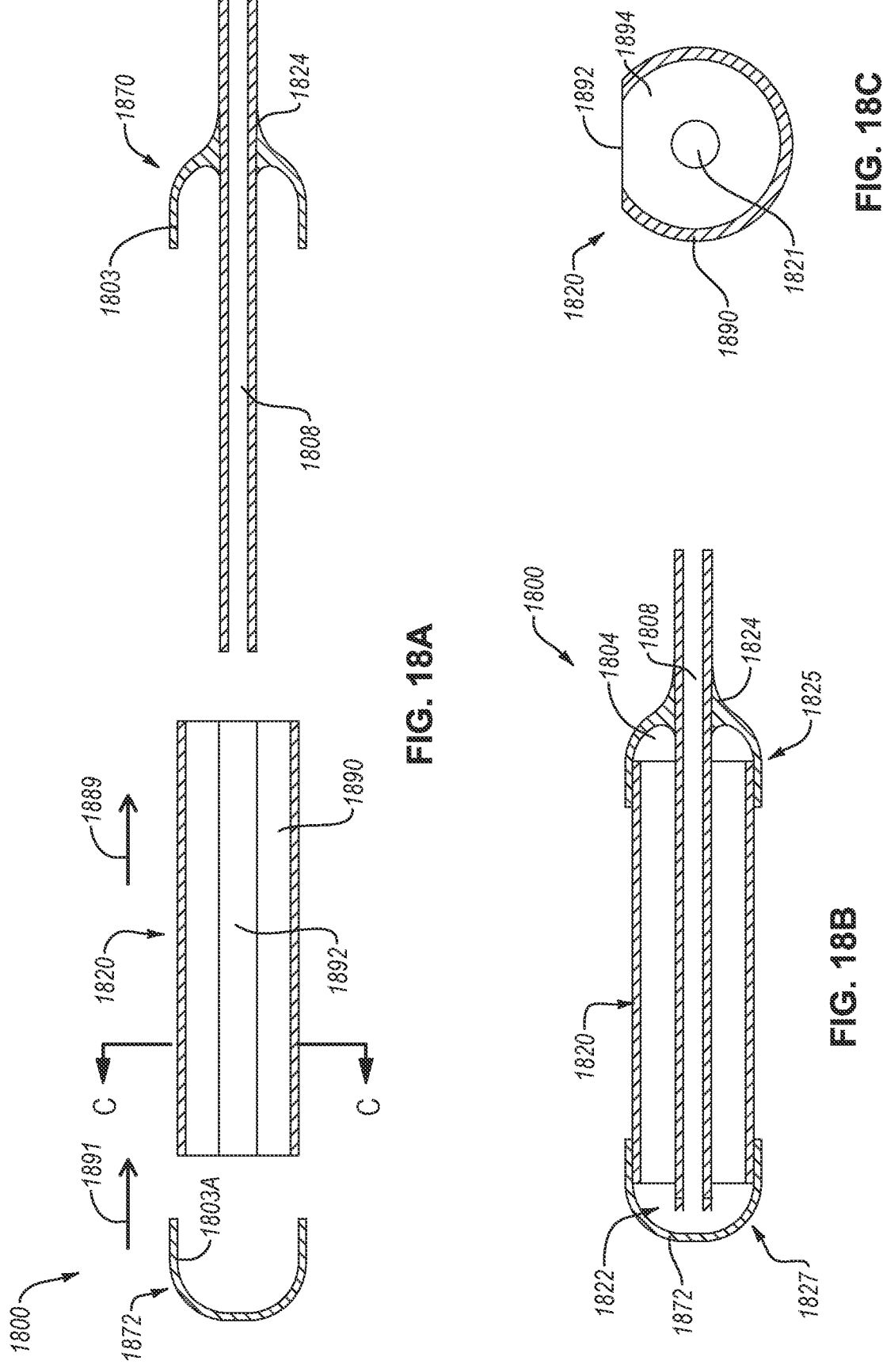
FIG. 18A is an exploded cross-sectional view of a fluid collection device along a long axis according to at least one embodiment of the present disclosure.
FIG. 18B is a cross-sectional view of the assembled fluid collection device of FIG. 18A.
FIG. 18C is a cross-sectional view of the body 1820 along line C-C in FIG. 18A.

FIG. 18A is an exploded cross-sectional view of a fluid collection device along a long axis according to at least one embodiment of the present disclosure. The fluid collection device 1800 may include a fluid impermeable cap 1870, a second fluid impermeable cap 1872, a conduit 1808, and a body 1820.

The fluid impermeable cap 1870 may include an inner surface 1803 that defines a chamber 1804 (indicated in FIG. 18B). The fluid impermeable cap 1870 may define an aperture 1824 that extends through the inner surface 1803 to an outer surface at a first end 1825 (indicated in FIG. 18B) of the fluid collection device 1800. The fluid impermeable cap 1872 may include an inner surface 1802A that defines a reservoir 1822 (indicated in FIG. 18B) at a second end 1827 of the fluid collection device 1800. In some embodiments, the fluid impermeable caps 1870 and 1872 may be formed by injection molding. The fluid impermeable caps may include polypropylene and/or other polymers suitable for injection molding.

The conduit 1808 may be disposed through the aperture 1824. In some embodiments, the conduit 1808 may be substantially the same as conduit 108. In some embodiments, the fluid impermeable cap 1870 may be welded (e.g., sonically welded) and/or otherwise coupled (e.g., adhesive, friction fit) to the conduit 1808. Alternatively, the fluid impermeable cap 1870 and conduit may be integrally formed as a single component by injection molding, similar to the main body 1670 in FIGS. 16A-B.

FIG. 18C is a cross-sectional view of the body 1820 along line C-C in FIG. 18A. The body 1820 may be substantially cylindrical in shape in some embodiments. The body 1820 may include a fluid impermeable membrane 1890 at least partially surrounding a fluid permeable core 1894. The fluid permeable core 1894 may define a bore 1821, which may extend a length of the body 1820. The fluid permeable core 1894 may be at least partially exposed at an opening 1892 in the fluid impermeable membrane 1890. The opening 1892 may be placed proximate to a wearer's urethra in some applications, similar to the opening 106 of the fluid collection device 100. The fluid permeable core 1894 may wick fluid away from the opening 1892 and toward reservoir 1822. Fluid may be temporarily stored in the reservoir 1822 before being removed from the fluid collection device 1800 via conduit 1808.

In some embodiments, the body 1820 may be formed by an integral skin polyurethane (PU) foam. Integral skin foam is a flexible foam layered or otherwise surrounded by a denser, typically less flexible foam (e.g., the skin). Both the flexible and less flexible foams may be formed in the same molding process. The skin may be a closed cell foam (e.g., PU foam) that may be used to implement the fluid impermeable membrane 1890 and the inner flexible foam may be an open cell foam (e.g., also a PU foam) that may be used to implement the fluid permeable core 1894. In some embodiments, the opening 1892 may be formed during the molding process for forming the integral skin foam. In other embodiments, the fluid impermeable membrane 1890 may completely surround the fluid permeable core 1894 and a portion of the fluid impermeable membrane 1890 is removed (e.g., cutting, sanding) to create the opening 1892. Although the fluid permeable core 1894 is shown as having a flat surface at the opening 1892 in FIG. 18C, in other embodiments, the surface at the opening 1892 may be curved (e.g., convex).

In some embodiments, the fluid permeable core 1894 may be formed by an open cell foam (e.g., PU foam, polyethylene extruded foam) and the fluid impermeable membrane 1890 may be a film or a coating applied to the outer surface of the fluid permeable core 1894 (and either not applied at the opening 1892 or later removed to form the opening 1892). The film or coating may be any suitable fluid impermeable polymer, other material, and/or composite. In some embodiments, the fluid permeable core 1894 may be coated with hydrophobic polymers. For example, in some embodiments, the fluid permeable core 1894 may be sprayed with Scotchgard by 3M to provide the fluid impermeable membrane 1890.

Returning to FIG. 18A, as indicated by arrow 1889, the body 1820 may be inserted at least partially into the fluid impermeable cap 1870. The conduit 1808 may pass at least partially through bore 1821 of the body 1820. As indicated by arrow 1891, the fluid impermeable cap 1872 may be placed on a portion of the body 1820.

FIG. 18B is a cross-sectional view of the assembled fluid collection device of FIG. 18A. The fluid impermeable caps 1870, 1872 may be coupled to the body 1820 by any suitable technique. Examples include, but are not limited to, ultrasonic welding, snap fit, adhesive, pressure fit, and/or friction fit.

The embodiment shown in FIGS. 18A-B may reduce or eliminate the materials required for a fluid impermeable barrier compared to fluid impermeable barrier 102 in some applications. In some applications, the embodiment may provide greater flexibility for the length and width of the body as the body does not need to be fit into an opening of the fluid impermeable barrier. In some applications, the embodiment may provide greater flexibility for the size of the "opening" that provides access to the fluid permeable materials for wicking fluid. For example, more of the fluid impermeable membrane 1890 may be removed (or not applied in the first place) to provide a larger area of the opening 1892.

FIG. 19 is a flow chart of a method according to at least one embodiment of the disclosure. The method 1900 may be used to manufacture, at least in part, the fluid collection device 1800 in some embodiments.

At block 1902 "forming a first fluid impermeable cap by injection molding, wherein the first fluid impermeable cap defines at least a portion of a chamber and an aperture therethrough" may be performed. At block 1904 "forming a second fluid impermeable cap by injection molding, wherein the second fluid impermeable cap defines at least a portion of a reservoir" may be performed. In some embodiments, blocks 1902 and 1904 may be performed simultaneously or near simultaneously. In some embodiments, block 1904 may be performed before block 1902.

At block 1906 "inserting a conduit through the aperture of the first fluid impermeable cap" may be performed. Optionally, in some embodiments, method 1900 may further include coupling the conduit to the first fluid impermeable cap. In some embodiments, coupling may include ultrasonic welding and/or applying an adhesive. In some embodiments, block 1906 may be performed before block 1904. In some embodiments, block 1906 may be performed simultaneously or near simultaneously with block 1904.

At block 1908 "inserting a first end of a body at least partially into the portion of the chamber defined by the first fluid impermeable cap" may be performed. At block 1910 "inserting a second end of the body at least partially into the portion of the reservoir defined by the second fluid impermeable cap" may be performed. In some embodiments, the body defines a bore and the conduit is inserted through the bore. In some embodiments, blocks 1908 and 1910 may be performed simultaneously or near simultaneously. In some embodiments, block 1910 may be performed before block 1908.

At block 1912 "coupling the first and second fluid impermeable caps to the body" may be performed. In some embodiments, coupling may include ultrasonically welding the first and second fluid impermeable caps to the body. In some embodiments, coupling may include applying an adhesive to adhere the first and second fluid impermeable caps to the body.

In some embodiments, the body may include a fluid permeable core and the method 1900 may further include "coating a portion of the fluid permeable core with a fluid impermeable membrane" shown in block 1914.

In some embodiments, the body may include a fluid permeable core surrounded by a fluid impermeable membrane and method 1900 may further include "removing a portion of the fluid impermeable membrane to expose a portion of the fluid permeable core" shown in block 1916.

Some or all of the embodiments disclosed herein may be used in combination. For example, the fluid impermeable cap 1872 of fluid collection device 1800 may optionally include the tabs 1684 of fluid collection device 1600. In another example, the fluid permeable body 1620 of fluid collection device 1600 may include the fluid permeable body 820. Alternatively, the fluid collection device 1600 may include a fluid permeable membrane coupled to the fluid impermeable barrier 1602 as shown in FIGS. 10A-B.

The various apparatuses and methods disclosed herein for providing fluid collection devices may reduce cost, permit additional automation, and/or reduce time of manufacture in some applications. In some applications, the apparatuses and methods disclosed herein may make the fluid collection devices easier to assemble, couple to a vacuum source and/or external fluid collection reservoir, and/or otherwise put into use. In some applications, the apparatuses and methods disclosed herein may permit additional automation in manufacturing, reduce cost, improve performance of the fluid collection device, and/or make the fluid collection devices easier to assemble or put in use.

As used herein, the term "about" or "substantially" refers to an allowable variance of the term modified by "about" or "substantially" by ±10% or ±5%. Further, the terms "less than," "or less," "greater than," "more than," or "or more" include, as an endpoint, the value that is modified by the terms "less than," "or less," "greater than," "more than," or "or more."

While various aspects and embodiments have been disclosed herein, other aspects and embodiments are contemplated. The various aspects and embodiment disclosed herein are for purposes of illustration and are not intended to be limiting.

We claim:

1. A method of manufacturing a portion of a fluid collection device, comprising:

drawing a length of tubing through a first set of motorized rollers by rotating rollers of the first set of motorized rollers in opposing directions;

drawing the length of tubing through a second set of motorized rollers by rotating rollers of the second set of motorized rollers in opposing directions;

stopping rotation of the first set of motorized rollers and the second set of motorized rollers when an end of the length of tubing contacts a stop;

cutting the length of tubing at a location between the first set of motorized rollers and the second set of motorized rollers; and inserting the length of tubing at least partially into a chamber of a fluid impermeable barrier of the fluid collection device.

2. The method of claim 1, further comprising ejecting a cut portion of the length of tubing from a tube cutting apparatus including the first set and the second set of motorized rollers.

3. The method of claim 2, wherein ejecting the cut portion of the length of tubing comprises actuating a piston.

4. The method of claim 1, further comprising detecting when the end of the length of tubing contacts the stop with a sensor included with the stop.

5. The method of claim 4, further comprising detecting when the end of the length of tubing contacts the stop when a torque on at least one of the first set of motorized rollers or the second set of motorized rollers increases.

6. The method of claim 1, wherein the length of tubing comprises a fluid impermeable tubing.

7. The method of claim 6, wherein the fluid impermeable tubing comprises polyvinyl chloride.

8. The method of claim 1, wherein the length of tubing comprises a fluid permeable material.

9. The method of claim 8, wherein the fluid permeable material comprises an open cell foam.

10. The method of claim 1, wherein cutting the length of tubing comprises actuating a blade.

\* \* \* \* \*